US011771093B2

(12) United States Patent
Shinde et al.

(10) Patent No.: US 11,771,093 B2
(45) Date of Patent: *Oct. 3, 2023

(54) CHLORELLA-BASED COMPOSITION, AND METHODS OF ITS PREPARATION AND APPLICATION TO PLANTS

(71) Applicant: HELIAE DEVELOPMENT, LLC, Gilbert, AZ (US)

(72) Inventors: Sandip Shinde, Gilbert, AZ (US); Stephen Ventre, Mesa, AZ (US); Nicholas Donowitz, Shelburne, VT (US); Michael Rohlfsen, Edina, MN (US); Laura Carney, Gilbert, AZ (US)

(73) Assignee: HELIAE DEVELOPMENT, LLC, Gilbert, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/838,942

(22) Filed: Jun. 13, 2022

(65) Prior Publication Data

US 2022/0322678 A1    Oct. 13, 2022

Related U.S. Application Data

(63) Continuation of application No. 16/952,387, filed on Nov. 19, 2020, now Pat. No. 11,412,739, which is a continuation of application No. 16/430,200, filed on Jun. 3, 2019, now Pat. No. 10,869,484, which is a continuation of application No. 15/536,705, filed as application No. PCT/US2015/066160 on Dec. 16, 2015, now Pat. No. 10,357,038, which is a continuation of application No. 14/602,331, filed on Jan. 22, 2015, now abandoned, and a continuation of application No. 14/602,348, filed on Jan. 22, 2015, now abandoned, and a continuation of application No. 14/602,356, filed on Jan. 22, 2015, now abandoned, and a continuation of application No. 14/602,362, filed on Jan. 22, 2015, now Pat. No. 9,386,774.

(60) Provisional application No. 62/092,766, filed on Dec. 16, 2014, provisional application No. 62/092,771, filed on Dec. 16, 2014, provisional application No. 62/092,774, filed on Dec. 16, 2014, provisional application No. 62/092,703, filed on Dec. 16, 2014, provisional application No. 62/092,777, filed on Dec. 16, 2014.

(51) Int. Cl.
*A01N 65/03* (2009.01)
*A01N 65/00* (2009.01)
*A01N 63/00* (2020.01)
*C12N 1/12* (2006.01)

(52) U.S. Cl.
CPC ............. *A01N 65/03* (2013.01); *A01N 63/00* (2013.01); *A01N 65/00* (2013.01); *C12N 1/12* (2013.01)

(58) Field of Classification Search
None
See application file for complete search history.

(56) References Cited

U.S. PATENT DOCUMENTS

| | | | | |
|---|---|---|---|---|
| 9,386,774 | B2 * | 7/2016 | Shinde | A01N 65/03 |
| 10,357,038 | B2 * | 7/2019 | Shinde | A01N 63/00 |
| 10,517,303 | B2 * | 12/2019 | Shinde | C12N 1/12 |
| 10,631,543 | B2 * | 4/2020 | Carney | A01N 63/20 |
| 10,645,937 | B2 * | 5/2020 | Carney | A01N 65/03 |
| 10,694,751 | B2 * | 6/2020 | Carney | A01N 63/30 |
| 10,701,941 | B2 * | 7/2020 | Carney | C05F 11/08 |
| 10,869,484 | B2 * | 12/2020 | Shinde | A01N 65/03 |
| 11,039,622 | B2 * | 6/2021 | Shinde | A01N 65/03 |
| 11,102,985 | B2 * | 8/2021 | Carney | A01N 61/00 |
| 11,109,595 | B2 * | 9/2021 | Shinde | A61P 31/10 |
| 11,197,474 | B2 * | 12/2021 | Shinde | A01H 5/10 |
| 11,259,527 | B2 * | 3/2022 | Shinde | C05F 11/08 |
| 11,412,739 | B2 * | 8/2022 | Shinde | A01N 63/00 |
| 11,518,721 | B2 * | 12/2022 | Chen | C05F 11/00 |
| 2014/0090431 | A1 * | 4/2014 | Blotsky | C05F 11/08 |
| | | | | 510/109 |

(Continued)

FOREIGN PATENT DOCUMENTS

CN    1326702 A  * 12/2001
JP    60069183 A  *  4/1985

(Continued)

OTHER PUBLICATIONS

Watkinson et al.( Efficacy of non-chemical weed control during plug establishment of a wildflower meadow(Journal of Environmental Horticulture, (Jun. 2007) vol. 25, No. 2, pp. 83-88). (Year: 2007).*
Wang et al., Development of Chlorella drink, Shipin Yu Fajiao Gongye (2001), 27(1), 84-86 (Year: 2001).*
Raposo et al., "Chlorella vulgaris as Soil Amendment: Influence of Encapsulation and Enrichment with Rhizobacteria", International Journal of Agriculture & Biology, 2011, pp. 719-724, vol. 13, No. 5.

(Continued)

*Primary Examiner* — Alton N Pryor
(74) *Attorney, Agent, or Firm* — Timothy Marc Shropshire

(57) ABSTRACT

Liquid agricultural compositions comprising pasteurized *Chlorella* cells, as well as methods of preparation and use thereof, are disclosed. The compositions are formulated for application to a plant, seed, seedling, or soil and are effective in enhancing at least one plant characteristic including, but not limited to: seed germination, seedling emergence, seedling size, plant fresh weight, plant dry weight, utilization, leaf production, leaf formation, thatch height, plant maturation, plant yield, plant growth, plant quality, plant health, plant resistance to salt stress, plant resistance to heat stress, plant resistance to heavy-metal stress, plant resistance to drought, maturation time, yield, root length, root mass, color, fruit production, fruit yield, fruit growth, and fruit quality.

20 Claims, 7 Drawing Sheets

(56) References Cited

U.S. PATENT DOCUMENTS

2014/0298717 A1* 10/2014 Ayers .................. C12M 37/00
                                                         47/1.4
2023/0061833 A1*  3/2023 Chen .................... C05F 11/00

FOREIGN PATENT DOCUMENTS

| JP | 07264986 A  * | 10/1995 | |
|----|---------------|---------|---|
| JP | 2006083360 A  * | 3/2006 | ............ B82Y 30/00 |
| JP | 2007291051 A  * | 11/2007 | |
| RU | 2562544 C2 * | 9/2015 | |
| WO | 2013123032 A1 | 8/2013 | |

OTHER PUBLICATIONS

Faheed et al., "Effect of Chlorella vulgaris as Bio-fertilizer on Growth Parameters and Metabolic Aspects of Lettuce Plant", Journal of Agriculture and Social Sciences, 2008, pp. 165-169, vol. 4, No. 4.

Kang et al., "Comparison of Rheological Properties of Powder *Chlorella* sp. Cultivated in Fermentor and Pond", Journal of Microbiology and Biotechnology, 2002, pp. 740-745, vol. 12, No. 5.

Safi et al., "Morphology, composition, production, processing and applications of Chlorella vulgaris: A review", Renewable and Sustainable Energy Reviews, 2014, pp. 265-278, vol. 35.

Dubey et al., "Evaluation of Cost Effective Organic Fertilizers", Organic Eprints, 2010, pp. 1-7.

\* cited by examiner

DAPI-DNA binding dye

Propidium Iodide is an exclusion dye-labels DNA is cell membrane is compromised

|  | Temperature (C) | | | | |
|---|---|---|---|---|---|
|  | 50 | 60 | 70 | 80 | 90 |
| 15 | 94700 | 253000 | 703000 | 240000 | 14100 |
| 30 | 117000 | 213000 | 273000 | 240000 | 4830 |
| 60 | 72700 | 159000 | 3030000 | 123000 | 6740 |
| 120 | 367000 | 124000 | 168000 | 157000 | 6240 |
| 180 | 156000 | 7580000 | 202000 | 43000 | 7470 |
| 360 | 1030000 | 703000 | 257000 | 13500 | 1740 |

Time (min) shown on left axis.

CHLORELLA-BASED COMPOSITION, AND METHODS OF ITS PREPARATION AND APPLICATION TO PLANTS

CROSS-REFERENCE TO RELATED APPLICATIONS

This application is a continuation of, and claims priority to, U.S. application Ser. No. 16/952,387, titled "Chlorella-Based Composition, and Methods of its Preparation and Application to Plants", filed Nov. 19, 2020. U.S. application Ser. No. 16/952,387 is a continuation of, and claims priority to, U.S. application Ser. No. 16/430,200, titled "Chlorella-Based Composition for Application to Plants and Methods of its Preparation", filed Jun. 3, 2019 and issued as U.S. Pat. No. 10,869,484 on Dec. 22, 2020. U.S. application Ser. No. 16/430,200 is a continuation of, and claims priority to, U.S. application Ser. No. 15/536,705, titled "Mixotrophic Chlorella-Based Composition, and Methods of its Preparation and Application to Plants", filed Jun. 16, 2017 and issued as U.S. Pat. No. 10,357,038 on Jul. 23, 2019. U.S. application Ser. No. 15/536,705 is a National Stage Entry of, and claims priority to, International PCT Application No. PCT/US2015/066160, titled "Mixotrophic Chlorella-Based Composition, and Methods of its Preparation and Application to Plants", filed Dec. 16, 2015. International PCT Application No. PCT/US2015/066160 claims priority to U.S. Provisional Application No. 62/092,766, titled "Methods of Preparing a Mixotrophic Chlorella Based Composition for Application to Plants", filed Dec. 16, 2014; U.S. Provisional Application No. 62/092,771, titled "Application of Mixotrophic Chlorella for the Accelerated Emergence and Maturation of Fabaceae Plants", filed Dec. 16, 2014; U.S. Provisional Application No. 62/092,774, titled "Application of Mixotrophic Chlorella for the Accelerated Emergence and Maturation of Solanaceae Plants", filed Dec. 16, 2014; U.S. Provisional Application No. 62/092,703, titled "Application of Mixotrophic Chlorella for the Improved Yield and Quality of Solanaceae Plants", filed Dec. 16, 2014; U.S. Provisional Application No. 62/092,777, titled "Mixotrophic Chlorella Based Composition for Application to Plants", filed Dec. 16, 2014; U.S. application Ser. No. 14/602,331, titled "Methods of Preparing a Mixotrophic Chlorella Based Composition for Application to Plants", filed Jan. 22, 2015; U.S. application Ser. No. 14/602,348, titled "Application of Mixotrophic Chlorella for the Accelerated Emergence and Maturation of Fabaceae Plants", filed Jan. 22, 2015; U.S. application Ser. No. 14/602,356, titled "Application of Mixotrophic Chlorella for the Accelerated Emergence and Maturation of Solanaceae Plants", filed Jan. 22, 2015; and U.S. application Ser. No. 14/602,362, titled "Application of Mixotrophic Chlorella for the Improved Yield and Quality of Solanaceae Plants", filed Jan. 22, 2015 and issued as U.S. Pat. No. 9,386,774 on Jul. 12, 2016. The entire contents of each of the foregoing applications are hereby incorporated by reference herein.

BACKGROUND

Seed emergence occurs as an immature plant breaks out of its seed coat, typically followed by the rising of a stem out of the soil. The first leaves that appear on many seedlings are the so-called seed leaves, or cotyledons, which often bear little resemblance to the later leaves. Shortly after the first true leaves, which are more or less typical of the plant, appear, the cotyledons will drop off. Germination of seeds is a complex physiological process triggered by imbibition of water after possible dormancy mechanisms have been released by appropriate triggers. Under favorable conditions rapid expansion growth of the embryo culminates in rupture of the covering layers and emergence of the radicle. A number of agents have been proposed as modulators of seed emergence. Temperature and moisture modulation are common methods of affecting seed emergence. Addition of nutrients to the soil has also been proposed to promote emergence of seeds of certain plants.

Similarly, the growth and fruit production of a mature plant is also a complex physiological process involving inputs and pathways in the roots, shoot, and leaves. Whether at a commercial or home garden scale, growers are constantly striving to optimize the yield and quality of a crop to ensure a high return on the investment made in every growth season. As the population increases and the demand for raw plant materials goes up for the food and renewable technologies markets, the importance of efficient agricultural production intensifies. The influence of the environment on a plant's health and production has resulted in a need for strategies during the growth season which allow the plants to compensate for the influence of the environment and maximize production. Addition of nutrients to the soil or application to the foliage has also been proposed to promote yield and quality in certain plants. The effectiveness can be attributable to the ingredients or the method of preparing the product. Increasing the effectiveness of a product can reduce the amount of the product needed and increase efficiency of the agricultural process.

SUMMARY

Embodiments of the present invention provide a liquid Chlorella-based composition and methods for preparing same. The composition can include pasteurization and stabilization of a given concentration of mixotrophic Chlorella whole cells that have not been subjected to a drying process. The liquid composition can be used to enhance the emergence and growth of plants via soil and/or foliar applications.

In some embodiments, the composition can comprise 5-30% solids by weight of whole mixotrophic Chlorella cells. In some embodiments, the composition can comprise 5-20% solids by weight of whole mixotrophic Chlorella cells. In some embodiments, the composition can comprise 5-15% solids by weight of whole mixotrophic Chlorella cells. In some embodiments, the composition can comprise 5-10% solids by weight of whole mixotrophic Chlorella cells. In some embodiments, the composition can comprise 10-20% solids by weight of whole mixotrophic Chlorella cells. In some embodiments, the composition can comprise 10-20% solids by weight of whole mixotrophic Chlorella cells. In some embodiments, the composition can comprise 20-30% solids by weight of whole mixotrophic Chlorella cells. In some embodiments, further dilution of the whole mixotrophic Chlorella cells percent solids by weight can be occur before application for low concentration applications of the composition. The composition can be diluted to a lower concentration for an effective amount in a soil or foliar application by mixing a volume of the composition in a volume of water. The percent solids of mixotrophic Chlorella whole cells resulting in the diluted composition can be calculated by multiplying the original percent solids of mixotrophic Chlorella whole cells in the composition by the ratio of the volume of the composition to the volume of water.

In some embodiments, the *Chlorella* cells can be pasteurized at between 50 and 80° C. for a time between 15 and 360 minutes. In some embodiments, the *Chlorella* cells can be pasteurized in a culture having a concentration greater than 11% by weight of *Chlorella*, at between 55 and 65° C. for between 90 and 150 minutes. In some embodiments, the culture can be then diluted to 10-11% *Chlorella* by weight and cooled to between 35 and 45° C. In some embodiments, the pasteurized culture can be adjusted to a pH between 3.5 and 4.5.

In some embodiments, the *Chlorella* cells can be cultured in mixotrophic conditions. In some embodiments, the mixotrophic conditions include culturing the *Chlorella* cells in a suitable medium for a culture length of 7-14 days, at a temperature between 20 and 30° C., at a pH between 6.5 and 8.5, and a dissolved oxygen concentration can range between 0.1 and 4 mg/L.

In some embodiments, the *Chlorella* cells can be cultured in non-axenic mixotrophic conditions. In some embodiments, at least one species of sporulating bacterium can be present in the non-axenic culture. The bacterium can be *Paenibacillus* sp., *Bacillus* sp., *Lactobacillus* sp., *Brevibacillus* sp., or similar.

In some embodiments, administration of the composition can be by soaking a seed in the composition prior to planting; contacting soil in an immediate vicinity of a planted seed with an effective amount of the composition; contacting roots of a plant with an effective amount of the composition hydroponically; contacting an effective amount of the composition to an accessible portion of the plant after emergence; or similar.

In some embodiments, the liquid composition can be administered at a rate in the range of 10-150 gallons per acre to soil or to emerged plants in soil.

In some embodiments, the seed can be soaked for 90-150 minutes.

In some embodiments, the liquid composition can include 0.008-0.080% solids by weight of whole pasteurized *Chlorella* cells.

In some embodiments, the liquid compositions can be administered by spraying. The compositions can be administered every 3-28 days or every 4-10 days or similar. In some embodiments, the liquid composition can be first administered 5-14 days after emergence.

In some embodiments, the liquid composition can be administered to the soil by a low volume irrigation system, a soil drench application, an aerial spraying system, or the like.

In some embodiments, the plant can be a member of a plant family Solanaceae, Fabaceae (Leguminosae), Poaceae, Roasaceae, Vitaceae, Brassicaeae (Cruciferae), Caricaceae, Malvaceae, Sapindaceae, Anacardiaceae, Rutaceae, Moraceae, Convolvulaceae, Lamiaceae, Verbenaceae, Pedaliaceae, Asteraceae (Compositae), Apiaceae (Umbelliferae), Araliaceae, Oleaceae, Ericaceae, Actinidaceae, Cactaceae, Chenopodiaceae, Polygonaceae, Theaceae, Lecythidaceae, Rubiaceae, Papveraceae, Illiciaceae Grossulariaceae, Myrtaceae, Juglandaceae, Bertulaceae, Cucurbitaceae, Asparagaceae (Liliaceae), Alliaceae (Liliceae), Bromeliaceae, Zingieraceae, Muscaceae, Areaceae, Dioscoreaceae, Myristicaceae, Annonaceae, Euphorbiaceae, Lauraceae, Piperaceae, Proteaceae, or the like.

In some embodiments, the whole *Chlorella* cells have not been subjected to a drying process.

In some embodiments, the liquid composition treatment can further include at least one culture stabilizer suitable for plants. The culture stabilizer can be potassium sorbate, phosphoric acid, ascorbic acid, sodium benzoate, or the like, or any combination thereof.

In some embodiments, the liquid composition treatment does not contain an active ingredient for enhancing emergence or maturation other than the culture of whole *Chlorella* cells.

In some embodiments, enhancement can be determined by comparison of a treated plant with a substantially identical untreated plant. A quantifiable difference of at least 10% can be observed for at least one plant characteristic.

In some embodiments, the plant characteristic can be seed germination rate, seed germination time, seedling emergence, seedling emergence time, seedling size, plant fresh weight, plant dry weight, utilization, fruit production, leaf production, leaf formation, thatch height, plant health, plant resistance to salt stress, plant resistance to heat stress, plant resistance to heavy-metal stress, plant resistance to drought, maturation time, yield, root length, root mass, color, insect damage, blossom end rot, softness, fruit quality, and sunburn, or the like, or any combination thereof.

In some embodiments, the number of plants emerged from the soil can be increased by at least 10% compared to a substantially identical population of untreated plants. In some embodiments, the number of plants demonstrating maturation by leaf formation can increased by at least 10% compared to a substantially identical population of untreated plants.

Embodiments of the invention provide a liquid composition for plant enhancement, the composition including whole pasteurized *Chlorella* cells. In some embodiments, the composition can be a pasteurized axenic culture, wherein at least one species of sporulating bacterium can be present. In some embodiments, the bacterium can be selected from *Paenibacillus* sp., *Bacillus* sp., *Lactobacillus* sp., *Brevibacillus* sp., and any combination thereof. In some embodiments, the bacterial flora includes at least five other bacteria in addition to all of *Paenibacillus* sp., *Bacillus* sp., *Lactobacillus* sp., *Brevibacillus* sp. The bacterial flora can also include any one or more of the bacteria listed below:

*Paenibacillus* sp.
*Bacillus* sp.
*Lactobacillus* sp.
*Brevibacillus* sp.
*Massilia* sp.
*Pseudomonas* sp.
*Bdellovibrio bacteriovorus*
*Stenotrophomonas* sp.
*Acinetobacter* sp.
*Enterobacter* sp.
*Flavobacterium* sp.
*Zoogloea* sp. algae associated
Burkholderiaceae—fam
Xanthomonadaceae—fam
Enterobacteriaceae—fam
Comamonadaceae—fam
Oxalobacteraceae—fam
Chitinopagaceae—fam
Gamma-proteobacterium—class
Burkholderiales—fam
Proteobacteria—phy
Singleton Taxa
Unclassified bacterium In some embodiments of the invention, the composition can be from 0.0001%-40% *Chlorella* by weight. In some embodiments, the composition can be 10-11% *Chlorella* by weight. In some embodiments, the pasteurized culture can be at a pH between 3.5 and 4.5. In various embodiments, the *Chlorella* can be a mixotrophic culture, grown on at least one organic carbon source as well as via photosynthesis. In some embodiments, the composition further includes a suitable medium for *Chlorella* growth. In some embodiments, the composition can be diluted with water. Likewise, in some embodiments, the composition can include other additives including fertilizers, pH adjusters, plant hormones, insecticides, minerals, detergents. In some embodiments, the composition does not contain an additive for enhancing emergence or maturation other than the culture of whole *Chlorella* cells.

Some embodiments of the invention provide a soil harboring a plant seed, including the composition, wherein the seed has an improved characteristic. In some embodiments, the invention provides a plant seed, contacted by the composition, wherein the seed has an improved characteristic. Likewise, in some embodiments, the invention provides roots of a plant contacted with an effective amount of the composition, hydroponically or in soil, wherein the root or the whole plant has an improved characteristic. In still other embodiments, the invention provides a plant contacted with the composition after emergence, wherein the plant has an improved characteristic.

Some embodiments of the invention include a low volume irrigation system including the composition. In some embodiments, the invention includes a soil drench system, and/or an aerial spraying system including the composition.

In some embodiments, the composition further includes at least one culture stabilizer suitable for plants. In some embodiments, the culture stabilizer can be selected from: potassium sorbate, phosphoric acid, ascorbic acid, sodium benzoate, and any combination thereof.

Some embodiments of the invention provide harvested material from a plant contacted by the composition, wherein the plant displayed an improved characteristic. In some embodiments, the improved characteristic can be present in the harvested material.

Some embodiments of the invention include turf contacted by the composition, the turf having an improved characteristic. In some embodiments, a field of such turf can be provided as part of the invention. In some embodiments, the invention includes a golf course with the turf.

Some embodiments of the invention provide a plant rendered stress-resistant by contact with the composition. Likewise, some embodiments of the invention provide soil rendered arable by spraying or soaking with the composition in presence of seeds or plants made sufficiently resistant to stress to be capable of growth in the soil.

DETAILED DESCRIPTION

Figure 1:
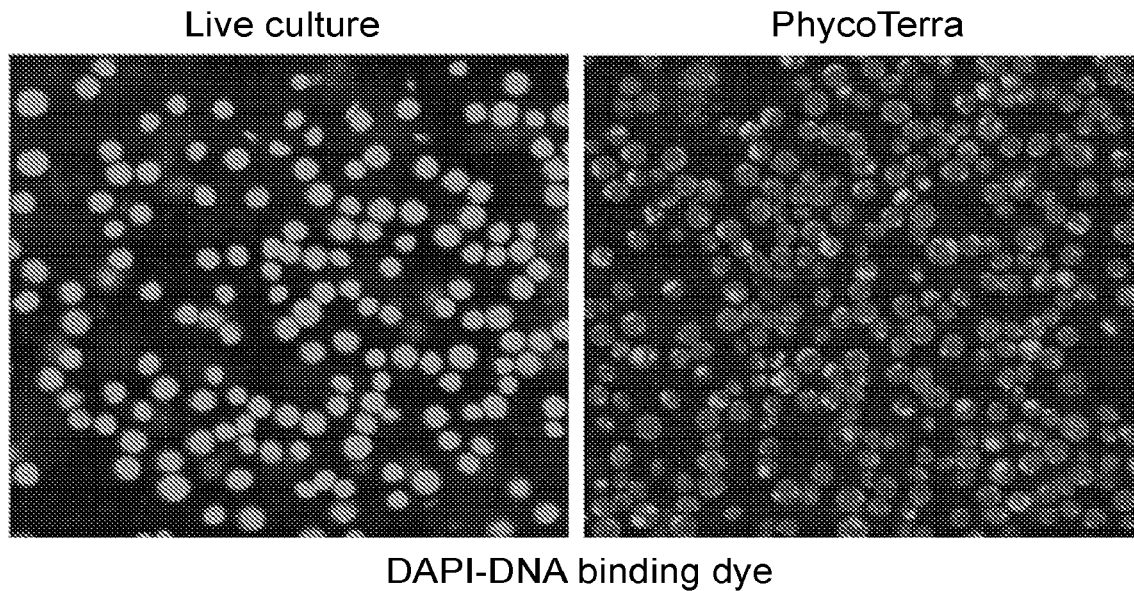
FIG. 1 depicts the results of a test for the condition of the DNA of *Chlorella* cells after pasteurization (DAPI).

Many plants can benefit from the application of liquid compositions that provide a bio-stimulatory effect. Non-limiting examples of plant families that can benefit from such compositions can include: Solanaceae, Fabaceae (Leguminosae), Poaceae, Roasaceae, Vitaceae, Bras sicaeae (Cruciferae), Caricaceae, Malvaceae, Sapindaceae, Anacardiaceae, Rutaceae, Moraceae, Convolvulaceae, Lamiaceae, Verbenaceae, Pedaliaceae, Asteraceae (Compositae), Apiaceae (Umbelliferae), Araliaceae, Oleaceae, Ericaceae, Actinidaceae, Cactaceae, Chenopodiaceae, Polygonaceae, Theaceae, Lecythidaceae, Rubiaceae, Papveraceae, Illiciaceae Grossulariaceae, Myrtaceae, Juglandaceae, Bertulaceae, Cucurbitaceae, Asparagaceae (Liliaceae), Alliaceae (Liliceae), Bromeliaceae, Zingieraceae, Muscaceae, Areaceae, Dioscoreaceae, Myristicaceae, Annonaceae, Euphorbiaceae, Lauraceae, Piperaceae, and Proteaceae.

The Fabaceae plant family (also known as the Leguminosae) comprises the third largest plant family with over 18,000 species, including a number of important agricultural and food plants. Taxonomically classified in the Plantae kingdom, Tracheobionta (subkingdom), Spermatophyta (superdivision), Magnoliophyta (division), Manoliopsida (class), Rosidae (subclass), and Fabales (order), the Fabaceae family includes, but is not limited to, soybeans, beans, green beans, peas, chickpeas, alfalfa, peanuts, sweet peas, carob, and liquorice. Plants in the Fabaceae family can range in size and type, including but not limited to, trees, small annual herbs, shrubs, and vines, and typically develop legumes. Plants in the Fabaceae family can be found on all the continents, excluding *Antarctica*, and thus have a widespread importance in agriculture across the globe. Besides food, plants in the Fabaceae family can be used to produce natural gums, dyes, and ornamentals.

The Solanaceae plant family includes a large number of agricultural crops, medicinal plants, spices, and ornamentals in its over 2,500 species. Taxonomically classified in the Plantae kingdom, Tracheobionta (subkingdom), Spermatophyta (superdivision), Magnoliophyta (division), Manoliopsida (class), Asteridae (subclass), and Solanales (order), the Solanaceae family includes, but is not limited to, potatoes, tomatoes, eggplants, various peppers, tobacco, and petunias. Plants in the Solanaceae can be found on all the continents, excluding *Antarctica*, and thus have a widespread importance in agriculture across the globe.

The Poaceae plant family supplies food, building materials, and feedstock for fuel processing. Taxonomically classified in the Plantae kingdom, Tracheobionta (subkingdom), Spermatophyta (superdivision), Magnoliophyta (division), Liliopsida (class), Commelinidae (subclass), and Cyperales (order), the Poaceae family includes, but is not limited to, flowering plants, grasses, and cereal crops such as barely, corn, lemongrass, millet, oat, rye, rice, wheat, sugarcane, and sorghum. Types of turf grass found in Arizona include, but are not limited to, hybrid Bermuda grasses (e.g., 328 tifgm, 419 tifway, tif sport).

The Rosaceae plant family includes flowering plants, herbs, shrubs, and trees. Taxonomically classified in the Plantae kingdom, Tracheobionta (subkingdom), Spermatophyta (superdivision), Magnoliophyta (division), Magnoliopsida (class), Rosidae (subclass), and Rosales (order), the Rosaceae family includes, but is not limited to, almond, apple, apricot, blackberry, cherry, nectarine, peach, plum, raspberry, strawberry, and quince.

The Vitaceae plant family includes flowering plants and vines. Taxonomically classified in the Plantae kingdom, Tracheobionta (subkingdom), Spermatophyta (superdivision), Magnoliophyta (division), Magnoliopsida (class), Rosidae (subclass), and Rhammales (order), the Vitaceae family includes, but is not limited to, grapes.

Particularly important to plant production is the beginning stage of growth where the plant emerges and matures into establishment. A method of treating a seed, seedling, or plant to directly improve the germination, emergence, and maturation of the plant; or to indirectly enhance the microbial soil community surrounding the seed or seedling is therefore valuable in starting the plant on the path to marketable production. The standard typically used for assessing emergence is the achievement of the hypocotyl stage, where a stem is visibly protruding from the soil. The standard typically used for assessing maturation is the achievement of the cotyledon stage, where two leaves visibly form on the emerged stem.

Also important in the production of fruit from plants is the yield and quality of fruit, which can be expressed in terms of, for example, the number, weight, color, firmness, ripeness, moisture, degree of insect infestation, degree of disease or rot, and/or degree of sunburn of the fruit. A method of treating a plant to directly improve the characteristics of the plant, or to indirectly enhance the biochemistry of the plant for photosynthetic capabilities and health of the plant's leaves, roots, and shoot to enable robust production of fruit is therefore valuable in increasing the efficiency of marketable production. Marketable and unmarketable designations can apply to both the plant and fruit, and can be defined differently based on the end use of the product, such as but not limited to, fresh market produce and processing for inclusion as an ingredient in a composition. The marketable determination can assess such qualities as, but not limited to, color, insect damage, blossom end rot, softness, and sunburn. The term total production can incorporate both marketable and unmarketable plants and fruit. The ratio of marketable plants or fruit to unmarketable plants or fruit can be referred to as utilization and expressed as a percentage. The utilization can be used as an indicator of the efficiency of the agricultural process as it shows the successful production of marketable plants or fruit, which will obtain the highest financial return for the grower, whereas total production will not necessarily provide such an indication. In addition, improvements in and measures of plant health can include plant resistance to stress. Stresses can be abiotic, such as, for example, temperature stress (high temperature as well as frost), salt stress, heavy-metal stress, water stress (whether drought or overwatering), and the like. Likewise, stresses can be biotic, such as, for example, stresses caused by fungi, bacteria, insects, weeds, viruses, and the like. Measures of improved plant health can be qualitative or quantitative. When quantitative, embodiments of improvement in plant health can be a relative improvement in any characteristic as compared to an untreated plant, wherein the improvement is at least 1%, 2%, 3%, 4%, 5%, 10%, 15%, 20%, 25%, 30%, 40%, 50%, 60%, 70%, 80%, 90%, 100%, 150%, 200%, 250%, 300%, 400%, 500%, 750%, 1000%, or more.

To achieve such improvements in health, emergence, maturation, yield, and quality of plants, embodiments of the invention provide microalgae-based compositions, methods of preparing liquid microalgae-based compositions, and methods of applying the microalgae-based compositions to plants. The microalgae of the liquid composition can comprise *Chlorella* sp. cultured in mixotrophic conditions, which comprises a culture medium primarily comprised of water with trace nutrients (e.g., nitrates, phosphates, vitamins, metals found in BG-11 recipe (available from UTEX The Culture Collection of Algae at the University of Texas at Austin, Austin, Texas)), light as an energy source for photosynthesis, organic carbon (e.g., acetate, acetic acid) as both an energy source and a source of carbon. In some embodiments, the *Chlorella* can be cultured in non-axenic mixotrophic conditions in the presence of contaminating organisms, such as but not limited to bacteria. Methods of culturing such microalgae in non-axenic mixotrophic conditions can be found in WO2014/074769A2 (Ganuza, et al.), hereby incorporated by reference.

In one non-limiting example of mixotrophic culturing of *Chlorella* for the described method of preparation of a composition for application to plants, the *Chlorella* is cultured in a BG-11 culture media or media derived from BG-11 culture media (e.g., in which additional component(s) are added to the media and/or one or more elements of the media is increased by 5%, 10%, 15%, 20%, 25%, 33%, 50%, or more over unmodified BG-11 media) for a culture length of 7-14 days in an open culturing vessel. The temperature can range from 20-30° C. and the pH from 6.5-8.5. The dissolved oxygen concentration can range from 0.1-4 mg/L. The culture receives acetic acid or acetate as a source of organic carbon supplying both carbon and an energy source to the *Chlorella* cells, and is supplied to the culture in a feed with a concentration in the range of 10-90% by a pH auxostat system. The culture receives natural sunlight (comprising photosynthetically active radiation) as source of energy. Mixing is provided by air sparging through aerotube, and fluid propulsion by thrusters submerged in the liquid culture.

By artificially controlling aspects of the *Chlorella* culturing process such as the organic carbon feed, oxygen levels, pH, and light, the culturing process differs from the culturing process that *Chlorella* experiences in nature. In addition to controlling various aspects of the culturing process, intervention by human operators or automated systems occurs during the non-axenic mixotrophic culturing of *Chlorella* through contamination control methods to prevent the *Chlorella* from being overrun and outcompeted by contaminating organisms (e.g., fungi, bacteria). Contamination control methods for microalgae cultures are known in the art and such suitable contamination control methods for non-axenic mixotrophic microalgae cultures are disclosed in WO2014/074769A2 (Ganuza, et al.), hereby incorporated by reference. By intervening in the microalgae culturing process, the impact of the contaminating microorganisms can be mitigated by suppressing the proliferation of containing organism populations and the effect on the microalgal cells (e.g., lysing, infection, death, clumping). Thus, through artificial control of aspects of the culturing process and intervening in the culturing process with contamination control methods, the *Chlorella* culture produced as a whole and used in the described inventive compositions differs from the culture that results from a *Chlorella* culturing process that occurs in nature.

In the alternative, the method of culturing *Chlorella* mixotrophically can comprise other known sources of organic carbon or combinations of organic carbon sources, such as: ammonium linoleate, arabinose, arginine, aspartic acid, butyric acid, cellulose, citric acid, ethanol, fructose, fatty acids, galactose, glucose, glycerol, glycine, lactic acid, lactose, maleic acid, maltose, mannose, methanol, molasses, peptone, plant based hydrolyzate, proline, propionic acid, ribose, sacchrose, partial or complete hydrolysates of starch, sucrose, tartaric, TCA-cycle organic acids, thin stillage, urea, industrial waste solutions, and yeast extract; as well as other known methods of mixing, methods of organic carbon supply, lighting, culture media, nutrient stocks, culturing vessels, and optimization of the culture parameters such as but not limited to temperature, pH, dissolved oxygen, and dissolved carbon dioxide. The mixotrophic *Chlorella* culture can be harvested from the culturing vessel and/or concentrated by means known in the art, such as, but not limited to, settling, centrifugation, filtration, and electro-dewatering to form the mixotrophic *Chlorella*-based composition that is used in the final product composition.

During the mixotrophic culturing process the *Chlorella* culture can also comprise cell debris and compounds excreted from the *Chlorella* cells into the culture medium. The output of the *Chlorella* mixotrophic culturing process provides the active ingredient for a composition that is applied to plants for improving at least one plant performance characteristic such as, for example, emergence, maturation, yield, quality, and the like. Typically, the composition is applied without separate addition to or supplementation of the composition with other active ingredients not found in the mixotrophic *Chlorella* whole cells and accompanying culture medium from the mixotrophic culturing process such as, but not limited to: non-*Chlorella* microalgae cells, microalgae extracts, macroalgae, macroalgae extracts, liquid fertilizers, granular fertilizers, mineral complexes (e.g., calcium, sodium, zinc, manganese, cobalt, silicon), fungi, bacteria, nematodes, protozoa, digestate solids, chemicals (e.g., ethanolamine, borax, boric acid), humic acid, nitrogen and nitrogen derivatives, phosphorus rock, pesticides, herbicides, insecticides, enzymes, plant fiber (e.g., coconut fiber); however, in some embodiments the augmentation of the base composition with any of the foregoing is contemplated. In the alternative, the mixotrophic *Chlorella*-based composition can be supplemented with nitrogen, phosphorus, or potassium to increase the levels within the composition to at least 1% of the total composition (i.e., addition of N, P, or K to increase levels at least 1-0-0, 0-1-0, 0-0-1, or combinations thereof). In some embodiments, the supplemented nutrient is not uptaken, chelated, or absorbed by the microalgae.

Mixotrophic *Chlorella* is the dominant microalgae species in the liquid composition. In some embodiments, the microalgae population of the liquid composition is substantially mixotrophic *Chlorella*. In some embodiments, mixotrophic or non-mixotrophic *Chlorella* comprises at least 90% of the microalgae population of the liquid composition. In some embodiments, mixotrophic or non-mixotrophic *Chlorella* comprises at least 91% of the microalgae population of the liquid composition. In some embodiments, mixotrophic or non-mixotrophic *Chlorella* comprises at least 92% of the microalgae population of the liquid composition. In some embodiments, mixotrophic or non-mixotrophic *Chlorella* comprises at least 93% of the microalgae population of the liquid composition. In some embodiments, mixotrophic or non-mixotrophic *Chlorella* comprises at least 94% of the microalgae population of the liquid composition. In some embodiments, mixotrophic or non-mixotrophic *Chlorella* comprises at least 95% of the microalgae population of the liquid composition. In some embodiments, mixotrophic or non-mixotrophic *Chlorella* comprises at least 96% of the microalgae population of the liquid composition. In some embodiments, mixotrophic or non-mixotrophic *Chlorella* comprises at least 97% of the microalgae population of the liquid composition. In some embodiments, mixotrophic or non-mixotrophic *Chlorella* comprises at least 98% of the microalgae population of the liquid composition. In some embodiments, mixotrophic or non-mixotrophic *Chlorella* comprises at least 99% of the microalgae population of the liquid composition. Liquid compositions having at least 99% of a *Chlorella* microalgae strain (e.g., at least 99.3%, at least 99.5%, or even at least 99.9%), such as mixotrophic *Chlorella*, can be considered to have a single algal species in the liquid composition. In one aspect, the liquid composition lacks any detectable amount of any other microalgae species. In another aspect, the liquid composition lacks any amount of any other microorganism (e.g., bacteria) in the liquid composition other than the desired *Chlorella* microalgae that is above 1% of the composition by weight.

The mixotrophic *Chlorella* resulting from the culturing stage consists of whole cells with the proximate analysis shown in Table 1, fatty acid profile shown in Table 2, and results of further analysis shown in Examples 1-3. The nutrient profile (i.e., proximate analysis) of the mixotrophic *Chlorella* cells before and after pasteurization, as well as during subsequent storage, was found to have little variance in most embodiments.

TABLE 1

|  | Range |
| --- | --- |
| Moisture & Volatiles | 1-2% |
| Ash Content | 3-4.5% |
| Carbohydrates (calculated) | 30-36% |
| % Protein (Leco) | 15-45% |
| % Lipids (AOAC) | 5-20% |

TABLE 2

| Analyte | Range (%) |
| --- | --- |
| C16 Palmitic Acid | 0.1-4 |
| C18:1n9c Oleic acid (Omega-9) | 0.1-2 |
| C18:2n6c Linoleic acid (Omega-6) | 0.1-5 |
| C18:3n3 Alpha-Linoleic acid (Omega-3) | 0.1-2 |
| Other | 0.1-4 |
| Total | 0.5-17 |

The mixotrophic *Chlorella* cells can also contain detectable levels of phytohormones, such as but not limited to: abscisic acid and metabolites, which are known to be related to the stomal apparatus function, growth inhibition, and seed dormancy; cytokinins, which are known to be related to cell division, bud development, development of the leaf blade, and senescence retardation; auxins, which are known to be related to elongation growth, differentiation of phloem elements, apical dominance, tropism, and initial root formation; and gibberellins, which are known to be related to stem elongation and initiation of seed germination.

In some embodiments, the mixotrophic *Chlorella* can comprise abscisic acid and abscisic acid metabolites in a range of 5-45 ng/g dry weight (DW). In some embodiments, the mixotrophic *Chlorella* can comprise cytokinins in a range of 60-300 ng/g dry weight (DW). In some embodiments, the mixotrophic *Chlorella* can comprise auxins in a range of 400-815 ng/g dry weight (DW). In some embodiments, the mixotrophic *Chlorella* can comprise gibberellins in a range of 0.1-15 ng/g dry weight (DW). In some embodiments, the mixotrophic *Chlorella* can comprise specific phytohormones in the ranges shown in Table 3.

In some embodiments, the mixotrophic *Chlorella* can comprise abscisic acid and abscisic acid metabolites in a range of 0.1-1 ng/g fresh weight (FW). In some embodiments, the mixotrophic *Chlorella* can comprise cytokinins in a range of 10-30 ng/g fresh weight (FW). In some embodiments, the mixotrophic *Chlorella* can comprise auxins in a range of 1-30 ng/g fresh weight (FW). In some embodiments, the mixotrophic *Chlorella* can comprise gibberellins in a range of 0.1-1 ng/g fresh weight (FW).

TABLE 3

| Metabolite | Range (ng/g DW) |
| --- | --- |
| cis-Abscisic acid | 0.1-13 |
| Abscisic acid glucose ester | 0.1-5 |
| Phaseic acid | 0.1-9 |
| Neo-Phaseic acid | 0.1-5 |
| trans-Abscisic acid | 0.1-8 |
| (trans) Zeatin | 0.1-5 |
| (cis) Zeatin | 0.1-16 |
| (trans) Zeatin riboside | 4-20 |
| (cis) Zeatin riboside | 30-250 |
| Dihydrozeatin riboside | 0.1-2 |
| Isopentenyladenine | 0.1-8 |
| Isopentenyladenosine | 1-15 |
| Indole-3-acetic acid | 400-815 |
| N-(Indole-3-yl-acetyl)-alanine | 0.1-5 |
| gibberellin 3 | 0.1-5 |
| gibberellin 34 | 0.1-5 |
| gibberellin 44 | 0.1-5 |

After harvest of the mixotrophic *Chlorella* composition from the culturing vessel, the mixotrophic *Chlorella*-based composition is typically incorporated in a liquid composition for application to plants. Generally, the liquid composition is stabilized by heating and cooling in a pasteurization process, adjustment of pH, and the addition of an inhibitor of yeast and mold growth.

In some embodiments, the mixotrophic *Chlorella* can be previously frozen and thawed before inclusion in the liquid composition. In some embodiments, the mixotrophic *Chlorella* has not been subjected to a previous freezing or thawing process. In some embodiments, the mixotrophic *Chlorella* whole cells have not been subjected to a drying process. In some embodiments, the cell walls of the mixotrophic *Chlorella* of the composition have not been lysed or disrupted, and the mixotrophic *Chlorella* cells have not been subjected to an extraction process or process that pulverizes the cells. The mixotrophic *Chlorella* whole cells typically are not subjected to a purification process for isolating the mixotrophic *Chlorella* whole cells from the accompanying constituents of the culturing process (e.g., trace nutrients, residual organic carbon, bacteria, cell debris, cell excretions), and thus the whole output from the mixotrophic *Chlorella* culturing process comprising whole *Chlorella* cells, culture medium, cell excretions, cell debris, bacteria, residual organic carbon, and trace nutrients, is used in the liquid composition for application to plants. In some embodiments, the mixotrophic *Chlorella* whole cells and the accompanying constituents of the culturing process are concentrated in the composition. In some embodiments, the mixotrophic *Chlorella* whole cells and the accompanying constituents of the culturing process are diluted in the composition to a low concentration. The mixotrophic *Chlorella* whole cells of the composition typically are not fossilized. In some embodiments, the mixotrophic *Chlorella* whole cells typically are not maintained in a viable state in the composition for continued growth after the method of using the composition in a soil or foliar application. In some embodiments, the mixotrophic *Chlorella* base composition can be biologically inactive after the composition is prepared. In some embodiments, the mixotrophic *Chlorella* base composition can be substantially biologically inactive after the composition is prepared. In some embodiments, the mixotrophic *Chlorella* base composition can increase in biological activity after the prepared composition is exposed to air.

In one non-limiting example of preparing the liquid composition with the mixotrophic *Chlorella*-based composition for application to plants, the mixotrophic *Chlorella*-based composition harvested from the culturing system is first held in a harvest tank before centrifuging the culture. Once the mixotrophic *Chlorella* culture is centrifuged, the centrifuge discharges the fraction rich in mixotrophic *Chlorella* whole cell solids, but also containing the accompanying constituents from the culture medium, into a container at a temperature of about 30° C. The mixotrophic *Chlorella*-based composition can continue (i.e., fresh) in the process of preparing the liquid composition or be stored in a freezer and thawed at a later time (i.e., stored) for processing into the liquid composition. When the mixotrophic *Chlorella*-based composition is stored in a freezer, the storage temperature is about −10° C. and it takes about 1-2 days for the composition to freeze. Once removed from the freezer, the stored mixotrophic *Chlorella*-based composition is placed outside to thaw for about 7 days. The fresh or stored mixotrophic *Chlorella*-based composition is then placed in a tank and heated to a temperature of about 60° C. for about 2 hours to begin the pasteurization process. The mixotrophic *Chlorella*-based composition is then diluted to a whole cell solids concentration of about 10-11% by weight and cooled to about 40° C. to complete the pasteurization process. The pH of the mixotrophic *Chlorella*-based composition is then adjusted to a pH of about 4 by mixing in an effective amount of phosphoric acid for stabilization purposes. About 0.3% potassium sorbate is then mixed with the mixotrophic *Chlorella*-based composition for stabilization purposes. The resulting liquid composition is then transferred to containers of a desired size stored at 3-5° C. until shipped.

While a similar process for preparing a liquid composition with the mixotrophically cultured *Chlorella* for application to plants can be performed with an additional step of drying the microalgae after centrifugation, the inventors surprisingly found that liquid compositions containing microalgae that was not dried produced better effects when applied to plants. Such effects found by the inventors to be increased when the mixotrophic *Chlorella* was not dried comprised: accelerated germination, chlorophyll content, and shoot weight. The inventors also found that the subjecting the mixotrophic *Chlorella* to a drum drying process lowered the detectable levels of phytohormones in the microalgae biomass.

While separate active ingredients are not added to or supplemented in the mixotrophic *Chlorella*-based composition, the liquid composition comprising the mixotrophic *Chlorella* whole cells and accompanying constituents from the culturing medium and process (e.g., trace nutrients, residual organic carbon, bacteria, cell debris, cell excretions) can be stabilized by heating and cooling in a pasteurization process. As shown in the Examples, the inventors found that the active ingredients of the mixotrophic *Chlorella*-based composition maintained effectiveness in improving plant germination, emergence, maturation, and growth when applied to plants after being subjected to the heating and cooling of a pasteurization process and also observed various performance enhancements arising from pasteurization as compared to a non-pasteurized version of the formulation.

Figure 2:
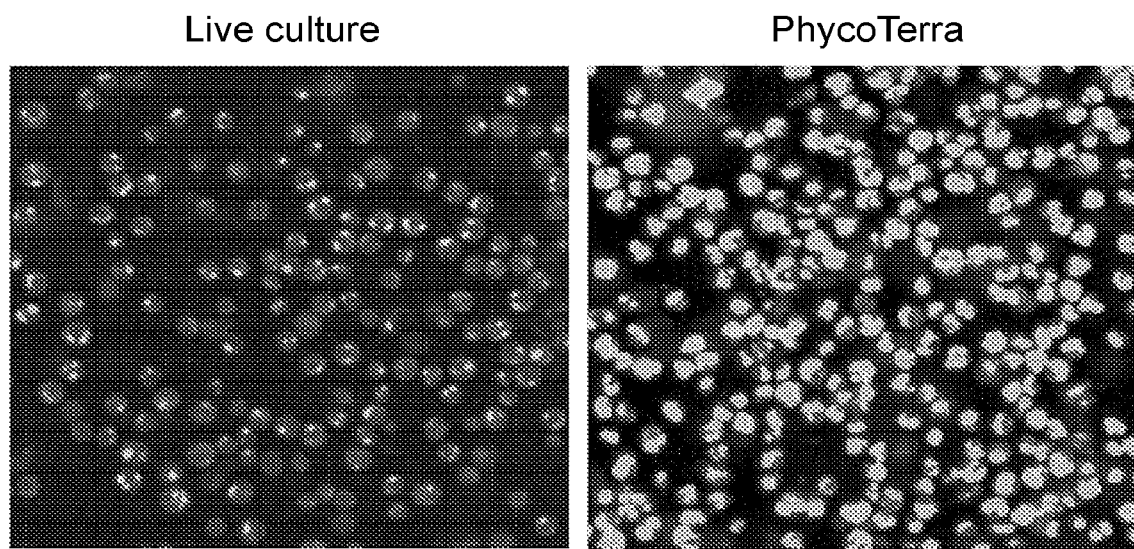
FIG. 2 depicts the results of a test for the condition of cell membrane of *Chlorella* cells after pasteurization (propidium iodine).

While the mixotrophic *Chlorella* cells are intact and viable (i.e., physically fit to live, capable of further growth or cell division) after being harvested from the culture, the *Chlorella* cells resulting from the pasteurization process were confirmed to have intact cell walls but were not viable. Mixotrophic *Chlorella* cells resulting from the pasteurization process were observed under a microscope to determine the condition of the cell walls after the being subjected to the heating and cooling of the process, and was visually confirmed that the *Chlorella* cell walls were intact and not broken open. For further investigation of the condition of the cell, a culture of live mixotrophic *Chlorella* cells and the mixotrophic *Chlorella* cells resulting from the pasteurization process were subjected to propidium iodide, an exclusion fluorescent dye that labels DNA if the cell membrane is compromised, and visually compared under a microscope. The propidium iodide comparison showed that the *Chlorella* cells resulting from the pasteurization process contained a high amount of dyed DNA, resulting in the conclusion that the mixotrophic *Chlorella* cell walls were intact, but the cell membranes were compromised (FIG. 2). Thus, the permeability of the pasteurized *Chlorella* cells differs from the permeability of a *Chlorella* cell with both an intact cell wall and cell membrane.

Additionally, a culture of live mixotrophic *Chlorella* cells and the mixotrophic *Chlorella* cells resulting from the pasteurization process were subjected to DAPI (4',6-diamidino-2-phyenylindole)-DNA binding fluorescent dye and visually compared under a microscope. The DAPI-DNA binding dye comparison showed that the *Chlorella* cells resulting from the pasteurization process contained a greatly diminished amount of viable DNA in the cells, indicating that the mixotrophic *Chlorella* cells are not viable after pasteurization (FIG. 1). The two DNA dying comparisons demonstrate that the pasteurization process transformed the structure and function of the *Chlorella* cells from the natural state by changing: the cells from viable to non-viable, the condition of the cell membrane, and the permeability of the cells.

In some embodiments, the microalgae-based composition can be heated to a temperature in the range of 50-90° C. In some embodiments, the microalgae-based composition can be heated to a temperature in the range of 55-65° C. In some embodiments, the microalgae-based composition can be heated to a temperature in the range of 58-62° C. In some embodiments, the microalgae-based composition can be heated to a temperature in the range of 50-60° C. In some embodiments, the microalgae-based composition can be heated to a temperature in the range of 60-70° C. In some embodiments, the microalgae-based composition can be heated to a temperature in the range of 70-80° C. In some embodiments, the microalgae-based composition can be heated to a temperature in the range of 80-90° C.

In some embodiments, the microalgae-based composition can be heated for a time period in the range of 90-150 minutes. In some embodiments, the microalgae-based composition can be heated for a time period in the range of 110-130 minutes. In some embodiments, the microalgae-based composition can be heated for a time period in the range of 90-100 minutes. In some embodiments, the microalgae-based composition can be heated for a time period in the range of 100-110 minutes. In some embodiments, the microalgae-based composition can be heated for a time period in the range of 110-120 minutes. In some embodiments, the microalgae-based composition can be heated for a time period in the range of 120-130 minutes. In some embodiments, the microalgae-based composition can be heated for a time period in the range of 130-140 minutes. In some embodiments, the microalgae-based composition can be heated for a time period in the range of 140-150 minutes.

In some embodiments, the microalgae-based composition can be heated for a time period in the range of 15-360 minutes. In some embodiments, the microalgae-based composition can be heated for a time period in the range of 15-30 minutes. In some embodiments, the microalgae-based composition can be heated for a time period in the range of 30-60 minutes. In some embodiments, the microalgae-based composition can be heated for a time period in the range of 60-120 minutes. In some embodiments, the microalgae-based composition can be heated for a time period in the range of 120-180 minutes. In some embodiments, the microalgae-based composition can be heated for a time period in the range of 180-360 minutes.

In some embodiments, the microalgae-based composition can be cooled to a temperature in the range of 35-45° C. In some embodiments, the microalgae-based composition can be cooled to a temperature in the range of 36-44° C. In some embodiments, the microalgae-based composition can be cooled to a temperature in the range of 37-43° C. In some embodiments, the microalgae-based composition can be cooled to a temperature in the range of 38-42° C. In some embodiments, the microalgae-based composition can be cooled to a temperature in the range of 39-41° C. In some embodiments, the microalgae-based composition can be cooled to a temperature suitable for further processing or handling.

In some embodiments, a method of preparing a low concentration mixotrophic *Chlorella*-based liquid composition for application to plants can comprise: culturing *Chlorella* in an liquid culture medium and mixotrophic conditions comprising utilization of an organic carbon source and photosynthetically active radiation as energy sources in a culturing vessel; harvesting the mixotrophic *Chlorella* culture from the culturing vessel; and mixing the mixotrophic *Chlorella* culture with an acid and a yeast and mold inhibitor to form a composition with a concentration of an effective amount of the mixotrophic *Chlorella*-based composition for application to a plant for enhanced characteristics, wherein the whole mixotrophic *Chlorella* cells have not been subjected to a drying process.

In some embodiments, a method of preparing a mixotrophic *Chlorella*-based liquid composition for application to plants can comprise: heating a composition comprising whole microalgae cells in an liquid medium at a temperature in the range of 50-70° C.; adjusting concentration of the whole cells in the heated composition to a concentration in the range of 5-30% whole microalgae cells by weight; cooling the composition to a temperature in the range of 35-45° C.; adjusting the pH of the composition to a pH in the range of 3-5; and contacting the composition with a yeast and mold inhibitor.

In some embodiments, the composition can comprise 5-30% solids by weight of whole mixotrophic *Chlorella* cells. In some embodiments, the composition can comprise 5-20% solids by weight of whole mixotrophic *Chlorella* cells. In some embodiments, the composition can comprise 5-15% solids by weight of whole mixotrophic *Chlorella* cells. In some embodiments, the composition can comprise 5-10% solids by weight of whole mixotrophic *Chlorella* cells. In some embodiments, the composition can comprise 10-20% solids by weight of whole mixotrophic *Chlorella* cells. In some embodiments, the composition can comprise 10-20% solids by weight of whole mixotrophic *Chlorella* cells. In some embodiments, the composition can comprise 20-30% solids by weight of whole mixotrophic *Chlorella* cells. In some embodiments, further dilution of the whole mixotrophic *Chlorella* cells percent solids by weight can be occur before application for low concentration applications of the composition.

The composition can be diluted to a lower concentration for an effective amount in a soil or foliar application by mixing a volume of the composition in a volume of water. The percent solids of mixotrophic *Chlorella* whole cells resulting in the diluted composition can be calculated by multiplying the original percent solids of mixotrophic *Chlorella* whole cells in the composition by the ratio of the volume of the composition to the volume of water.

In some embodiments, the composition can comprise less than 1% solids by weight of whole mixotrophic *Chlorella* cells. In some embodiments, the composition can comprise less than 0.9% solids by weight of whole mixotrophic *Chlorella* cells. In some embodiments, the composition can comprise less than 0.8% solids by weight of whole mixotrophic *Chlorella* cells. In some embodiments, the composition can comprise less than 0.7% solids by weight of whole mixotrophic *Chlorella* cells. In some embodiments, the composition can comprise less than 0.6% solids by weight of whole mixotrophic *Chlorella* cells. In some embodiments, the composition can comprise less than 0.5% solids by weight of whole mixotrophic *Chlorella* cells. In some embodiments, the composition can comprise less than 0.4% solids by weight of whole mixotrophic *Chlorella* cells. In some embodiments, the composition can comprise less than 0.3% solids by weight of whole mixotrophic *Chlorella* cells. In some embodiments, the composition can comprise less than 0.2% solids by weight of whole mixotrophic *Chlorella* cells. In some embodiments, the composition can comprise less than 0.1% solids by weight of whole mixotrophic *Chlorella* cells. In some embodiments, the effective amount in an application of the liquid composition for enhanced germination, emergence, or maturation of a plant can comprise a concentration of solids of mixotrophic *Chlorella* whole cells in the range of 0.002642-0.079252% (e.g., about 0.003% to about 0.080%), equivalent to a diluted concentration of 2-10 mL/gallon of a solution with an original percent solids of mixotrophic *Chlorella* whole cells in the range of 5-30%.

In some embodiments, the effective amount in an application of the liquid composition can comprise a concentration in the range of 1-50 mL/gallon, resulting in a reduction of the percent solids of mixotrophic *Chlorella* whole cells from 5-30% to 0.001321-0.396258% (e.g., about 0.001% to about 0.400%). In some embodiments, the effective amount in an application of the liquid composition can comprise a concentration in the range of 1-10 mL/gallon, resulting in a reduction of the percent solids of mixotrophic *Chlorella* whole cells from 5-30% to 0.001321-0.079252% (e.g., about 0.001% to about 0.080%). In some embodiments, the effective amount in an application of the liquid composition can comprise a concentration in the range of 2-7 mL/gallon, resulting in a reduction of the percent solids of mixotrophic *Chlorella* whole cells from 5-30% to 0.002642-0.055476% (e.g., about 0.003% to about 0.055%). In some embodiments, the effective amount in an application of the liquid composition can comprise a concentration in the range of 10-20 mL/gallon, resulting in a reduction of the percent solids of mixotrophic *Chlorella* whole cells from 5-30% to 0.013201-0.158503% (e.g., about 0.013% to about 0.160%). In some embodiments, the effective amount in an application of the liquid composition can comprise a concentration in the range of 20-30 mL/gallon, resulting in a reduction of the percent solids of mixotrophic *Chlorella* whole cells from 5-30% to 0.026417-0.237755% (e.g., about 0.025% to about 0.250%). In some embodiments, the effective amount in an application of the liquid composition can comprise a concentration in the range of 30-45 mL/gallon, resulting in a reduction of the percent solids of mixotrophic *Chlorella* whole cells from 5-30% to 0.039626-0.356631% (e.g., about 0.040% to about 0.360%). In some embodiments, the effective amount in an application of the liquid composition can comprise a concentration in the range of 30-40 mL/gallon, resulting in a reduction of the percent solids of mixotrophic *Chlorella* whole cells from 5-30% to 0.039626-0.317007% (e.g., about 0.040% to about 0.320%). In some embodiments, the effective amount in an application of the liquid composition can comprise a concentration in the range of 40-50 mL/gallon, resulting in a reduction of the percent solids of mixotrophic *Chlorella* whole cells from 5-30% to 0.052834-0.396258% (e.g., about 0.055% to about 0.400%).

In some embodiments, the liquid composition can comprise low concentrations of bacteria contributing to the solids percentage of the composition in addition to the whole mixotrophic *Chlorella* cells. Examples of bacteria found in non-axenic mixotrophic conditions can be found in WO2014/074769A2 (Ganuza et al.), hereby incorporated by reference. A live bacteria count can be determined using methods known in the art such as plate counts, plate counts using Petrifilm available from 3M (St. Paul, Minnesota), spectrophotometric (turbidimetric) measurements, visual comparison of turbidity with a known standard, direct cell counts under a microscope, cell mass determination, and measurement of cellular activity. Live bacteria counts in a non-axenic mixotrophic microalgae culture can range from $10^4$ to $10^9$ CFU/mL, and can depend on contamination control measures taken during the culturing of the microalgae. The level of bacteria in the composition can be determined by an aerobic plate count which quantifies aerobic colony forming units (CFU) in a designated volume. In some embodiments, the composition comprises an aerobic plate count of 40,000-400,000 CFU/mL. In some embodiments, the composition comprises an aerobic plate count of 40,000-100,000 CFU/mL. In some embodiments, the composition comprises an aerobic plate count of 100,000-200,000 CFU/mL. In some embodiments, the composition comprises an aerobic plate count of 200,000-300,000 CFU/mL. In some embodiments, the composition comprises an aerobic plate count of 300,000-400,000 CFU/mL.

Using QPCR (quantitative polymerase chain reaction) to analyze the bacteria population in a mixotrophic *Chlorella* culture before pasteurization and after pasteurization, it was observed that the profile of bacteria in the culture changes after pasteurization. Particularly, the post-pasteurization profile of bacteria includes a higher proportion of spore forming bacteria and includes, but is not limited to, *Paenibacillus* sp., *Bacillus* sp., *Lactobacillus* sp., and *Brevibacillus* sp as the dominant types of bacteria. Comparing the aerobic plate counts of a mixotrophic *Chlorella* culture before pasteurization and after pasteurization, it was also observed that the total number of bacteria in the culture is lower after pasteurization. Combinations of temperature and time for the pasteurization process for the times of 15, 30, 60, 120, 180, and 360 minutes, and 50, 60, 70, 80, and 90° C. were tested with a culture of mixotrophic *Chlorella*, and the resulting aerobic plate counts ranged from $7.58 \times 10^6$ CFU to as low as $1.74 \times 10^3$ CFU. Storage temperature was also shown to vary the profile of bacteria of a pasteurized culture of mixotrophic *Chlorella*, with samples stored at temperatures of 2-4° C., 25° C., and 40° C. varying in the aerobic plate count numbers and type of dominant bacteria species over time.

In some embodiments, the pH of the microalgae-based composition can be adjusted downward to a pH in the range of 3-5. In some embodiments, the pH of the microalgae-based composition can be adjusted upward to a pH in the range of 3-5. In some embodiments, the pH of the microalgae-based composition can be adjusted to a pH in the range of 3.5-4.5. In some embodiments, the pH of the microalgae-based composition can be adjusted to a pH in the range of 3-3.5. In some embodiments, the pH of the microalgae-based composition can be adjusted to a pH in the range of 3.5-4. In some embodiments, the pH of the microalgae-based composition can be adjusted to a pH in the range of 4-4.5. In some embodiments, the pH of the microalgae-based composition can be adjusted to a pH in the range of 4.5-5.

In some embodiments, stabilizing means that are not active regarding the improvement of plant germination, emergence, and maturation, but instead aid in stabilizing the microalgae-based composition can be added to prevent the proliferation of unwanted microorganisms (e.g., yeast, mold) and prolong shelf life. Such inactive but stabilizing means can comprise an acid, and a yeast and mold inhibitor. In some embodiments, the stabilizing means are suitable for plants and do not inhibit the growth or health of the plant. In the alternative, the stabilizing means can contribute to nutritional properties of the liquid composition, such as but not limited to, the levels of nitrogen, phosphorus, or potassium.

In some embodiments, the step of adjusting the pH of the composition comprises contacting the composition with stabilizing means comprising an acid. In some embodiments, such an acid can comprise phosphoric acid ($H_3PO_4$). In some embodiments, the amount of acid needed to adjust the pH can comprise different amounts of acid depending on the starting pH of the microalgae composition, which can vary based on culturing conditions of the microalgae, residual concentrations of organic carbon or other nutrients, and previous processing of the composition. In some embodiments, the microalgae-based composition can comprise less than 0.3% phosphoric acid. In some embodiments, the microalgae-based composition can comprise 0.01-0.3% phosphoric acid. In some embodiments, the microalgae-based composition can comprise 0.05-0.25% phosphoric acid. In some embodiments, the microalgae-based composition can comprise 0.01-0.1% phosphoric acid. In some embodiments, the microalgae-based composition can comprise 0.1-0.2% phosphoric acid. In some embodiments, the microalgae-based composition can comprise 0.2-0.3% phosphoric acid.

In some embodiments, the yeast and mold inhibitor can comprise potassium sorbate ($C_6H_7KO_2$). In some embodiments, the composition can comprise less than 0.5% potassium sorbate. In some embodiments, the composition can comprise 0.01-0.5% potassium sorbate. In some embodiments, the composition can comprise 0.05-0.4% potassium sorbate. In some embodiments, the composition can comprise 0.01-0.1% potassium sorbate. In some embodiments, the composition can comprise 0.1-0.2% potassium sorbate. In some embodiments, the composition can comprise 0.2-0.3% potassium sorbate. In some embodiments, the composition can comprise 0.3-0.4% potassium sorbate. In some embodiments, the composition can comprise 0.4-0.5% potassium sorbate. In other embodiments, the stabilizing function of potassium sorbate and/or phosphoric acid can be achieved with use of comparable additives with similar function such as, for example, ascorbic acid, sodium benzoate, or the like, in quantities/concentrations similar to those listed herein for potassium sorbate and phosphoric acid.

The microalgae-based composition is a liquid and is substantially comprised of water. In some embodiments, the composition can comprise 70-95% water. In some embodiments, the composition can comprise 85-95% water. In some embodiments, the composition can comprise 70-75% water. In some embodiments, the composition can comprise 75-80% water. In some embodiments, the composition can comprise 80-85% water. In some embodiments, the composition can comprise 85-90% water. In some embodiments, the composition can comprise 90-95% water. The liquid nature and high-water content of the microalgae-based composition facilitates administration of the composition in a variety of manners, such as, but not limited to: flowing through an irrigation system, flowing through an above ground drip irrigation system, flowing through a buried drip irrigation system, flowing through a central pivot irrigation system, sprayers, sprinklers, water cans, and the like.

The microalgae-based composition can be used immediately after formulation or can be stored in containers for later use. In some embodiments, the microalgae-based composition can be stored out of direct sunlight. In some embodiments, the microalgae-based composition can be refrigerated. In some embodiments, the microalgae-based composition can be stored at 1-10° C. In some embodiments, the microalgae-based composition can be stored at 1-3° C. In some embodiments, the microalgae-based composition can be stored at 3-5° C. In some embodiments, the microalgae-based composition can be stored at 5-8° C. In some embodiments, the composition can be stored at 8-10° C.

In some embodiments, not drying the mixotrophic *Chlorella*-based composition during preparation can increase seed emergence by 40-4,000%, or more, for soil applications. In some embodiments, not drying the mixotrophic *Chlorella*-based composition during preparation can increase chlorophyll content by 10-30% for foliar applications. In some embodiments, not drying the mixotrophic *Chlorella*-based composition during preparation can increase whole plant weight emergence by 10-20% for foliar applications. In some embodiments, not drying the mixotrophic *Chlorella*-based composition during preparation can increase shoot weight by 20-30% for foliar applications.

Administration of the mixotrophic *Chlorella*-based liquid composition treatment to a seed or plant can be in an amount effective to produce an enhanced characteristic in the plant compared to a substantially identical population of untreated plant. Such enhanced characteristics can comprise accelerated seed germination, accelerated seedling emergence, improved seedling emergence, improved leaf formation, accelerated leaf formation, improved plant maturation, accelerated plant maturation, increased plant yield, increased plant growth, increased plant quality, increased plant health, increased fruit yield, increased fruit growth, and increased fruit quality. Non-limiting examples of such enhanced characteristics can comprise accelerated achievement of the hypocotyl stage, accelerated protrusion of a stem from the soil, accelerated achievement of the cotyledon stage, accelerated leaf formation, increased marketable plant weight, increased marketable plant yield, increased marketable fruit weight, increased production plant weight, increased production fruit weight, increased utilization (indicator of efficiency in the agricultural process based on ratio of marketable fruit to unmarketable fruit), increased chlorophyll content (indicator of plant health), increased plant weight (indicator of plant health), increased root weight (indicator of plant health), and increased shoot weight (indicator of plant health). Such enhanced characteristics can occur individually in a plant, or in combinations of multiple enhanced characteristics.

Surprisingly, the inventors found that administration of the described mixotrophic *Chlorella*-based composition in low concentration applications was effective in producing enhanced characteristics in plants. In some embodiments, the mixotrophic *Chlorella*-based liquid composition treatment is administered before the seed is planted. In some embodiments, the mixotrophic *Chlorella*-based liquid composition treatment is administered at the time the seed is planted. In some embodiments, the mixotrophic *Chlorella*-based liquid composition treatment is administered after the seed is planted, including, for example, at various post-emergence growth and maturation stages of the plant.

In some embodiments, administration of the mixotrophic *Chlorella*-based liquid composition can increase the number of plants emerged by 20-160%, or more, compared to a substantially identical population of untreated seeds or plants. In some embodiments, administration of the mixotrophic *Chlorella*-based liquid composition can increase the number of plants emerged by at least 20% compared to a substantially identical population of untreated seeds or plants. In some embodiments, administration of the mixotrophic *Chlorella*-based liquid composition can increase the number of plants emerged by at least 40% compared to a substantially identical population of untreated seeds or plants. In some embodiments, administration of the mixotrophic *Chlorella*-based liquid composition can increase the number of plants emerged by at least 60% compared to a substantially identical population of untreated seeds or plants. In some embodiments, administration of the mixotrophic *Chlorella*-based liquid composition can increase the number of plants emerged by at least 80% compared to a substantially identical population of untreated seeds or plants. In some embodiments, administration of the mixotrophic *Chlorella*-based liquid composition can increase the number of plants emerged by at least 100% compared to a substantially identical population of untreated seeds or plants. In some embodiments, administration of the mixotrophic *Chlorella*-based liquid composition can increase the number of plants emerged by at least 120% compared to a substantially identical population of untreated seeds or plants. In some embodiments, administration of the mixotrophic *Chlorella*-based liquid composition can increase the number of plants emerged by at least 140% compared to a substantially identical population of untreated seeds or plants. In some embodiments, administration of the mixotrophic *Chlorella*-based liquid composition can increase the number of plants emerged by at least 150% compared to a substantially identical population of untreated seeds or plants.

In some embodiments, administration of the mixotrophic *Chlorella*-based liquid composition can increase the number of plants emerged by 25-2000%, or more, compared to a substantially identical population of untreated seeds of plants. In some embodiments, administration of the mixotrophic *Chlorella*-based liquid composition can increase the number of plants emerged by at least 25% compared to a substantially identical population of untreated seeds of plants. In some embodiments, administration of the mixotrophic *Chlorella*-based liquid composition can increase the number of plants emerged by at least 30% compared to a substantially identical population of untreated seeds of plants. In some embodiments, administration of the mixotrophic *Chlorella*-based liquid composition can increase the number of plants emerged by at least 40% compared to a substantially identical population of untreated seeds of plants. In some embodiments, administration of the mixotrophic *Chlorella*-based liquid composition can increase the number of plants emerged by at least 50% compared to a substantially identical population of untreated seeds of plants. In some embodiments, administration of the mixotrophic *Chlorella*-based liquid composition can increase the number of plants emerged by at least 60% compared to a substantially identical population of untreated seeds of plants. In some embodiments, administration of the mixotrophic *Chlorella*-based liquid composition can increase the number of plants emerged by at least 70% compared to a substantially identical population of untreated seeds of plants. In some embodiments, administration of the mixotrophic *Chlorella*-based liquid composition can increase the number of plants emerged by at least 80% compared to a substantially identical population of untreated seeds of plants. In some embodiments, administration of the mixotrophic *Chlorella*-based liquid composition can increase the number of plants emerged by at least 90% compared to a substantially identical population of untreated seeds of plants.

In some embodiments, administration of the mixotrophic *Chlorella*-based liquid composition can increase the number of plants emerged by at least 100% compared to a substantially identical population of untreated seeds of plants. In some embodiments, administration of the mixotrophic *Chlorella*-based liquid composition can increase the number of plants emerged by at least 200% compared to a substantially identical population of untreated seeds of plants. In some embodiments, administration of the mixotrophic *Chlorella*-based liquid composition can increase the number of plants emerged by at least 300% compared to a substantially identical population of untreated seeds of plants. In some embodiments, administration of the mixotrophic *Chlorella*-based liquid composition can increase the number of plants emerged by at least 400% compared to a substantially identical population of untreated seeds of plants. In some embodiments, administration of the mixotrophic *Chlorella*-based liquid composition can increase the number of plants emerged by at least 500% compared to a substantially identical population of untreated seeds of plants. In some embodiments, administration of the mixotrophic *Chlorella*-based liquid composition can increase the number of plants emerged by at least 600% compared to a substantially identical population of untreated seeds of plants. In some embodiments, administration of the mixotrophic *Chlorella*-based liquid composition can increase the number of plants emerged by at least 700% compared to a substantially identical population of untreated seeds of plants. In some embodiments, administration of the mixotrophic *Chlorella*-based liquid composition can increase the number of plants emerged by at least 800% compared to a substantially identical population of untreated seeds of plants. In some embodiments, administration of the mixotrophic *Chlorella*-based liquid composition can increase the number of plants emerged by at least 900% compared to a substantially identical population of untreated seeds of plants. In some embodiments, administration of the mixotrophic *Chlorella*-based liquid composition can increase the number of plants emerged by at least 1,000% compared to a substantially identical population of untreated seeds of plants. In some embodiments, administration of the mixotrophic *Chlorella*-based liquid composition can increase the number of plants emerged by at least 1,500% compared to a substantially identical population of untreated seeds of plants.

In some embodiments, administration of the mixotrophic *Chlorella*-based liquid composition can increase the number of plants demonstrating maturation by leaf formation by 30-180%, or more, compared to a substantially identical population of untreated seeds or plants. In some embodiments, administration of the mixotrophic *Chlorella*-based liquid composition can increase the number plants demonstrating maturation by leaf formation by at least 30% compared to a substantially identical population of untreated seeds or plants. In some embodiments, administration of the mixotrophic *Chlorella*-based liquid composition can increase the number plants demonstrating maturation by leaf formation by at least 50% compared to a substantially identical population of untreated seeds or plants. In some embodiments, administration of the mixotrophic *Chlorella*-based liquid composition can increase the number plants demonstrating maturation by leaf formation by at least 70% compared to a substantially identical population of untreated seeds or plants. In some embodiments, administration of the mixotrophic *Chlorella*-based liquid composition can increase the number plants demonstrating maturation by leaf formation by at least 90% compared to a substantially identical population of untreated seeds or plants. In some embodiments, administration of the mixotrophic *Chlorella*-based liquid composition can increase the number plants demonstrating maturation by leaf formation by at least 110% compared to a substantially identical population of untreated seeds or plants. In some embodiments, administration of the mixotrophic *Chlorella*-based liquid composition can increase the number plants demonstrating maturation by leaf formation by at least 130% compared to a substantially identical population of untreated seeds or plants. In some embodiments, administration of the mixotrophic *Chlorella*-based liquid composition can increase the number plants demonstrating maturation by leaf formation by at least 150% compared to a substantially identical population of untreated seeds or plants. In some embodiments, administration of the mixotrophic *Chlorella*-based liquid composition can increase the number plants demonstrating maturation by leaf formation by at least 160% compared to a substantially identical population of untreated seeds or plants. In some embodiments, administration of the mixotrophic *Chlorella*-based liquid composition can increase the number plants demonstrating maturation by leaf formation by at least 170% compared to a substantially identical population of untreated seeds or plants.

In some embodiments, administration of the mixotrophic *Chlorella*-based liquid composition can increase the number of plants demonstrating maturation by leaf formation by 20-350%, or more, compared to a substantially identical population of untreated seeds of plants. In some embodiments, administration of the mixotrophic *Chlorella*-based liquid composition can increase the number plants demonstrating maturation by leaf formation by at least 20% compared to a substantially identical population of untreated seeds of plants. In some embodiments, administration of the mixotrophic *Chlorella*-based liquid composition can increase the number plants demonstrating maturation by leaf formation by at least 30% compared to a substantially identical population of untreated seeds of plants. In some embodiments, administration of the mixotrophic *Chlorella*-based liquid composition can increase the number plants demonstrating maturation by leaf formation by at least 40% compared to a substantially identical population of untreated seeds of plants. In some embodiments, administration of the mixotrophic *Chlorella*-based liquid composition can increase the number plants demonstrating maturation by leaf formation by at least 50% compared to a substantially identical population of untreated seeds of plants. In some embodiments, administration of the mixotrophic *Chlorella*-based liquid composition can increase the number plants demonstrating maturation by leaf formation by at least 60% compared to a substantially identical population of untreated seeds of plants. In some embodiments, administration of the mixotrophic *Chlorella*-based liquid composition can increase the number plants demonstrating maturation by leaf formation by at least 70% compared to a substantially identical population of untreated seeds of plants. In some embodiments, administration of the mixotrophic *Chlorella*-based liquid composition can increase the number plants demonstrating maturation by leaf formation by at least 80% compared to a substantially identical population of untreated seeds of plants. In some embodiments, administration of the mixotrophic *Chlorella*-based liquid composition can increase the number plants demonstrating maturation by leaf formation by at least 90% compared to a substantially identical population of untreated seeds of plants.

In some embodiments, administration of the mixotrophic *Chlorella*-based liquid composition can increase the number of plants demonstrating maturation by leaf formation by at least 100% compared to a substantially identical population of untreated seeds of plants. In some embodiments, administration of the mixotrophic *Chlorella*-based liquid composition can increase the number plants demonstrating maturation by leaf formation by at least 150% compared to a substantially identical population of untreated seeds of plants. In some embodiments, administration of the mixotrophic *Chlorella*-based liquid composition can increase the number plants demonstrating maturation by leaf formation by at least 200% compared to a substantially identical population of untreated seeds of plants. In some embodiments, administration of the mixotrophic *Chlorella*-based liquid composition can increase the number plants demonstrating maturation by leaf formation by at least 250% compared to a substantially identical population of untreated seeds of plants. In some embodiments, administration of the mixotrophic *Chlorella*-based liquid composition can increase the number plants demonstrating maturation by leaf formation by at least 300% compared to a substantially identical population of untreated seeds of plants.

In some embodiments, the administration of the mixotrophic *Chlorella*-based liquid composition can increase utilization by 80-100% compared to a substantially identical population of untreated plants. In some embodiments, administration of the mixotrophic *Chlorella*-based liquid composition can increase utilization by at least 80% compared to a substantially identical population of untreated plants. In some embodiments, administration of the mixotrophic *Chlorella*-based liquid composition can increase utilization by at least 85% compared to a substantially identical population of untreated plants. In some embodiments, administration of the mixotrophic *Chlorella*-based liquid composition can increase utilization by at least 90% compared to a substantially identical population of untreated plants. In some embodiments, administration of the mixotrophic *Chlorella*-based liquid composition can increase utilization by at least 95% compared to a substantially identical population of untreated plants.

In some embodiments, the administration of the mixotrophic *Chlorella*-based liquid composition can increase marketable plant weight by 200-290%, or more, compared to a substantially identical population of untreated plants. In some embodiments, administration of the mixotrophic *Chlorella*-based liquid composition can increase the marketable plant weight by at least 200% compared to a substantially identical population of untreated plants. In some embodiments, administration of the mixotrophic *Chlorella*-based liquid composition can increase the marketable plant weight by at least 210% compared to a substantially identical population of untreated plants. In some embodiments, administration of the mixotrophic *Chlorella*-based liquid composition can increase the marketable plant weight by at least 220% compared to a substantially identical population of untreated plants. In some embodiments administration of the mixotrophic *Chlorella*-based liquid composition can increase the marketable plant weight by at least 230% compared to a substantially identical population of untreated plants. In some embodiments administration of the mixotrophic *Chlorella*-based liquid composition can increase the marketable plant weight by at least 240% compared to a substantially identical population of untreated plants. In some embodiments, administration of the mixotrophic *Chlorella*-based liquid composition can increase the marketable plant weight by at least 250% compared a substantially identical population of untreated plants. In some embodiments, administration of the mixotrophic *Chlorella*-based liquid composition can increase the marketable plant weight by at least 260% compared to a substantially identical population of untreated plants. In some embodiments, administration of the mixotrophic *Chlorella*-based liquid composition can increase the marketable plant weight by at least 270% compared to a substantially identical population of untreated plants. In some embodiments, administration of the mixotrophic *Chlorella*-based liquid composition can increase the marketable plant weight by at least 280% compared to a substantially identical population of untreated plants.

In some embodiments, the administration of the mixotrophic *Chlorella*-based liquid composition can increase marketable plant yield by 150-230%, or more, compared to a substantially identical population of untreated plants. In some embodiments, administration of the mixotrophic *Chlorella*-based liquid composition can increase the marketable plant yield by at least 150% compared to a substantially identical population of untreated plants. In some embodiments, administration of the mixotrophic *Chlorella*-based liquid composition can increase the marketable plant yield by at least 180% compared to a substantially identical population of untreated plants. In some embodiments, administration of the mixotrophic *Chlorella*-based liquid composition can increase the marketable plant yield by at least 190% compared to a substantially identical population of untreated plants. In some embodiments, administration of the mixotrophic *Chlorella*-based liquid composition can increase the marketable plant yield by at least 200% compared to a substantially identical population of untreated plants. In some embodiments, administration of the mixotrophic *Chlorella*-based liquid composition can increase the marketable plant yield by at least 210% compared to a substantially identical population of untreated plants. In some embodiments, administration of the mixotrophic *Chlorella*-based liquid composition can increase the marketable plant yield by at least 220% compared to a substantially identical population of untreated plants.

In some embodiments, the administration of the mixotrophic *Chlorella*-based liquid composition can increase marketable fruit weight by 10-50%, or more, compared to a substantially identical population of untreated plants. In some embodiments, administration of the mixotrophic *Chlorella*-based liquid composition can increase the marketable fruit weight by at least 10% compared to a substantially identical population of untreated plants. In some embodiments, administration of the mixotrophic *Chlorella*-based liquid composition can increase the marketable fruit weight by at least 20% compared to a substantially identical population of untreated plants. In some embodiments, administration of the mixotrophic *Chlorella*-based liquid composition can increase the marketable fruit weight by at least 30% compared to a substantially identical population of untreated plants. In some embodiments, administration of the mixotrophic *Chlorella*-based liquid composition can increase the marketable fruit weight by at least 40% compared to a substantially identical population of untreated plants. In some embodiments, administration of the mixotrophic *Chlorella*-based liquid composition can increase the marketable fruit weight by at least 45% compared to a substantially identical population of untreated plants.

In some embodiments, the administration of the mixotrophic *Chlorella*-based liquid composition can increase production plant weight by 70-120%, or more, compared to a substantially identical population of untreated plants. In some embodiments, administration of the mixotrophic *Chlorella*-based liquid composition can increase production plant weight by at least 70% compared to a substantially identical population of untreated plants. In some embodiments, administration of the mixotrophic *Chlorella*-based liquid composition can increase the production plant weight by at least 80% compared to a substantially identical population of untreated plants. In some embodiments, administration of the mixotrophic *Chlorella*-based liquid composition can increase the production plant weight by at least 90% compared to a substantially identical population of untreated plants. In some embodiments, administration of the mixotrophic *Chlorella*-based liquid composition can increase the production plant weight by at least 100% compared to a substantially identical population of untreated plants. In some embodiments, administration of the mixotrophic *Chlorella*-based liquid composition can increase the production plant weight by at least 110% compared to a substantially identical population of untreated plants.

In some embodiments, the administration of the mixotrophic *Chlorella*-based liquid composition can increase production fruit weight by 70-110%, or more, compared to a substantially identical population of untreated plants. In some embodiments, administration of the mixotrophic *Chlorella*-based liquid composition can increase production fruit weight by at least 70% compared to a substantially identical population of untreated plants. In some embodiments, administration of the mixotrophic *Chlorella*-based liquid composition can increase the production fruit weight by at least 80% compared to a substantially identical population of untreated plants. In some embodiments, administration of the mixotrophic *Chlorella*-based liquid composition can increase the production fruit weight by at least 90% compared to a substantially identical population of untreated plants. In some embodiments, administration of the mixotrophic *Chlorella*-based liquid composition can increase the production fruit weight by at least 100% compared to a substantially identical population of untreated plants. In some embodiments, administration of the mixotrophic *Chlorella*-based liquid composition can increase the production fruit weight by at least 105% compared to a substantially identical population of untreated plants.

In some embodiments, the administration of the mixotrophic *Chlorella*-based liquid composition can increase the chlorophyll content by 15-40%, or more, compared to a substantially identical population of untreated plants. In some embodiments, administration of the mixotrophic *Chlorella*-based liquid composition can increase the chlorophyll content by at least 15% compared to a substantially identical population of untreated plants. In some embodiments, administration of the mixotrophic *Chlorella*-based liquid composition can increase the chlorophyll content by at least 20% compared to a substantially identical population of untreated plants. In some embodiments, administration of the mixotrophic *Chlorella*-based liquid composition can increase the chlorophyll content by at least 25% compared to a substantially identical population of untreated plants. In some embodiments, administration of the mixotrophic *Chlorella*-based liquid composition can increase the chlorophyll content by at least 30% compared to a substantially identical population of untreated plants.

In some embodiments, the administration of the mixotrophic *Chlorella*-based liquid composition can increase the whole plant weight by 30-60%, or more, compared to a substantially identical population of untreated plants. In some embodiments, administration of the mixotrophic *Chlorella*-based liquid composition can increase the whole plant weight by at least 30% compared to a substantially identical population of untreated plants. In some embodiments, administration of the mixotrophic *Chlorella*-based liquid composition can increase the whole plant weight by at least 35% compared to a substantially identical population of untreated plants. In some embodiments, administration of the mixotrophic *Chlorella*-based liquid composition can increase the whole plant weight by at least 40% compared to a substantially identical population of untreated plants. In some embodiments, administration of the mixotrophic *Chlorella*-based liquid composition can increase the whole plant weight by at least 45% compared to a substantially identical population of untreated plants. In some embodiments, administration of the mixotrophic *Chlorella*-based liquid composition can increase the whole plant weight by at least 50% compared to a substantially identical population of untreated plants. In some embodiments, administration of the mixotrophic *Chlorella*-based liquid composition can increase the whole plant weight by at least 55% compared to a substantially identical population of untreated plants.

In some embodiments, the administration of the mixotrophic *Chlorella*-based liquid composition can increase the root weight by 30-60%, or more, compared to a substantially identical population of untreated plants. In some embodiments, administration of the mixotrophic *Chlorella*-based liquid composition can increase the root weight by at least 30% compared to a substantially identical population of untreated plants. In some embodiments, administration of the mixotrophic *Chlorella*-based liquid composition can increase the root weight by at least 35% compared to a substantially identical population of untreated plants. In some embodiments, administration of the mixotrophic *Chlorella*-based liquid composition can increase the root weight by at least 40% compared to a substantially identical population of untreated plants. In some embodiments, administration of the mixotrophic *Chlorella*-based liquid composition can increase the root weight by at least 45% compared to a substantially identical population of untreated plants. In some embodiments, administration of the mixotrophic *Chlorella*-based liquid composition can increase the root weight by at least 50% compared to a substantially identical population of untreated plants.

In some embodiments, the administration of the mixotrophic *Chlorella*-based liquid composition can increase the shoot weight by 30-70%, or more, compared to a substantially identical population of untreated plants. In some embodiments, administration of the mixotrophic *Chlorella*-based liquid composition can increase the shoot weight by at least 30% compared to a substantially identical population of untreated plants. In some embodiments, administration of the mixotrophic *Chlorella*-based liquid composition can increase the shoot weight by at least 35% compared to a substantially identical population of untreated plants. In some embodiments, administration of the mixotrophic *Chlorella*-based liquid composition can increase the shoot weight by at least 40% compared to a substantially identical population of untreated plants. In some embodiments, administration of the mixotrophic *Chlorella*-based liquid composition can increase the shoot weight by at least 45% compared to a substantially identical population of untreated plants. In some embodiments, administration of the mixotrophic *Chlorella*-based liquid composition can increase the shoot weight by at least 50% compared a substantially identical population of untreated plants. In some embodiments, administration of the mixotrophic *Chlorella*-based liquid composition can increase the shoot weight by at least 55% compared to a substantially identical population of untreated plants. In some embodiments, administration of the mixotrophic *Chlorella*-based liquid composition can increase the shoot weight by at least 60% compared to a substantially identical population of untreated plants.

Whether in a seed soak, capillary action, soil, or foliar application the method of use comprises relatively low concentrations of the mixotrophic *Chlorella*-based liquid composition. Even at such low concentrations, the described composition has been shown to be effective at producing an enhanced characteristic in plants. The ability to use low concentrations allows for a reduced impact on the environment that can result from over application and an increased efficiency in the method of use of the liquid composition by requiring a small amount of material to produce the desired effect. In some embodiments, the use of the mixotrophic *Chlorella*-based liquid composition with a low volume irrigation system in soil applications allows the low concentration of the liquid composition to remain effective and not be diluted to a point where the composition is no longer in at a concentration capable of producing the desired effect on the plants while also increasing the grower's water use efficiency. The ability to use low concentrations of mixotrophic *Chlorella* whole cells and lack of purification processes to isolate the cells also reduces the dewatering and processing needs of the microalgae which can be produced at low concentrations in the culturing stage, and thus increasing the energy efficiency in the method of preparing the product.

In conjunction with the low concentrations of mixotrophic *Chlorella* whole cells solids in the liquid composition necessary to be effective for enhancing the described characteristics of plants, the liquid composition can does not have be to be administered continuously or at a high frequency (e.g., multiple times per day, daily). The ability of the mixotrophic *Chlorella*-based liquid composition to be effective at low concentrations and a low frequency of application was an unexpected result, due to the traditional thinking that as the concentration of active ingredients decreases the frequency of application should increase to provide adequate amounts of the active ingredients. Effectiveness at low concentration and application frequency increases the material usage efficiency of the method of using the liquid composition while also increasing the yield efficiency of the agricultural process. The use a composition of mixotrophic *Chlorella* whole cells that does not require processing to dry, extract, lyse, or otherwise disrupt the cell wall also increases energy efficiency in the method of preparing the product and allows the product to be produced in a quicker time frame.

Seed Soak Application

In one non-limiting embodiment, the administration of the mixotrophic *Chlorella*-based liquid composition treatment can comprise soaking the seed in an effective amount of the liquid composition before planting the seed. In some embodiments, the administration of the mixotrophic *Chlorella*-based liquid composition further comprises removing the seed from the liquid composition after soaking and drying the seed before planting. In some embodiments, the seed can be soaked in the mixotrophic *Chlorella*-based liquid composition for a time period in the range of 90-150 minutes. In some embodiments, the seed can be soaked in the mixotrophic *Chlorella*-based liquid composition for a time period in the range of 110-130 minutes. In some embodiments, the seed can be soaked in the mixotrophic *Chlorella*-based liquid composition for a time period in the range of 90-100 minutes. In some embodiments, the seed can be soaked in the mixotrophic *Chlorella*-based liquid composition for a time period in the range of 100-110 minutes. In some embodiments, the seed can be soaked in the mixotrophic *Chlorella*-based liquid composition for a time period in the range of 110-120 minutes. In some embodiments, the seed can be soaked in the mixotrophic *Chlorella*-based liquid composition for a time period in the range of 120-130 minutes. In some embodiments, the seed can be soaked in the mixotrophic *Chlorella*-based liquid composition for a time period in the range of 130-140 minutes. In some embodiments, the seed can be soaked in the mixotrophic *Chlorella*-based liquid composition for a time period in the range of 140-150 minutes.

The composition can be diluted to a lower concentration for an effective amount in a seed soak application by mixing a volume of the mixotrophic *Chlorella*-based composition in a volume of water. The percent solids of mixotrophic *Chlorella* whole cells resulting in the diluted composition can be calculated by multiplying the original percent solids in the composition by the ratio of the volume of the composition to the volume of water. In some embodiments, the effective amount in a seed soak application of the mixotrophic *Chlorella*-based liquid composition can comprise a concentration in the range of 6-10 mL/gallon, resulting in a reduction of the percent solids of mixotrophic *Chlorella* whole cells from 5-30% to 0.007925-0.079252% (e.g., about 0.008% to about 0.080%). In some embodiments, the effective amount in a seed soak application of the mixotrophic *Chlorella*-based liquid composition can comprise a concentration in the range of 7-9 mL/gallon, resulting in a reduction of the percent solids of mixotrophic *Chlorella* whole cells from 5-30% to 0.009245-0.071327% (e.g., about 0.009% to about 0.070%). In some embodiments, the effective amount in a seed soak application of the mixotrophic *Chlorella*-based liquid composition can comprise a concentration in the range of 6-7 mL/gallon, resulting in a reduction of the percent solids of mixotrophic *Chlorella* whole cells from 5-30% to 0.007925-0.05547% (e.g., about 0.008% to about 0.055%). In some embodiments, the effective amount in a seed soak application of the mixotrophic *Chlorella*-based liquid composition can comprise a concentration in the range of 7-8 mL/gallon, resulting in a reduction of the percent solids of mixotrophic *Chlorella* whole cells from 5-30% to 0.009246-0.063401% (e.g., about 0.009% to about 0.065%). In some embodiments, the effective amount in a seed soak application of the mixotrophic *Chlorella*-based liquid composition can comprise a concentration in the range of 8-9 mL/gallon, resulting in a reduction of the percent solids of mixotrophic *Chlorella* whole cells from 5-30% to 0.010567-0.071327% (e.g., about 0.010% to about 0.070%). In some embodiments, the effective amount in a seed soak application of the mixotrophic *Chlorella*-based liquid composition can comprise a concentration in the range of 9-10 mL/gallon, resulting in a reduction of the percent solids of mixotrophic *Chlorella* whole cells from 5-30% to 0.011888-0.079252% (e.g., about 0.012% to about 0.080%).

Soil Application

In another non-limiting embodiment, the administration of the mixotrophic *Chlorella*-based liquid composition treatment can comprise contacting the soil in the immediate vicinity of the planted seed or plant with an effective amount of the liquid composition. In some embodiments, the mixotrophic *Chlorella*-based liquid composition can be supplied to the soil by injection into a low volume irrigation system, such as but not limited to a drip irrigation system supplying water beneath the soil through perforated conduits or at the soil level by fluid conduits hanging above the ground or protruding from the ground. In some embodiments, the mixotrophic *Chlorella*-based liquid composition can be supplied to the soil by a soil drench method wherein the liquid composition is poured on the soil.

The mixotrophic *Chlorella*-based composition can be diluted to a lower concentration for an effective amount in a soil application by mixing a volume of the composition in a volume of water. The percent solids of mixotrophic *Chlorella* whole cells resulting in the diluted composition can be calculated by multiplying the original percent solids in the composition by the ratio of the volume of the composition to the volume of water. In some embodiments, the effective amount in a soil application of the mixotrophic *Chlorella*-based liquid composition can comprise a concentration in the range of 3.5-10 mL/gallon, resulting in a reduction of the percent solids of mixotrophic *Chlorella* whole cells from 5-30% to 0.004623-0.079252% (e.g., about 0.004% to about 0.080%). In some embodiments, the effective amount in a soil application of the mixotrophic *Chlorella*-based liquid composition can comprise a concentration in the range of 3.5-4 mL/gallon, resulting in a reduction of the percent solids of mixotrophic *Chlorella* whole cells from 5-30% to 0.004623-0.031701% (e.g., about 0.004% to about 0.032%). In some embodiments, the effective amount in a soil application of the mixotrophic *Chlorella*-based liquid composition can comprise a concentration in the range of 4-5 mL/gallon, resulting in a reduction of the percent solids of mixotrophic *Chlorella* whole cells from 5-30% to 0.005283-0.039626% (e.g., about 0.005% to about 0.040%). In some embodiments, the effective amount in a soil application of the mixotrophic *Chlorella*-based liquid composition can comprise a concentration in the range of 5-6 mL/gallon, resulting in a reduction of the percent solids of mixotrophic *Chlorella* whole cells from 5-30% to 0.006604-0.047551% (e.g., about 0.006% to about 0.050%). In some embodiments, the effective amount in a soil application of the mixotrophic *Chlorella*-based liquid composition can comprise a concentration in the range of 6-7 mL/gallon, resulting in a reduction of the percent solids of mixotrophic *Chlorella* whole cells from 5-30% to 0.0.007925-

0.055476% (e.g., about 0.008% to about 0.055%). In some embodiments, the effective amount in a soil application of the mixotrophic *Chlorella*-based liquid composition can comprise a concentration in the range of 7-8 mL/gallon, resulting in a reduction of the percent solids of mixotrophic *Chlorella* whole cells from 5-30% to 0.009246-0.063401% (e.g., about 0.009% to about 0.065%). In some embodiments, the effective amount in a soil application of the mixotrophic *Chlorella*-based liquid composition can comprise a concentration in the range of 8-9 mL/gallon, resulting in a reduction of the percent solids of mixotrophic *Chlorella* whole cells from 5-30% to 0.010567-0.071327% (e.g., about 0.010% to about 0.075%). In some embodiments, the effective amount in a soil application of the mixotrophic *Chlorella*-based liquid composition can comprise a concentration in the range of 9-10 mL/gallon, resulting in a reduction of the percent solids of mixotrophic *Chlorella* whole cells from 5-30% to 0.011888-0.079252% (e.g., about 0.012% to about 0.080%).

In some embodiments, the effective amount in a soil application of the mixotrophic *Chlorella*-based liquid composition can comprise a concentration in the range of 1-50 mL/gallon, resulting in a reduction of the percent solids of mixotrophic *Chlorella* whole cells from 5-30% to 0.001321-0.396258% (e.g., about 0.001% to about 0.400%). In some embodiments, the effective amount in a soil application of the mixotrophic *Chlorella*-based liquid composition can comprise a concentration in the range of 1-10 mL/gallon, resulting in a reduction of the percent solids of mixotrophic *Chlorella* whole cells from 5-30% to 0.001321-0.079252% (e.g., about 0.001% to about 0.080%). In some embodiments, the effective amount in a soil application of the mixotrophic *Chlorella*-based liquid composition can comprise a concentration in the range of 2-7 mL/gallon, resulting in a reduction of the percent solids of mixotrophic *Chlorella* whole cells from 5-30% to 0.002642-0.055476% (e.g., about 0.003% to about 0.055%). In some embodiments, the effective amount in a soil application of the mixotrophic *Chlorella*-based liquid composition can comprise a concentration in the range of 10-20 mL/gallon, resulting in a reduction of the percent solids of mixotrophic *Chlorella* whole cells from 5-30% to 0.013201-0.158503% (e.g., about 0.013% to about 0.160%). In some embodiments, the effective amount in a soil application of the mixotrophic *Chlorella*-based liquid composition can comprise a concentration in the range of 20-30 mL/gallon, resulting in a reduction of the percent solids of mixotrophic *Chlorella* whole cells from 5-30% to 0.026417-0.237755% (e.g., about 0.025% to about 0.250%). In some embodiments, the effective amount in a soil application of the mixotrophic *Chlorella*-based liquid composition can comprise a concentration in the range of 30-45 mL/gallon, resulting in a reduction of the percent solids of mixotrophic *Chlorella* whole cells from 5-30% to 0.039626-0.356631% (e.g., about 0.040% to about 0.360%). In some embodiments, the effective amount in a soil application of the mixotrophic *Chlorella*-based liquid composition can comprise a concentration in the range of 30-40 mL/gallon, resulting in a reduction of the percent solids of mixotrophic *Chlorella* whole cells from 5-30% to 0.039626-0.317007% (e.g., about 0.040% to about 0.320%). In some embodiments, the effective amount in a soil application of the mixotrophic *Chlorella*-based liquid composition can comprise a concentration in the range of 40-50 mL/gallon, resulting in a reduction of the percent solids of mixotrophic *Chlorella* whole cells from 5-30% to 0.052834-0.396258% (e.g., about 0.055% to about 0.400%).

The rate of application of the mixotrophic *Chlorella*-based composition at the desired concentration can be expressed as a volume per area. In some embodiments, the rate of application of the mixotrophic *Chlorella*-based liquid composition in a soil application can comprise a rate in the range of 50-150 gallons/acre. In some embodiments, the rate of application of the mixotrophic *Chlorella*-based liquid composition in a soil application can comprise a rate in the range of 75-125 gallons/acre. In some embodiments, the rate of application of the mixotrophic *Chlorella*-based liquid composition in a soil application can comprise a rate in the range of 50-75 gallons/acre. In some embodiments, the rate of application of the mixotrophic *Chlorella*-based liquid composition in a soil application can comprise a rate in the range of 75-100 gallons/acre. In some embodiments, the rate of application of the mixotrophic *Chlorella*-based liquid composition in a soil application can comprise a rate in the range of 100-125 gallons/acre. In some embodiments, the rate of application of the mixotrophic *Chlorella*-based liquid composition in a soil application can comprise a rate in the range of 125-150 gallons/acre.

The frequency of the application of the mixotrophic *Chlorella*-based composition can be expressed as the number of applications per period of time (e.g., two applications per month), or by the period of time between applications (e.g., one application every 21 days). In some embodiments, the plant can be contacted by the mixotrophic *Chlorella*-based liquid composition in a soil application every 3-28 days. In some embodiments, the plant can be contacted by the liquid composition in a soil application every 4-10 days. In some embodiments, the plant can be contacted by the mixotrophic *Chlorella*-based liquid composition in a soil application every 18-24 days. In some embodiments, the plant can be contacted by the liquid composition in a soil application every 3-7 days. In some embodiments, the plant can be contacted by the mixotrophic *Chlorella*-based liquid composition in a soil application every 7-14 days. In some embodiments, the plant can be contacted by the mixotrophic *Chlorella*-based liquid composition in a soil application every 14-21 days. In some embodiments, the plant can be contacted by the mixotrophic *Chlorella*-based liquid composition in a soil application every 21-28 days.

Soil application(s) of the mixotrophic *Chlorella*-based composition generally begin after the plant has become established, but can begin before establishment, at defined time period after planting, or at a defined time period after emergence form the soil in some embodiments. In some embodiments, the plant can be first contacted by the mixotrophic *Chlorella*-based liquid composition in a soil application 5-14 days after the plant emerges from the soil. In some embodiments, the plant can be first contacted by the mixotrophic *Chlorella*-based liquid composition in a soil application 5-7 days after the plant emerges from the soil. In some embodiments, the plant can be first contacted by the mixotrophic *Chlorella*-based liquid composition in a soil application 7-10 days after the plant emerges from the soil. In some embodiments, the plant can be first contacted by the mixotrophic *Chlorella*-based liquid composition in a soil application 10-12 days after the plant emerges from the soil. In some embodiments, the plant can be first contacted by the mixotrophic *Chlorella*-based liquid composition in a soil application 12-14 days after the plant emerges from the soil.

Capillary Action Application

In another non-limiting embodiment, the administration of the mixotrophic *Chlorella*-based liquid composition treatment can comprise first soaking the seed in water, removing the seed from the water, drying the seed, applying an effective amount of the liquid composition below the seed planting level in the soil, and planting the seed, wherein the liquid composition supplied to the seed from below by capillary action. In some embodiments, the seed can be soaked in water for a time period in the range of 90-150 minutes. In some embodiments, the seed can be soaked in water for a time period in the range of 110-130 minutes. In some embodiments, the seed can be soaked in water for a time period in the range of 90-100 minutes. In some embodiments, the seed can be soaked in water for a time period in the range of 100-110 minutes. In some embodiments, the seed can be soaked in water for a time period in the range of 110-120 minutes. In some embodiments, the seed can be soaked in water for a time period in the range of 120-130 minutes. In some embodiments, the seed can be soaked in water for a time period in the range of 130-140 minutes. In some embodiments, the seed can be soaked in water for a time period in the range of 140-150 minutes.

The mixotrophic *Chlorella*-based composition can be diluted to a lower concentration for an effective amount in a capillary action application by mixing a volume of the composition in a volume of water. The percent solids of mixotrophic *Chlorella* whole cells resulting in the diluted composition can be calculated by multiplying the original percent solids in the composition by the ratio of the volume of the composition to the volume of water. In some embodiments, the effective amount in a capillary action application of the mixotrophic *Chlorella*-based liquid composition can comprise a concentration in the range of 6-10 mL/gallon, resulting in a reduction of the percent solids of mixotrophic *Chlorella* whole cells from 5-30% to 0.007925-0.079252% (e.g., about 0.008% to about 0.080%). In some embodiments, the effective amount in a capillary action application of the mixotrophic *Chlorella*-based liquid composition can comprise a concentration in the range of 7-9 mL/gallon, resulting in a reduction of the percent solids of mixotrophic *Chlorella* whole cells from 5-30% to 0.009245-0.071327% (e.g., about 0.009% to about 0.075%). In some embodiments, the effective amount in a capillary action application of the mixotrophic *Chlorella*-based liquid composition can comprise a concentration in the range of 6-7 mL/gallon, resulting in a reduction of the percent solids of mixotrophic *Chlorella* whole cells from 5-30% to 0.007925-0.05547% (e.g., about 0.008% to about 0.055%). In some embodiments, the effective amount in a capillary action application of the mixotrophic *Chlorella*-based liquid composition can comprise a concentration in the range of 7-8 mL/gallon, resulting in a reduction of the percent solids of mixotrophic *Chlorella* whole cells from 5-30% to 0.009246-0.063401% (e.g., about 0.009% to about 0.065%). In some embodiments, the effective amount in a capillary action application of the mixotrophic *Chlorella*-based liquid composition can comprise a concentration in the range of 8-9 mL/gallon, resulting in a reduction of the percent solids of mixotrophic *Chlorella* whole cells from 5-30% to 0.010567-0.071327% (e.g., about 0.010% to about 0.075%). In some embodiments, the effective amount in a capillary action application of the mixotrophic *Chlorella*-based liquid composition can comprise a concentration in the range of 9-10 mL/gallon, resulting in a reduction of the percent solids of mixotrophic *Chlorella* whole cells from 5-30% to 0.011888-0.079252% (e.g., about 0.012% to about 0.080%).

Foliar Application

In one non-limiting embodiment, the administration of the mixotrophic *Chlorella*-based liquid composition treatment can comprise contacting the foliage of the plant with an effective amount of the liquid composition. In some embodiments, the mixotrophic *Chlorella*-based liquid composition can be sprayed on the foliage by a hand sprayer, a sprayer on an agriculture implement, a sprinkler, a broad distribution system such as a crop duster, or the like.

The mixotrophic *Chlorella*-based composition can be diluted to a lower concentration for an effective amount in a foliar application by mixing a volume of the composition in a volume of water. The percent solids of mixotrophic *Chlorella* whole cells resulting in the diluted composition can be calculated by multiplying the original percent solids in the composition by the ratio of the volume of the composition to the volume of water. In some embodiments, the effective amount in a foliar application of the mixotrophic *Chlorella*-based liquid composition can comprise a concentration in the range of 2-10 mL/gallon, resulting in a reduction of the percent solids of mixotrophic *Chlorella* whole cells from 5-30% to 0.002642-0.079252% (e.g., about 0.003% to about 0.080%). In some embodiments, the effective amount in a foliar application of the mixotrophic *Chlorella*-based liquid composition can comprise a concentration in the range of 2-3 mL/gallon, resulting in a reduction of the percent solids of mixotrophic *Chlorella* whole cells from 5-30% to 0.002642-0.023775% (e.g., about 0.003% to about 0.025%). In some embodiments, the effective amount in a foliar application of the mixotrophic *Chlorella*-based liquid composition can comprise a concentration in the range of 3-4 mL/gallon, resulting in a reduction of the percent solids of mixotrophic *Chlorella* whole cells from 5-30% to 0.003963-0.031701% (e.g., about 0.004% to about 0.035%). In some embodiments, the effective amount in a foliar application of the mixotrophic *Chlorella*-based liquid composition can comprise a concentration in the range of 4-5 mL/gallon, resulting in a reduction of the percent solids of mixotrophic *Chlorella* whole cells from 5-30% to 0.005283-0.039626% (e.g., about 0.005% to about 0.040%). In some embodiments, the effective amount in a foliar application of the mixotrophic *Chlorella*-based liquid composition can comprise a concentration in the range of 5-6 mL/gallon, resulting in a reduction of the percent solids of mixotrophic *Chlorella* whole cells from 5-30% to 0.006604-0.047551% (e.g., about 0.007% to about 0.050%). In some embodiments, the effective amount in a foliar application of the mixotrophic *Chlorella*-based liquid composition can comprise a concentration in the range of 6-7 mL/gallon, resulting in a reduction of the percent solids of mixotrophic *Chlorella* whole cells from 5-30% to 0.007925-0.055476% (e.g., about 0.008% to about 0.055%). In some embodiments, the effective amount in a foliar application of the mixotrophic *Chlorella*-based liquid composition can comprise a concentration in the range of 7-8 mL/gallon, resulting in a reduction of the percent solids of mixotrophic *Chlorella* whole cells from 5-30% to 0.009246-0.063401% (e.g., about 0.009% to about 0.065%). In some embodiments, the effective amount in a foliar application of the mixotrophic *Chlorella*-based liquid composition can comprise a concentration in the range of 8-9 mL/gallon, resulting in a reduction of the percent solids of mixotrophic *Chlorella* whole cells from 5-30% to 0.010567-0.071327% (e.g., about 0.010% to about 0.070%). In some embodiments, the effective amount in a foliar application of the mixotrophic *Chlorella*-based liquid composition can comprise a concentration in the range of 9-10 mL/gallon, resulting in a reduction of the percent solids of mixotrophic *Chlorella* whole cells from 5-30% to 0.011888-0.079252% (e.g., about 0.012% to about 0.080%).

The rate of application of the mixotrophic *Chlorella*-based composition at the desired concentration can be expressed as a volume per area. In some embodiments, the rate of application of the mixotrophic *Chlorella*-based liquid composition in a foliar application can comprise a rate in the range of 10-50 gallons/acre. In some embodiments, the rate of application of the liquid composition in a foliar application can comprise a rate in the range of 10-15 gallons/acre. In some embodiments, the rate of application of the mixotrophic *Chlorella*-based liquid composition in a foliar application can comprise a rate in the range of 15-20 gallons/acre. In some embodiments, the rate of application of the mixotrophic *Chlorella*-based liquid composition in a foliar application can comprise a rate in the range of 20-25 gallons/acre. In some embodiments, the rate of application of the mixotrophic *Chlorella*-based liquid composition in a foliar application can comprise a rate in the range of 25-30 gallons/acre. In some embodiments, the rate of application of the mixotrophic *Chlorella*-based liquid composition in a foliar application can comprise a rate in the range of 30-35 gallons/acre. In some embodiments, the rate of application of the mixotrophic *Chlorella*-based liquid composition in a foliar application can comprise a rate in the range of 35-40 gallons/acre. In some embodiments, the rate of application of the mixotrophic *Chlorella*-based liquid composition in a foliar application can comprise a rate in the range of 40-45 gallons/acre. In some embodiments, the rate of application of the mixotrophic *Chlorella*-based liquid composition in a foliar application can comprise a rate in the range of 45-50 gallons/acre.

The frequency of the application of the mixotrophic *Chlorella*-based composition can be expressed as the number of applications per period of time (e.g., two applications per month), or by the period of time between applications (e.g., one application every 21 days). In some embodiments, the plant can be contacted by the mixotrophic *Chlorella*-based liquid composition in a foliar application every 3-28 days, or more. In some embodiments, the plant can be contacted by the mixotrophic *Chlorella*-based liquid composition in a foliar application every 4-10 days. In some embodiments, the plant can be contacted by the mixotrophic *Chlorella*-based liquid composition in a foliar application every 18-24 days. In some embodiments, the plant can be contacted by the mixotrophic *Chlorella*-based liquid composition in a foliar application every 3-7 days. In some embodiments, the plant can be contacted by the mixotrophic *Chlorella*-based liquid composition in a foliar application every 7-14 days. In some embodiments, the plant can be contacted by the mixotrophic *Chlorella*-based liquid composition in a foliar application every 14-21 days. In some embodiments, the plant can be contacted by the mixotrophic *Chlorella*-based liquid composition in a foliar application every 21-28 days.

Foliar application(s) of the mixotrophic *Chlorella*-based composition generally begin after the plant has become established, but can begin before establishment, at defined time period after planting, or at a defined time period after emergence form the soil in some embodiments. In some embodiments, the plant can be first contacted by the mixotrophic *Chlorella*-based liquid composition in a foliar application 5-14 days after the plant emerges from the soil. In some embodiments, the plant can be first contacted by the mixotrophic *Chlorella*-based liquid composition in a foliar application 5-7 days after the plant emerges from the soil. In some embodiments, the plant can be first contacted by the mixotrophic *Chlorella*-based liquid composition in a foliar application 7-10 days after the plant emerges from the soil. In some embodiments, the plant can be first contacted by the mixotrophic *Chlorella*-based liquid composition in a foliar application 10-12 days after the plant emerges from the soil. In some embodiments, the plant can be first contacted by the mixotrophic *Chlorella*-based liquid composition in a foliar application 12-14 days after the plant emerges from the soil.

Hydroponic Application

In another non-limiting embodiment, the administration of the mixotrophic *Chlorella*-based liquid composition to a seed or plant can comprise applying the composition in combination with a nutrient medium to seeds disposed in and plants growing in a hydroponic growth medium or an inert growth medium (e.g., coconut husks). The mixotrophic *Chlorella*-based liquid composition can be applied multiple times per day, per week, or per growing season.

EXAMPLES

Embodiments of the invention are exemplified, and additional embodiments are disclosed in further detail in the following Examples, which are not in any way intended to limit the scope of any aspect of the invention described herein.

Example 1

Samples of mixotrophically cultured *Chlorella* whole cells were analyzed for content. The results of the sample analysis and extrapolated ranges based on standard deviations are shown in Table 4, with NA indicating levels that were too low for detection. The results of the protein analysis are presented on a dry weight basis, while the remaining results are presented on a wet basis.

TABLE 4

| | Sample No. | | | | |
|---|---|---|---|---|---|
| | 1 | 2 | 3 | 4 | Range |
| % Protein (Leco) | 34.89 | 35.04 | 29.4 | 24.5 | 15-45 |
| % Lipids (AOAC) | 14.6 | 15.3 | 10.75 | 12.9 | 5-20 |
| Phosphorus (ppm) | 2000 | 2300 | 2700 | 2800 | 1,600-3,200 |
| Potassium (ppm) | 6208 | 6651 | 7088 | 8008 | 5,400-9,000 |
| Calcium (ppm) | 2100 | 2000 | 1500 | 1200 | 750-2,600 |
| Iron (ppm) | 130 | 160 | 140 | 110 | 80-200 |
| Magnesium (ppm) | 1500 | 1500 | 1200 | 970 | 700-1,800 |
| Manganese (ppm) | 31 | 32 | 25 | 21 | 10-40 |
| Zinc (ppm) | <25 | 29 | <25 | <25 | 0.1-40 |
| Arsenic (ppm) | <2.5 | <2.5 | <2.5 | <2.5 | 0.1-2.5 |
| Cadmium (ppm) | <0.5 | 1.8 | <0.5 | <0.5 | 0.1-2.0 |
| Cobalt (ppm) | 2.2 | 1.6 | 1.4 | 1.3 | 0.1-5.0 |
| Chromium (ppm) | NA | <1.0 | <1.0 | <1.0 | 0.1-1.0 |
| Copper (ppm) | NA | 180 | 18 | 14 | 1-300 |
| Mercury (ppm) | NA | <2.0 | <2.0 | <2.0 | 0.1-2.0 |
| Molybdenum (ppm) | NA | <2.5 | <2.5 | <2.5 | 0.1-2.5 |
| Sodium (ppm) | 2500 | 5400 | 3300 | 2400 | 1,000-6,800 |
| Nickel (ppm) | NA | <2.5 | <2.5 | <2.5 | 0.1-2.5 |
| Lead (ppm) | <5.0 | <5.0 | <5.0 | <5.0 | 0.1-5.0 |
| Selenium (ppm) | NA | <5.0 | <5.0 | <5.0 | 0.1-5.0 |

Example 2

Samples of mixotrophically cultured *Chlorella* whole cells were analyzed for amino acid content. The results of the sample analysis and extrapolated ranges are shown in Table 5.

TABLE 5

| Analyte | % in Biomass | Range (%) |
|---|---|---|
| Aspartic Acid | 3.88 | 2.0-5.0 |
| Threonine | 1.59 | 0.1-3.0 |
| Serine | 2.3 | 0.1-4.0 |
| Glutamic Acid | 6.01 | 4.0-8.0 |
| Proline | 2.73 | 0.1-5.0 |
| Glycine | 2.45 | 0.1-4.0 |
| Alanine | 3.34 | 1.0-5.0 |
| Cysteine | 0.56 | 0.1-2.0 |
| Valine | 1.99 | 0.1-4.0 |
| Methionine | 0.85 | 0.1-2.0 |
| Isoleucine | 1.39 | 0.1-3.0 |
| Leucine | 3.13 | 1.0-5.0 |
| Tyrosine | 1.50 | 0.1-3.0 |
| Phenylalanine | 1.77 | 0.1-4.0 |
| Lysine | 1.87 | 0.1-3.0 |
| Histidine | 0.96 | 0.1-2.0 |
| Arginine | 4.42 | 2.0-6.0 |
| Tryptophan | 0.95 | 0.1-2.0 |
| Total | 41.69 | 11.3-70 |

Example 3

Samples of mixotrophically cultured *Chlorella* whole cells were analyzed for carbohydrate content. The results of the sample analysis and extrapolated ranges are shown in Tables 6-7.

TABLE 6

| Analyte | % in Carbohydrates | % in Biomass | Range (% in biomass) |
|---|---|---|---|
| Polysaccharide | 81.61 | 32.6 | 20-40 |
| Raffinose | 1.47 | 0.6 | 0.1-2.0 |
| Cellobiose | 1.89 | 0.8 | 0.1-2.0 |
| Maltose | 5.18 | 2.1 | 0.1-4.0 |
| Glucose | 5 | 2 | 0.1-4.0 |
| Xylose | 0.7 | 0.3 | 0.1-1.0 |
| Galactose | 1.21 | 0.5 | 0.1-1.0 |
| Mannose | 0.86 | 0.3 | 0.1-1.0 |
| Fructose | 0.41 | 0.2 | 0.1-1.0 |
| Glucuronic acid | 1.67 | 0.7 | 0.1-2.0 |
| Total | 100 | 40.1 | 20.9-58.0 |

TABLE 7

| Analyte | % in Carbohydrates | % in Biomass | Range (% in Biomass) |
|---|---|---|---|
| Glucose | 54.5 | 21.8 | 10-30 |
| Xylose | 4.5 | 1.8 | 0.1-4 |
| Galactose | 16.5 | 6.6 | 4.0-8.0 |
| Arabinose | 5.2 | 2.1 | 0.1-4.0 |
| Mannose | 5.6 | 2.2 | 0.1-4.0 |
| Fructose | 2.7 | 1.1 | 0.1-2.0 |
| Glucuronic acid | 10 | 4 | 2.0-6.0 |
| Total | 99 | 39.6 | 16.4-58.0 |

Example 4

Samples of a low concentration mixotrophic *Chlorella*-based composition comprising 10% by weight mixotrophic *Chlorella* whole cells, <0.1% phosphoric acid, 0.3% potassium sorbate, and the remaining balance of water were analyzed for content. The results of the sample analysis and extrapolated ranges based on standard deviations are shown in Table 8, with NA indicating levels that were too low for detection. The results of the protein analysis are presented on a dry weight basis, while the remaining results are presented on a wet basis.

TABLE 8

| | Sample No. | | | | |
|---|---|---|---|---|---|
| | 1 | 2 | 3 | 4 | Range |
| % Protein (Leco) | 31.1 | 28.7 | 23.4 | 22 | 17-35 |
| % Lipids (AOAC) | 10.12 | 8.82 | 13.15 | 12.2 | 6-16 |
| Nitrogen (ppm) | 4976 | 4592 | 3744 | 3520 | 3,000-7,000 |
| Phosphorus (ppm) | 1600 | 1300 | 1500 | 1400 | 1,200-1,700 |
| Potassium (ppm) | 979.4 | 961.8 | 1385.5 | 1319.6 | 700-1700 |
| Boron (ppm) | NA | NA | NA | NA | |
| Calcium (ppm) | 160 | 100 | 120 | 130 | 65-200 |
| Iron (ppm) | 11 | 9.9 | 9.6 | 9.3 | 8-12 |
| Magnesium (ppm) | 130 | 94 | 95 | 86 | 70-160 |
| Manganese (ppm) | 2.5 | 2.0 | 2.1 | 1.8 | 1.5-3.0 |
| Sulfur (ppm) | NA | NA | NA | NA | |
| Zinc (ppm) | NA | NA | NA | NA | |
| Arsenic (ppm) | NA | NA | NA | NA | |
| Cadmium (ppm) | NA | NA | NA | NA | |
| Cobalt (ppm) | $1.2 \times 10^{-5}$ | $1.1 \times 10^{-5}$ | $1.1 \times 10^{-5}$ | $1.2 \times 10^{-5}$ | 0.00001-0.000013 |
| Chromium (ppm) | NA | NA | NA | NA | |
| Copper (ppm) | $5.5 \times 10^{-4}$ | $2.5 \times 10^{-4}$ | NA | $3.9 \times 10^{-4}$ | 0.00002-0.00006 |
| Mercury (ppm) | NA | NA | NA | NA | 0.1-2.0 |
| Molybedenum (ppm) | NA | NA | NA | NA | 0.1-2.5 |
| Sodium (ppm) | 0.047 | 0.028 | 0.028 | 0.022 | 0.017-0.058 |
| Nickel (ppm) | NA | NA | NA | NA | |

TABLE 8-continued

|  | Sample No. | | | | Range |
|---|---|---|---|---|---|
|  | 1 | 2 | 3 | 4 |  |
| Lead (ppm) | NA | NA | NA | NA |  |
| Selenium (ppm) | NA | NA | NA | NA |  |
| Aerobic Plate Count FSNS # 1.1 (FDA-BAM) (Est CFU/mL) | 380,000 | 130,000 | 91,000 | 56,000 | 80,000-400,000 |
| Salmonella FSNS # 32.2 (ELFA-AOAC) | (−)25 gram | (−)25 gram | (−)25 gram | (−)25 gram | 0 |
| Staphylococcus Aureus FSNS # 11.1 (FDA-BAM) (CFU/mL) | <10 | <10 | <10 | <10 | 0.1-10 |
| Coliform Count MPN FSNS # 7.1 (FDA-BAM) (MPN/mL) | <3.0 | <3.0 | <3.0 | <3.0 | 0.1-3.0 |
| E. coli MPN FSNS # 7.1 (FDA-BAM) (MPN/mL) | <3.0 | <3.0 | <3.0 | <3.0 | 0.1-3.0 |
| Mold Count FSNS # 4.1 (FDA-BAM) (CFU/mL) | <10 | <10 | <10 | <10 | 0.1-10 |
| Yeast Count FSNS # 4.1 (FDA-BAM) (CFU/mL) | <10 | <10 | 10 | <10 | 0.1-15 |

Example 5

Samples of mixotrophic *Chlorella* whole cells and low concentration mixotrophic *Chlorella*-based compositions comprising 10% by weight mixotrophic *Chlorella* whole cells, <0.1% phosphoric acid, 0.3% potassium sorbate, and the remaining balance of water were analyzed by the National Research Council Canada (Ottawa, Ontario) for phytohormone content. The mixotrophic *Chlorella*-based compositions used in this Example were not analyzed to quantify bacteria in the compositions, however aerobic plate counts for previous compositions prepared with the same components in the same manner contained 40,000-400,000 CFU/mL. All mixotrophic *Chlorella* whole cell samples had to be dried for analysis, and the results are reported with respect to dry weight (DW). Two samples of mixotrophic *Chlorella* whole cells analyzed contained mixotrophic *Chlorella* which had been dried by a drum drier prior to analysis, consisting of one sample where the mixotrophic *Chlorella* whole cells had been previously stored in a freezer (old) and one sample where the mixotrophic *Chlorella* whole cells had not been previously stored (fresh). A sample of mixotrophic *Chlorella* whole cells which was freeze dried before analysis was used as the closest approximation of the content of mixotrophic *Chlorella* cells that have not been subjected to a drying process. Samples of dried phototrophically-cultured *Chlorella vulgaris* was obtained from Hoosier Hill Farm LLC (Angola, Indiana).

The low concentration mixotrophic *Chlorella*-based composition samples were analyzed as liquid samples, and the results are reported with respect to fresh weight (FW). One sample contained mixotrophic *Chlorella*-based composition that had been previously stored in a freezer (old) and one sample contained mixotrophic *Chlorella*-based composition that had not been previously stored (fresh). The results of the sample analysis are shown in Tables 9-12, with n.d. indicated where the metabolite was not detected. The reported ng/g is equivalent to parts per billion (ppb) levels.

TABLE 9

| Solid Sample | ABA and ABA metabolites (ng/g DW) | | | | |
|---|---|---|---|---|---|
|  | ABA | ABAGE | PA | Neo-PA | t-ABA |
| Phototrophic *Chlorella vulgaris* | <4 | n.d. | <4 | n.d. | <4 |
| Mixotrophic *Chlorella* sp.- Drum Dried (stored) | 8 | n.d | n.d | <3.9 | 11 |
| Mixotrophic *Chlorella* sp.- Drum Dried (fresh) | <3.9 | <3.9 | <3.9 | n.d. | <3.9 |
| Mixotrophic *Chlorella* sp.- Freeze Dried (stored) | 11 | <3.9 | 7 | <3.9 | 15 |

| Liquid Sample | ABA and ABA metabolites (ng/g FW) | | | | |
|---|---|---|---|---|---|
|  | ABA | ABAGE | PA | Neo-PA | t-ABA |
| Stored Mixotrophic *Chlorella* composition | <0.4 | n.d. | n.d. | n.d. | n.d. |
| Fresh Mixotrophic *Chlorella* composition | n.d. | <0.4 | n.d. | n.d. | <0.4 |

The phytohormones in Table 9 are abbreviated as follows: ABA=cis-Abscisic acid; ABAGE=Abscisic acid glucose ester; PA=Phaseic acid; Neo-PA=Neo-Phaseic acid; and t-ABA=trans-Abscisic acid. As shown in Table 9, both drum dried samples showed lower levels of ABA and ABA metabolites than the freeze-dried sample. The mixotrophic *Chlorella* cells showed comparable levels of ABA and ABA metabolites to the phototrophic *Chlorella* cells samples. Neither of the low concentration mixotrophic *Chlorella*-based composition samples showed detectable levels of ABA and ABA metabolites.

TABLE 10

| Solid Sample | Cytokinins (ng/g DW) | | | | | | | |
|---|---|---|---|---|---|---|---|---|
| | t-ZOG | t-Z | c-Z | t-ZR | c-ZR | dhZR | iP | iPR |
| Phototrophic *Chlorella vulgaris* | n.d. | n.d. | 2 | <1 | 12 | 4 | 3 | 5 |
| Mixotrophic *Chlorella* sp.-Drum Dried (stored) | n.d. | <1.3 | 7 | 17 | 238 | n.d. | 3 | 13 |
| Mixotrophic *Chlorella* sp.-Drum Dried (fresh) | n.d. | n.d. | <1.2 | 6 | 233 | 1 | <1 | 4 |
| Mixotrophic *Chlorella* sp.-Freeze Dried (stored) | n.d. | 3 | 14 | 11 | 42 | <1 | 6 | 3 |

| Liquid Sample | Cytokinins (ng/g FW) | | | | | | | |
|---|---|---|---|---|---|---|---|---|
| | t-ZOG | t-Z | c-Z | t-ZR | c-ZR | dhZR | iP | iPR |
| Stored Mixotrophic *Chlorella* composition | n.d. | n.d. | 0 | <0.1 | 13 | n.d. | <0.1 | 0.4 |
| Fresh Mixotrophic *Chlorella* composition | 2 | n.d. | 14 | n.d. | 6 | n.d. | 4 | 1 |

The phytohormones in Table 10 are abbreviated as follows: t-ZOG=(trans) Zeatin-O-glucoside; t-Z=(trans) Zeatin; c-Z=(cis) Zeatin; t-ZR=(trans) Zeatin riboside; c-ZR=(cis) Zeatin riboside; dhZR=Dihydrozeatin riboside; iP=Isopentenyladenine; and iPR=Isopentenyladenosine. As shown in Table 10, both drum dried samples showed lower levels of t-Z, c-Z, and iP than the freeze-dried sample. The composition samples showed detectable levels of t-ZOG, c-Z, c-ZR, iP, and iPR, indicating that subjecting the mixotrophic *Chlorella*-based composition to a drum drying process can reduce the c-Z and iP content of the composition. The mixotrophic *Chlorella* cells samples showed higher content of t-ZR than the phototrophic *Chlorella* cells sample. The low concentration mixotrophic *Chlorella*-based composition samples showed detectable levels of t-ZOG, c-Z, c-ZR, iP, and iPR.

TABLE 11

| Solid Sample | Auxins (ng/g DW) | | | | |
|---|---|---|---|---|---|
| | IAA | IAA-Ala | IAA-Asp | IAA-Glu | IAA-Leu |
| Phototrophic *Chlorella vulgaris* | 70 | n.d. | <4 | n.d. | n.d. |
| Mixotrophic *Chlorella* sp.-Drum Dried (stored) | 412 | n.d. | n.d. | n.d. | n.d. |
| Mixotrophic *Chlorella* sp.-Drum Dried (fresh) | 414 | <3.9 | n.d. | n.d. | n.d. |
| Mixotrophic *Chlorella* sp.-Freeze Dried (stored) | 794 | n.d. | n.d. | n.d. | n.d. |

| Liquid Sample | Auxins (ng/g FW) | | | | |
|---|---|---|---|---|---|
| | IAA | IAA-Ala | IAA-Asp | IAA-Glu | IAA-Leu |
| Stored Mixotrophic *Chlorella* composition | 2 | n.d. | n.d. | n.d. | n.d. |
| Fresh Mixotrophic *Chlorella* composition | 27 | n.d. | n.d. | n.d. | n.d. |

The phytohormones in Table 11 are abbreviated as follows IAA=Indole-3-acetic acid; IAA-Ala=N-(Indole-3-yl-acetyl)-alanine; IAA-Asp=N-(Indole-3-yl-acetyl)-aspartic acid; IAA-Glu=N-(Indole-3-yl-acetyl)-glutamic acid; and IAA-Leu=N-(Indole-3-yl-acetyl)-leucine. As shown in Table 11, both drum dried samples showed lower levels of IAA than the freeze-dried sample, and the mixotrophic *Chlorella* cells samples showed IAA levels higher than the phototrophic *Chlorella* cells samples. The composition samples showed detectable levels of IAA, indicating that subjecting the mixotrophic *Chlorella*-based composition to a drum drying process can reduce the IAA content of the composition.

critical carbon dioxide extraction process. The mixotrophically cultured *Galidieria* sp. lysed cells were mechanically lysed. The BG-11 culture media treatment consisted of the same culture media used in the mixotrophic *Chlorella* culturing process. The centrifuged media treatment consisted of the cultured media separated from a mixotrophic *Chlorella* culture by centrifuge at the end of the culturing process (i.e., once the mixotrophic *Chlorella* was harvested). A commercially available macroalgae extract based product was obtained from Acadian Seaplants Limited (30 Brown Avenue, Dartmouth, Nova Scotia, Canada, B3B 1×8) for comparison. The commercially available product Transit Soil from FBSciences, Inc. (153 N Main Street, Ste 100, Collierville, TN 38017) was also tested.

TABLE 12

| Solid Sample | Gibberellins (ng/g DW) | | | | | | | |
| --- | --- | --- | --- | --- | --- | --- | --- | --- |
| | GA3 | GA4 | GA7 | GA8 | GA34 | GA44 | GA51 | GA53 |
| Phototrophic *Chlorella vulgaris* | <4 | <4 | n. d. | n. d. | n. d. | <4 | n. d. | n. d. |
| Mixotrophic *Chlorella* sp.-Drum Dried (stored) | <3.9 | n.d. | n.d. | n.d. | n.d. | n.d. | n.d. | n.d. |
| Mixotrophic *Chlorella* sp.-Drum Dried (fresh) | <3.9 | n.d. | n.d. | n.d. | n.d. | <3.9 | n.d. | n.d. |
| Mixotrophic *Chlorella* sp.-Freeze Dried (stored) | 7 | n.d. | n.d. | n.d. | <3.9 | n.d. | n.d. | n.d. |

| Liquid Sample | Gibberellins (ng/g FW) | | | | | | | |
| --- | --- | --- | --- | --- | --- | --- | --- | --- |
| | GA3 | GA4 | GA7 | GA8 | GA34 | GA44 | GA51 | GA53 |
| Stored Mixotrophic *Chlorella* composition | n.d. | <0.4 | n.d. | n.d. | <0.4 | n.d. | n.d. | n.d. |
| Fresh Mixotrophic *Chlorella* composition | n.d. | <0.4 | n.d. | n.d. | n.d. | n.d. | n.d. | n.d. |

The phytohormones in Table 12 are abbreviated as follows: GA=Gibberellins. As shown in Table 12, both drum dried samples showed lower levels of GA3 than the freeze-dried sample. Neither of the composition samples showed detectable levels of Gibberellins.

Example 6

An experiment was conducted to determine if application of a low concentration of a mixotrophic *Chlorella*-based composition to tomato seeds planted in soil affected the rate at which the seedlings emerge from the soil. Tomatoes are part of the Solanaceae family. Tomato seeds (*Solanum lycopersicum*) were planted in trays with standard soilless plant potting soil mix. Ten treatments were compared to an untreated control (UTC) and are listed in Table 13, with treatments 3 and 9 being duplicates. The treatments consisted of one treatment where the mixotrophic *Chlorella*-based composition had been dried by a drum drier (DD) before formulation for treatment, and two treatments where the mixotrophic *Chlorella*-based composition had not been dried (wet). The mixotrophic *Chlorella*-based composition in treatments 3 and 9 was not subjected to a drying or lysing process. The *Haematococcus pluvialis* extracted biomass was mechanically lysed before being subjected to a super-

TABLE 13

| Treatment No. | Treatment Description |
| --- | --- |
| 1 | UTC-untreated water check |
| 2 | Mixotrophic *Chlorella* sp.-Drum Dried Whole Cells (DD) |
| 3 | Mixotrophic *Chlorella* sp.-Whole Cells (Wet Plot 1) |
| 4 | Phototrophic *Haematococcus pluvialis*-Extracted Biomass |
| 5 | Mixotrophic *Galdieria* sp.-Whole Cells |
| 6 | Mixotrophic *Galdieria* sp.-Lysed Cells |
| 7 | Centrifuged Media from Mixotrophic *Chlorella* sp. culture |
| 8 | BG-11 Culture Media |
| 9 | Mixotrophic *Chlorella* sp.-Whole Cells (Wet Plot 2) |
| 10 | Grower Standard Product-Acadian Liquid Seaweed Concentrate |
| 11 | Grower Standard Product-Transit Soil |

The treatments were pasteurized, normalized to 10% solids (for treatments with microalgal solids), and stabilized with phosphoric acid (H3PO4) and potassium sorbate (C6H7KO2), with the remaining balance consisting of water. The mixotrophic *Chlorella*-based compositions were previously frozen and thawed and were incorporated into the formulated treatments used in this experiment after cold storage following being harvested from the microalgae culturing system. The mixotrophic *Chlorella*-based compositions used in the treatments of this experiment were not analyzed to quantify bacteria in the compositions, however aerobic plate counts for previous compositions prepared with the same components in the same manner contained 40,000-400,000 CFU/mL.

All treatments were applied to the seeds at the low concentration of 4.73 mL/gallon. The treatment method consisted of drenching the soil at a rate of 100 gallons/acre using a watering can. The treatments were applied immediately after planting the seeds. The tested concentration of 4.73 mL/gallon diluted the composition which originally contained 10% solids by weight of mixotrophic *Chlorella* whole cells to the low percent solids content of only 0.012495%.

Each treatment was applied to 100 seeds planted in a 10 by 10 pattern in planting trays, with each row of ten counting as a replicate (10 total replicates). Visual observations were made daily to record the percentage of plants that have emerged from the soil. The standard used for assessing emergence was the hypocotyl stage where a stem was visible to be protruding from the potting soil mix. The experiment was conducted inside a greenhouse with all seeds and treatments subjected to the same controlled conditions including temperature and light. All trays were treated with the same amount of water throughout the experiment. No additional nutrients were provided to the plants during the experiment. All data rated as significant was done so utilizing the New Duncan's Multiple Test Range at a 90% confidence level, such that values with a statistical significant identifier of the same letter are not significantly different.

Results are shown in Table 14-18 with accompanying statistical significance grouping identifiers.

TABLE 14

Plant Emergence (Ave. % of plants emerged on date)

| | Day 1 | | | Day 2 | | | Day 3 | | |
|---|---|---|---|---|---|---|---|---|---|
| | AM | | PM | | AM | | PM | | AM | PM |
| 1 | 0 | a | 0 | c | 0 | d | 2 | f | 3 d | 16 d |
| 2 | 0 | a | 0 | c | 0 | d | 1 | f | 2 d | 21 d |
| 3 | 0 | a | 3 | c | 6 | c | 24 | d | 23 bcd | 60 b |
| 4 | 0 | a | 3 | c | 4 | c | 24 | d | 26 bcd | 60 b |
| 5 | 0 | a | 0 | c | 0 | d | 5 | f | 6 d | 45 c |
| 6 | 0 | a | 0 | c | 0 | d | 5 | f | 5 d | 44 c |
| 7 | 0 | a | 0 | c | 0 | d | 7 | f | 10 d | 43 c |
| 8 | 0 | a | 0 | c | 0 | d | 10 | ef | 10 d | 49 bc |
| 9 | 0 | a | 8 | ab | 10 | ab | 42 | b | 45 ab | 72 a |
| 10 | 0 | a | 0 | c | 0 | d | 18 | de | 19 cd | 6 b |
| 11 | 0 | a | 0 | c | 0 | d | 16 | de | 44 ab | 44 c |

TABLE 15

Plant Emergence (Ave. % of plants emerged on date)

| | Day 4 | | | Day 5 | | | Day 6 | | Day 7 | |
|---|---|---|---|---|---|---|---|---|---|---|
| | AM | | PM | | AM | | PM | | PM | | PM |
| 1 | 17 | g | 47 | g | 55 | e | 76 | a | 83 a | 84 A |
| 2 | 24 | g | 55 | fg | 56 | e | 77 | a | 84 a | 87 A |
| 3 | 65 | abc | 70 | b-e | 79 | abc | 83 | a | 82 a | 78 A |
| 4 | 61 | bcd | 73 | a-e | 79 | abc | 84 | a | 84 a | 85 A |
| 5 | 44 | ef | 64 | def | 64 | de | 82 | a | 83 a | 88 A |
| 6 | 43 | f | 61 | ef | 66 | cde | 77 | a | 80 a | 80 A |
| 7 | 44 | ef | 64 | def | 73 | a-d | 82 | a | 81 a | 83 A |
| 8 | 56 | cde | 64 | def | 66 | cde | 77 | a | 74 a | 77 a |
| 9 | 73 | ab | 80 | ab | 83 | ab | 85 | a | 88 a | 87 a |
| 10 | 62 | bcd | 79 | abc | 79 | abc | 85 | a | 89 a | 88 a |
| 11 | 47 | ef | 68 | cde | 72 | a-d | 79 | a | 83 a | 84 a |

As shown in Tables 14-15, treatments 3 and 9 comprising the mixotrophic *Chlorella*-based composition emerged out of the soil sooner that the UTC, the grower standard commercial products in treatments 10 and 11, and treatments 5-8, showing a statistically significant difference on Day 2 AM. The percentage of plants emerged for all treatments converged at the end of the experiment.

TABLE 16

Plant Emergence (Ave. % of plants emerged at observation time)

| | Untreated Water Check (UTC) | Mixotrophic *Chlorella* sp. Whole Cells (Treatment 3) | % Increase over UTC | Mixotrophic *Chlorella* sp. Whole Cells (Treatment 9) | % Increase over UTC |
|---|---|---|---|---|---|
| Day 1 AM | 0 a | 0 a | | 0 a | |
| Day 1 PM | 0 c | 3 c | | 8 ab | |
| Day 2 AM | 0 d | 6 d | | 10 ab | |
| Day 2 PM | 2 f | 24 d | 1100% | 42 b | 2000% |
| Day 3 AM | 3 d | 23 bcd | 667% | 45 ab | 1400% |
| Day 3 PM | 16 d | 60 b | 275% | 72 a | 350% |
| Day 4 AM | 17 g | 65 abc | 282% | 73 ab | 329% |
| Day 4 PM | 47 g | 70 b-e | 49% | 80 ab | 70% |
| Day 5 AM | 55 e | 79 abc | 44% | 83 ab | 51% |
| Day 5 PM | 76 a | 83 a | 9% | 85 a | 12% |
| Day 6 PM | 83 a | 82 a | −1% | 88 a | 6% |
| Day 7 PM | 84 a | 78 a | −7% | 87 a | 4% |

Table 16 shows treatments 3 and 9 comprising the mixotrophic *Chlorella*-based composition with respect to the UTC. As shown in Table 16, treatments 3 and 9 began emerging from the soil on Day 1 PM, while the UTC treatment did not begin emergence until Day 2 PM and lagged behind treatments 3 and 9 by a statistically significant margin on most days until Day 5 PM. Of the plots receiving treatments comprising the mixotrophic *Chlorella*-based composition, treatment 3 demonstrated a statistically significant difference from the UTC at Day 2 PM, Day 3 PM, Day 4 AM, Day 4 PM and Day 5 AM, and treatment 9 demonstrated a statistically significant difference from the UTC from Day 1 PM through Day 5 AM. Treatments 3 and 9 also reached at least 70% emergence a day before the UTC and maintained a numerical increase of at least 27% over the UTC through Day 5 AM.

TABLE 17

Plant Emergence (Average % of plants emerged at observation time)

| | Untreated Control (UTC) | Mixotrophic *Chlorella* DD (Treatment 2) | Mixotrophic *Chlorella* Wet Plot 1 (Treatment 3) | Mixotrophic *Chlorella* Wet Plot 2 (Treatment 9) |
|---|---|---|---|---|
| Day 1 AM | 0 a | 0 a | 0 a | 0 a |
| Day 1 PM | 0 c | 0 c | 3 c | 8 ab |
| Day 2 AM | 0 d | 0 d | 6 d | 10 ab |
| Day 2 PM | 2 f | 1 f | 24 d | 42 b |
| % over UTC | | −50% | 1100% | 2000% |
| % over DD | | | 2300% | 4100% |
| Day 3 AM | 3 d | 2 d | 23 bed | 45 ab |
| % over UTC | | −33% | 667% | 1400% |
| % over DD | | | 1050% | 2150% |
| Day 3 PM | 16 d | 21 d | 60 b | 72 a |
| % over UTC | | 31% | 275% | 350% |
| % over DD | | | 186% | 242% |
| Day 4 AM | 17 g | 24 g | 65 abc | 73 ab |
| % over UTC | | 41% | 282% | 329% |
| % over DD | | | 171% | 204% |
| Day 4 PM | 47 g | 55 fg | 70 b-e | 80 ab |
| % over UTC | | 17% | 49% | 70% |
| % over DD | | | 27% | 45% |
| Day 5 AM | 55 e | 56 e | 79 abc | 83 ab |
| % over UTC | | 2% | 44% | 51% |
| % over DD | | | 41% | 48% |

TABLE 17-continued

Plant Emergence (Average % of plants emerged at observation time)

|  | Untreated Control (UTC) | Mixotrophic Chlorella DD (Treatment 2) | Mixotrophic Chlorella Wet Plot 1 (Treatment 3) | Mixotrophic Chlorella Wet Plot 2 (Treatment 9) |
|---|---|---|---|---|
| Day 5 PM | 76 a | 77 a | 83 a | 85 a |
| % over UTC |  | 1% | 9% | 12% |
| % over DD |  |  | 8% | 10% |
| Day 6 PM | 83 a | 84 a | 82 a | 88 a |
| % over UTC |  | 1% | −1% | 6% |
| % over DD |  |  | −2% | 5% |
| Day 7 PM | 84 a | 87 a | 78 a | 87a |
| % over UTC |  | 4% | −7% | 4% |
| % over DD |  |  | −10% | 0% |

As shown in Table 17, the two treatments comprising wet mixotrophic *Chlorella*-based composition emerged from the soil faster than the UTC and treatment comprising DD mixotrophic *Chlorella*-based composition. Of the plots receiving treatments comprising wet mixotrophic *Chlorella*-based composition, the first plot demonstrated a statistically significant difference from the UTC and treatment comprising DD mixotrophic *Chlorella*-based composition at Day 2 PM, Day 3 PM, Day 4 AM, Day 4 PM and Day 5 AM, and the second plot demonstrated a statistically significant difference from the UTC and treatment comprising DD mixotrophic *Chlorella*-based composition from Day 1 PM through Day 5 AM. The treatments comprising wet mixotrophic *Chlorella*-based composition also reached at least 70% emergence a day before the UTC and treatment comprising DD mixotrophic *Chlorella*-based composition and maintained a numerical increase of at least 27% over the UTC and treatment comprising DD *Chlorella*-based composition through Day 5 AM. The performance of the treatment comprising DD mixotrophic *Chlorella*-based composition largely mirrored the performance of the UTC, with no statistically significant difference over the course of the experiment and numerical increases above 10% on only Day 3 PM through Day 4 PM. Thus, the results indicate that drying the mixotrophic *Chlorella*-based composition with a drum drier in the preparation process reduced the effectiveness of the compositions to accelerate emergence of the tomato plants when applied as soil drench.

TABLE 18

Plant Emergence (Ave. % of plants emerged on Day 4 AM)

|  | 22-May AM |  | % increase over UTC |
|---|---|---|---|
| UTC-untreated water check | 17 | f |  |
| Mixotrophic *Chlorella* sp.-Drum Dried Whole Cells (DD) | 24 | f | 41% |
| Mixotrophic *Chlorella* sp.-Whole Cells (Average of Wet Plots 1 and 2) | 69 | ab | 306% |
| Phototrophic *Haematococcus pluvialis*-Extracted Biomass | 61 | bcd | 259% |
| Mixotrophic *Galdieria* sp.-Whole Cells | 44 | e | 159% |
| Mixotrophic *Galdieria* sp.-Lysed Cells | 43 | e | 153% |
| Centrifuged Media from Mixotrophic *Chlorella* sp. culture | 44 | e | 159% |
| BG-11 Culture Media | 56 | cde | 229% |
| Grower Standard Product-Acadian Liquid Seaweed Concentrate | 62 | abc | 265% |
| Grower Standard Product-Transit Soil | 47 | de | 176% |

Table 18 displays the data from the Day 4 AM with the duplicate mixotrophic *Chlorella*-based composition treatments averaged for comparison to the other treatments and shows a statistically significant difference for the mixotrophic *Chlorella*-based composition which had not been dried (i.e., wet) as compared to the UTC, which amounts to a numerical increase of 306%. Table 18 also shows that the mixotrophic *Chlorella*-based composition treatment that had not been dried outperformed the commercially available products and was significantly different from the mixotrophic *Galdieria* and drum dried mixotrophic *Chlorella*-based composition treatments.

Example 7

An experiment was conducted to determine if the method of application of a low concentration of a mixotrophic *Chlorella*-based composition to tomato seeds planted in soil affected the rate at which the seedlings emerge from the soil and mature. Tomato seeds (*Solanum lycopersicum*) were planted in trays with a potting soil mix of sphagnum moss, perlite, and vermiculite (2:1:1). Three treatments comprising a mixotrophic *Chlorella*-based composition were compared to an untreated control (UTC). The treatments were pasteurized, normalized to 10% solids, and stabilized with phosphoric acid ($H_3PO_4$) and potassium sorbate ($C_6H_7KO_2$), with the remaining balance consisting of water. The stored mixotrophic *Chlorella*-based composition was frozen after being harvested from the microalgae culturing system and thawed before formulation in the liquid composition for treatments used in the experiment. The fresh mixotrophic *Chlorella*-based composition was not previously frozen and was incorporated into the liquid composition for treatments used in this experiment directly after being harvested from the microalgae culturing system. The composition used in the treatments of this experiment were not analyzed to quantify bacteria in the compositions, however aerobic plate counts for previous compositions prepared with the same components in the same manner contained 40,000-400,000 CFU/mL.

The mixotrophic *Chlorella*-based liquid composition treatments were applied to the seeds through two different treatment methods. The first treatment method comprised soaking the seeds in the low concentration of 8 mL/gallon of the mixotrophic *Chlorella*-based liquid composition for two hours with constant sparging of air to avoid oxygen deprivation, removing the seeds from the composition, drying the seeds overnight, and then planting the seeds in the potting soil mix. The second treatment method comprised soaking the seeds in water for two hours with constant sparing of air to avoid oxygen deprivation, removing the seeds from water, drying the seeds overnight, planting the seeds in the potting soil mix with the low concentration of 8 mL/gallon of the mixotrophic *Chlorella*-based liquid composition in the base of the planting tray to allow the seeds to be treated with the liquid composition through capillary action. The tested concentration of 8 mL/gallon diluted the composition which originally contained 10% solids by weight of mixotrophic *Chlorella* whole cells to the low percent solids content of only 0.021134%.

Each of the three treatments were applied to 72 seeds. Visual observations of the soil and plants were made daily on days 6 and 7 to record how many seeds had achieved emergence and maturation, as explained below. The standard used for assessing emergence was the achievement of the hypocotyl stage, where a stem was visibly protruding from the potting soil mix. The standard used for assessing maturation was the achievement of the cotyledon stage, where two leaves had visibly formed on the emerged stem.

The experiment was conducted indoors with all seeds and treatments subjected to the same controlled conditions including temperature, light, and supply of water. No other nutrients were supplied during the experiment. Light supplied was artificial and provided by fluorescent bulbs 24 hours a day. Results of the experiment are presented in Tables 19-2

TABLE 19

|  | Number of plants emerged by day | |
|---|---|---|
|  | Day 6 | Day 7 |
| Untreated Control (UTC) | 28 | 42 |
| 10% Mixotrophic *Chlorella* Fresh Soak | 22 | 46 |
| 10% Mixotrophic *Chlorella* Stored Soak | 26 | 47 |
| 10% Mixotrophic *Chlorella* Fresh Capillary | 43 | 58 |

TABLE 20

|  | % of total plants emerged by day | |
|---|---|---|
|  | Day 6 | Day 7 |
| Untreated Control (UTC) | 39 | 58 |
| 10% Mixotrophic *Chlorella* Fresh Soak | 31 | 64 |
| 10% Mixotrophic *Chlorella* Stored Soak | 36 | 65 |
| 10% Mixotrophic *Chlorella* Fresh Capillary | 60 | 81 |

TABLE 21

|  | % increase of plants emerged by day over UTC | |
|---|---|---|
|  | Day 6 | Day 7 |
| 10% Mixotrophic *Chlorella* Fresh Soak | −21% | 10% |
| 10% Mixotrophic *Chlorella* Stored Soak | −7% | 12% |
| 10% Mixotrophic *Chlorella* Fresh Capillary | 54% | 38% |

As shown in the Tables 19-21, the capillary action treatment and seed soak treatments showed higher performance by day seven than the UTC regarding emergence of the plants. On day seven the capillary action treatment showed an increase of 38%, the seed soak treatment with stored mixotrophic *Chlorella*-based composition showed an increase of 12%, and the seed soak treatment with fresh mixotrophic *Chlorella*-based composition showed an increase of 10% over the UTC. These results show that a low concentration of a mixotrophic *Chlorella*-based composition is effective in increasing the emergence of a seedling as compared to an untreated seed when applied in a capillary action application.

TABLE 22

|  | Number of plants matured by day | |
|---|---|---|
|  | Day 6 | Day 7 |
| Untreated Control (UTC) | 11 | 37 |
| 10% Mixotrophic *Chlorella* Fresh Soak | 18 | 41 |
| 10% Mixotrophic *Chlorella* Stored Soak | 18 | 39 |
| 10% Mixotrophic *Chlorella* Fresh Capillary | 23 | 47 |

TABLE 23

|  | % of total plants matured by day | |
|---|---|---|
|  | Day 6 | Day 7 |
| Untreated Control (UTC) | 15 | 51 |
| 10% Mixotrophic *Chlorella* Fresh Soak | 25 | 57 |
| 10% Mixotrophic *Chlorella* Stored Soak | 25 | 54 |
| 10% Mixotrophic *Chlorella* Fresh Capillary | 32 | 65 |

TABLE 24

|  | % increase of plants matured by day over the UTC | |
|---|---|---|
|  | Day 6 | Day 7 |
| 10% Mixotrophic *Chlorella* Fresh Soak | 64% | 11% |
| 10% Mixotrophic *Chlorella* Stored Soak | 64% | 5% |
| 10% Mixotrophic *Chlorella* Fresh Capillary | 109% | 27% |

As shown in the Tables 22-24, the capillary action treatment and seed soak treatments showed higher performance on days 6 and 7 than the UTC regarding maturation of the plants. The capillary action treatment showed an increase of at least 27%, the seed soak treatment with stored mixotrophic *Chlorella*-based composition showed an increase of at least 5%, and the seed soak treatment with fresh mixotrophic *Chlorella*-based composition showed an increase of at least 11% over the UTC. These results show that a low concentration of a mixotrophic *Chlorella*-based composition is effective in increasing the maturation of a seedling as compared to an untreated seed when applied in a capillary action application.

Example 8

An experiment was conducted to determine if the method of application of a low concentration of a mixotrophic *Chlorella*-based composition to tomato seeds planted in soil affected the rate at which the seedlings emerge from the soil and mature. Tomato seeds (*Solanum lycopersicum*) were planted in trays with a potting soil mix of sphagnum moss, perlite, and vermiculite (2:1:1). Two treatments comprising mixotrophically cultured a mixotrophic *Chlorella*-based composition were compared to an untreated control (UTC). The treatments were pasteurized, normalized to 10% solids, and stabilized with phosphoric acid ($H_3PO_4$) and potassium sorbate (C6H7KO2), with the remaining balance consisting of water. The mixotrophic *Chlorella*-based composition was not previously frozen and was incorporated into the liquid composition for treatments used in this experiment directly after being harvested from the microalgae culturing system. The composition used in the treatments of this experiment was not analyzed to quantify bacteria in the composition, however aerobic plate counts for previous compositions prepared with the same components in the same manner contained 40,000-400,000 CFU/mL.

The mixotrophic *Chlorella*-based liquid composition was applied to the seeds at two different concentrations, 4.7 mL/gallon or 8 mL/gallon, using the same treatment method. The tested concentration of 4.7 mL/gallon diluted the composition which originally contained 10% solids by weight of mixotrophic *Chlorella* whole cells to the low percent solids content of only 0.012416%. The tested concentration of 8 mL/gallon diluted the composition which originally contained 10% solids by weight of mixotrophic *Chlorella* whole cells to the low percent solids content of only 0.021134%. The treatment method consisted of drenching the soil from the top with 0.75 gallon of the liquid composition (equivalent to an application rate of 100 gallons/acre) at the identified concentrations after planting the seeds.

Each of the two treatments were applied to two trays of 72 seeds. Visual observations of the soil and plants were made daily to record how many seeds had achieved emergence and maturation, as explained below. The standard used for assessing emergence was the achievement of the hypocotyl stage where a stem was visibly protruding from the potting soil mix. The standard used for assessing maturation was the achievement of the cotyledon stage where two leaves had visibly formed on the emerged stem. The experiment was conducted indoors with all seeds and treatments subjected to the same controlled conditions including temperature, light, and supply of water. No other nutrients were supplied during the experiment. Light supplied was artificial and provided by fluorescent bulbs 24 hours a day. Results of the experiment are presented in Tables 25-30.

TABLE 25

| | Number of plants emerged by day | | | | | | | | |
|---|---|---|---|---|---|---|---|---|---|
| | 1 | 2 | 3 | 4 | 5 | 6 | 7 | 8 | 9 |
| Untreated Control (UTC) | — | — | 0 | 0 | 0 | 10 | 40 | 43 | 69 |
| 10% Mixotrophic *Chlorella* 4.7 mL | — | — | 0 | 0 | 0 | 20 | 57 | 62 | 87 |
| 10% Mixotrophic *Chlorella* 8 mL | — | — | 0 | 0 | 0 | 39 | 59 | 65 | 88 |

TABLE 26

| | % of total plants emerged by day | | | | | | | | |
|---|---|---|---|---|---|---|---|---|---|
| | 1 | 2 | 3 | 4 | 5 | 6 | 7 | 8 | 9 |
| Untreated Control (UTC) | 0 | 0 | 0 | 0 | 0 | 7 | 28 | 30 | 48 |
| 10% Mixotrophic *Chlorella* 4.7 mL | 0 | 0 | 0 | 0 | 0 | 14 | 40 | 43 | 60 |
| 10% Mixotrophic *Chlorella* 8 mL | 0 | 0 | 0 | 0 | 0 | 27 | 41 | 45 | 61 |

TABLE 27

| | % increase of plants emerged by day over the UTC | | | | | | | | |
|---|---|---|---|---|---|---|---|---|---|
| | 1 | 2 | 3 | 4 | 5 | 6 | 7 | 8 | 9 |
| 10% Mixotrophic *Chlorella* 4.7 mL | — | — | — | — | — | 100% | 43% | 44% | 26% |
| 10% Mixotrophic *Chlorella* 8 mL | — | — | — | — | — | 290% | 48% | 51% | 28% |

As shown in the Tables 25-27, the 8 and 4.7 mL/gallon applications showed consistently higher performance than the UTC regarding emergence of the plants, with the 8 mL/gallon consistently performing better than the 4.7 mL/gallon. The 4.7 mL/gallon application showed at least a 26% and as much as a 100% increase over the UTC on comparative days, and the 8 mL/gallon application demonstrated at least a 28% and as much as a 290% increase over the UTC. The largest difference between the 4.7 and 8 mL/gallon applications occurred on day 6. These results show that a low concentration of a mixotrophic *Chlorella*-based composition is effective in increasing the emergence of a seedling as compared to an untreated seed when applied in a soil drench application.

TABLE 28

| | Number of plants matured by day | | | | | | | | |
|---|---|---|---|---|---|---|---|---|---|
| | 1 | 2 | 3 | 4 | 5 | 6 | 7 | 8 | 9 |
| Untreated Control (UTC) | — | — | 0 | 0 | 0 | 2 | 22 | 45 | 65 |
| 10% Mixotrophic *Chlorella* 4.7 mL | — | — | 0 | 0 | 0 | 9 | 42 | 69 | 83 |
| 10% Mixotrophic *Chlorella* 8 mL | — | — | 0 | 0 | 0 | 8 | 46 | 68 | 79 |

TABLE 29

| | % of total plants matured by day | | | | | | | | |
|---|---|---|---|---|---|---|---|---|---|
| | 1 | 2 | 3 | 4 | 5 | 6 | 7 | 8 | 9 |
| Untreated Control (UTC) | 0 | 0 | 0 | 0 | 0 | 1 | 15 | 31 | 45 |
| 10% Mixotrophic *Chlorella* 4.7 mL | 0 | 0 | 0 | 0 | 0 | 6 | 29 | 48 | 58 |
| 10% Mixotrophic *Chlorella* 8 mL | 0 | 0 | 0 | 0 | 0 | 6 | 32 | 47 | 55 |

TABLE 30

| | % increase of plants matured by day over the UTC | | | | | | | | |
|---|---|---|---|---|---|---|---|---|---|
| | 1 | 2 | 3 | 4 | 5 | 6 | 7 | 8 | 9 |
| 10% Mixotrophic *Chlorella* 4.7 mL | — | — | — | — | — | 350% | 91% | 53% | 28% |
| 10% Mixotrophic *Chlorella* 8 mL | — | — | — | — | — | 300% | 109% | 51% | 22% |

As shown in the Tables 28-30, the 8 and 4.7 mL/gallon applications showed consistently higher performance than the UTC regarding maturation of the plants, with the 4.7 mL/gallon application performing better than the 8 mL/gallon on days 6, 8, and 9. The 4.7 mL/gallon application showed at least a 28% and as much as a 350% increase over the UTC on comparative days and the 8 mL/gallon application demonstrated at least a 22% and as much as a 300% increase over the UTC. These results show that a low concentration of a mixotrophic *Chlorella*-based composition is effective in increasing the maturation of a seedling as compared to an untreated seed when applied in a soil drench application.

Example 9

An experiment was conducted to determine if a low concentration and low frequency application of mixotrophic *Chlorella*-based composition to heirloom tomato (cv German striped) plants by foliar application affected the initial growth and sizing of the plants. Tomato seeds (*Solanum lycopersicum*) were planted in trays with standard soilless plant potting soil mix and grown in a nursery greenhouse. Treatments of a mixotrophic *Chlorella*-based composition and a commercially available reference product were compared to an untreated control (UTC) and are listed in Table 31, with duplicate treatments of the mixotrophic *Chlorella*-based composition being tested. A commercially available macroalgae extract based product was obtained from Acadian Seaplants Limited (30 Brown Avenue, Dartmouth, Nova Scotia, Canada, B3B 1×8) for comparison.

TABLE 31

| Treatment No. | Treatment Description |
|---|---|
| 1 | UTC-untreated water check |
| 2 | Mixotrophic *Chlorella* sp.-Drum Dried Whole Cells (DD) |
| 3 | Mixotrophic *Chlorella* sp.-Whole Cells (Wet Plot 1) |
| 4 | Mixotrophic *Chlorella* sp.-Whole Cells (Wet Plot 2) |
| 5 | Grower Standard Product-Acadian Liquid Seaweed Concentrate |

The mixotrophic *Chlorella*-based composition was pasteurized, normalized to 10% solids, and stabilized with phosphoric acid (H3PO4) and potassium sorbate (C6H7KO2), with remaining balance consisting of water. The mixotrophic *Chlorella* whole cells were not previously subjected to a purification process to isolate the cells from the microalgae culturing medium, nor were the cells previously subjected to a drying, extraction, or other process that can lyse or disrupt the cell walls, except as indicated for the drum dried treatment. The composition comprising mixotrophic *Chlorella* used in the treatments of this experiment were not analyzed to quantify bacteria in the compositions, however aerobic plate counts for previous compositions prepared with the same components in the same manner contained 40,000-400,000 CFU/mL. The mixotrophic *Chlorella* composition was previously frozen and thawed, and was incorporated into the liquid composition for treatments used in this experiment after cold storage following being harvested from the microalgae culturing system.

The mixotrophic *Chlorella*-based composition treatments were applied to the plants at a concentration of 4 mL/gallon. The tested concentration of 4 mL/gallon diluted the composition which originally contained 10% solids by weight of mixotrophic *Chlorella* whole cells to the low percent solids content of only 0.010567%. The Acadian treatment was applied to plants at a concentration of 9.46 mL/gallon. The low concentration and low frequency treatment method consisted of directly spraying the foliage of the plants a rate of 25 gallons/acre using a spray bottle. A total of three applications were applied with the first application occurring three weeks after planting (7-10 days after emergence). The second application was applied five days after the first, and the third application was applied six days after the second.

Each treatment was applied to a 14-inch by 14-inch planting flats containing plants resulting from 25-30 seeds. There were eight replicates of each treatment. All seeds were planted in a standard soilless potting plant mix. Each plant analyzed was counted as a replicate with eight replicates considered for each treatment evaluation. Analysis occurred after the second treatment and after the third treatment. The chlorophyll content was estimated by SPAD (Soil-Plant Analysis Development) value, a numeric value provided by a Minolta SPAD meter which analyzes the amount of light in a specific light spectrum passing through a leaf and converts that reading to a numerical value as an indicator of chlorophyll density in the leaf. The experiment was conducted inside a greenhouse with all seeds and treatments subjected to the same controlled conditions including temperature and light. All trays were treated with the same amount of water throughout the experiment. No additional nutrients were provided to the plants during the experiment. All data rated as significant was done so utilizing the New Duncan's Multiple Test Range at a 90% confidence level, such that values with a statistical significant identifier of the same letter are not significantly different. Results are shown in Tables 32-37 designated with an F for foliar application, with accompanying statistical significance grouping identifiers.

Example 10

An experiment was conducted to determine if a low concentration and low frequency application of mixotrophic *Chlorella*-based composition to heirloom tomato (cv German striped) plants (*Solanum lycopersicum*) by soil application affected the initial growth and sizing of the plants. The soil application trial occurred in the same location, with the same treatments, and with the same design as the experiment in Example 9.

The mixotrophic *Chlorella*-based composition treatments were applied to the plants at a low concentration of 4.73 mL/gallon. The tested concentration of 4.73 mL/gallon diluted the composition which originally contained 10% solids by weight of mixotrophic *Chlorella* whole cells to the low percent solids content of only 0.012495%. The Acadian treatment was applied to plants at a concentration of 9.46 mL/gallon. The low concentration and low frequency treatment method consisted of drenching the soil at a rate of 100 gallons/acre. A total of three treatments were applied with the first application occurring two weeks after planting (7-10 days after emergence). The second treatment was applied nine days after the first, and the third treatment was applied five days after the second. All data rated as significant was done so utilizing the New Duncan's Multiple Test Range at a 90% confidence level, such that values with a statistical significant identifier of the same letter are not significantly different. Results are shown in Tables 32-37 designated with an S for soil application, with accompanying statistical significance grouping identifiers.

TABLE 32

| Nursery Tomato Plant Sizing-Plant Height (inches) | | | |
|---|---|---|---|
| | Avg. | Increase over UTC | Increase over DD |
| 1 UTC-untreated water check F | 6.00 | cde | |
| UTC-untreated water check S | 5.85 | ab | |
| 2 Mixotrophic *Chlorella* sp.-Whole Cells DD F | 6.48 | ab | 8% |
| Mixotrophic *Chlorella* sp.-Whole Cells DD S | 5.53 | bcd | −5% |
| 3 Mixotrophic *Chlorella* sp.-Whole Cells Wet Plot 1 F | 5.27 | fg | −12% | −18% |
| Mixotrophic *Chlorella* sp.-Whole Cells Wet Plot 1 S | 5.20 | def | −11% | −6% |
| 4 Mixotrophic *Chlorella* sp.-Whole Cells Wet Plot 2 F | 6.13 | abcd | 2% | −5% |
| Mixotrophic *Chlorella* sp.-Whole Cells Wet Plot 2 S | 5.52 | bcd | −6% | 0% |
| 5 Grower Standard Product-Acadian Liquid Seaweed Concentrate F | 5.94 | de | −1% | |
| Grower Standard Product-Acadian Liquid Seaweed Concentrate S | 5.67 | abc | −3% | |

As shown in Table 32, the treatments comprising wet mixotrophic *Chlorella*-based composition did not show a statistically significant or numerical increase over the UTC regarding plant height. Additionally, the wet mixotrophic *Chlorella*-based composition did not show a statistically significant or numerical increase over the DD mixotrophic *Chlorella*-based composition treatment.

TABLE 33

Nursery Tomato Plant Sizing-Leaf Number

| | Avg. | | Increase over UTC | Increase over DD |
|---|---|---|---|---|
| 1 UTC-untreated water check F | 5.1 | a | | |
| UTC-untreated water check S | 4.5 | a | | |
| 2 Mixotrophic *Chlorella* sp.-Whole Cells DD F | 5.2 | a | 2% | |
| Mixotrophic *Chlorella* sp.-Whole Cells DD S | 4.6 | a | 3% | |
| 3 Mixotrophic *Chlorella* sp.-Whole Cells Wet Plot 1 F | 4.9 | a | −2% | −6% |
| Mixotrophic *Chlorella* sp.-Whole Cells Wet Plot 1 S | 4.5 | a | 0% | −2% |
| 4 Mixotrophic *Chlorella* sp.-Whole Cells Wet Plot 2 F | 5.3 | a | 4% | 2% |
| Mixotrophic *Chlorella* sp.-Whole Cells Wet Plot 2 S | 4.4 | a | −3% | −4% |
| 5 Grower Standard Product-Acadian Liquid Seaweed Concentrate F | 4.9 | a | −2% | |
| Grower Standard Product-Acadian Liquid Seaweed Concentrate S | 4.6 | a | 1% | |

As shown in Table 33, the treatments comprising the wet mixotrophic *Chlorella*-based composition did not show a statistically significant over the UTC or DD mixotrophic *Chlorella*-based composition treatment regarding leaf number.

TABLE 34

Nursery Tomato Chlorophyll Content (SPAD)

| | Avg. | | Increase over UTC | Increase over DD |
|---|---|---|---|---|
| 1 UTC-untreated water check F | 25.9 | f | | |
| UTC-untreated water check S | 30.4 | a | | |
| 2 Mixotrophic *Chlorella* sp.-Whole Cells DD F | 27.8 | ef | 7% | |
| Mixotrophic *Chlorella* sp.-Whole Cells DD S | 29.1 | a | −4% | |
| 3 Mixotrophic *Chlorella* sp.-Whole Cells Wet Plot 1 F | 32.1 | bcd | 24% | 15% |
| Mixotrophic *Chlorella* sp.-Whole Cells Wet Plot 1 S | 30.7 | a | 1% | 5% |
| 4 Mixotrophic *Chlorella* sp.-Whole Cells Wet Plot 2 F | 34.0 | ab | 31% | 22% |
| Mixotrophic *Chlorella* sp.-Whole Cells Wet Plot 2 S | 32.7 | a | 8% | 12% |
| 5 Grower Standard Product-Acadian Liquid Seaweed Concentrate F | 34.5 | ab | 33% | |
| Grower Standard Product-Acadian Liquid Seaweed Concentrate S | 30.6 | a | 1% | |

As shown in Table 34, the foliar treatments comprising the wet mixotrophic *Chlorella*-based composition did show a statistically significant increase over the UTC and DD mixotrophic *Chlorella*-based composition treatment regarding chlorophyll content. The foliar treatments also showed numerical increases over the UTC of 24% and 31%, as well as numerical increases over the DD mixotrophic *Chlorella*-based composition treatment of 15% and 22%. These results show that small amounts of the mixotrophic *Chlorella*-based composition at a low concentration and low frequency application are effective at improving chlorophyll content in plants when applied to the foliage. The results also indicate that drying the mixotrophic *Chlorella*-based composition with a drum drier in the preparation process reduced the effectiveness of the compositions to enhance the chlorophyll content of the tomato plants when applied in a foliar application. The soil applications comprising the wet mixotrophic *Chlorella*-based composition did not show a statistically significant or numerical increase over the UTC or DD *Chlorella*-based composition treatment.

TABLE 35

Nursery Tomato Plant Sizing-Whole Plant Weight (grams)

| | Avg. | | Increase over UTC | Increase over DD |
|---|---|---|---|---|
| 1 UTC-untreated water check F | 6.8 | d | | |
| UTC-untreated water check S | 7.1 | a | | |
| 2 Mixotrophic *Chlorella* sp.-Whole Cells DD F | 9.2 | ab | 36% | |
| Mixotrophic *Chlorella* sp.-Whole Cells DD S | 6.3 | abc | −11% | |
| 3 Mixotrophic *Chlorella* sp.-Whole Cells Wet Plot 1 F | 6.2 | d | −8% | −33% |
| Mixotrophic *Chlorella* sp.-Whole Cells Wet Plot 1 S | 5.3 | cdefg | −26% | −16% |
| 4 Mixotrophic *Chlorella* sp.-Whole Cells Wet Plot 2 F | 10.6 | ab | 56% | 15% |
| Mixotrophic *Chlorella* sp.-Whole Cells Wet Plot 2 S | 6.5 | ab | −8% | 3% |
| 5 Grower Standard Product-Acadian Liquid Seaweed Concentrate F | 8.9 | abc | 31% | |
| Grower Standard Product-Acadian Liquid Seaweed Concentrate S | 4.6 | efgh | −35% | |

As shown in Table 35, the foliar treatment comprising wet mixotrophic *Chlorella*-based composition in plot 2 did show a statistically significant increase over the UTC and a numerical increase of 56% regarding whole plant weight. The foliar application of the Acadian product performed lower, showing only a 31% increase over the UTC. The foliar treatment comprising the wet mixotrophic *Chlorella*-based composition in plot 2 did not show a statistically significant difference over the DD mixotrophic *Chlorella*-based composition treatment, but did show a numerical increase of 15%. The foliar treatment in plot 1 and the soil applications comprising wet mixotrophic *Chlorella*-based composition did not show a statistically significant increase over the UTC or DD mixotrophic *Chlorella*-based composition treatment. These results show that small amounts of the mixotrophic *Chlorella*-based composition at a low concentration and low frequency application are effective at improving whole plant weight when applied to the foliage.

TABLE 36

Nursery Tomato Plant Sizing-Root Weight (grams)

| | Avg. | | Increase over UTC | Increase over DD |
|---|---|---|---|---|
| 1 UTC-untreated water check F | 2.2 | bc | | |
| UTC-untreated water check S | 2.8 | a | | |
| 2 Mixotrophic *Chlorella* sp.-Whole Cells DD F | 3.5 | a | 57% | |
| Mixotrophic *Chlorella* sp.-Whole Cells DD S | 2.4 | ab | −11% | |
| 3 Mixotrophic *Chlorella* sp.-Whole Cells Wet Plot 1 F | 1.9 | c | −12% | −46% |
| Mixotrophic *Chlorella* sp.-Whole Cells Wet Plot 1 S | 2.1 | bc | −24% | −13% |

TABLE 36-continued

Nursery Tomato Plant Sizing-Root Weight (grams)

| | | Avg. | | Increase over UTC | Increase over DD |
|---|---|---|---|---|---|
| 4 | Mixotrophic *Chlorella* sp.-Whole Cells Wet Plot 2 F | 3.3 | a | 51% | −6% |
| | Mixotrophic *Chlorella* sp.-Whole Cells Wet Plot 2 S | 1.9 | cd | −30% | −21% |
| 5 | Grower Standard Product-Acadian Liquid Seaweed Concentrate F | 2.8 | ab | 28% | |
| | Grower Standard Product-Acadian Liquid Seaweed Concentrate S | 1.5 | ef | −47% | |

As shown in Table 36, the foliar application of the mixotrophic *Chlorella*-based composition in treatment 4 (wet plot 2) resulted in a significant difference from the UTC regarding root weight, showing an increase of 51% over the UTC. The foliar application of the drum dried mixotrophic *Chlorella*-based composition also resulted in a significant difference from the UTC, with a numerical increase of 57%. The foliar application of the Acadian product performed lower, showing only a 28% increase over the UTC. These results show that small amounts of the mixotrophic *Chlorella*-based composition at a low concentration and low frequency application are effective at improving root weight in plants when applied to the foliage.

TABLE 37

Nursery Tomato Plant Sizing-Shoot Weight (grams)

| | | Avg. | | Increase over UTC | Increase over DD |
|---|---|---|---|---|---|
| 1 | UTC-untreated water check F | 4.6 | cde | | |
| | UTC-untreated water check S | 4.3 | a | | |
| 2 | Mixotrophic *Chlorella* sp.-Whole Cells DD F | 5.9 | bc | 29% | |
| | Mixotrophic *Chlorella* sp.-Whole Cells DD S | 3.9 | abc | −10% | |
| 3 | Mixotrophic *Chlorella* sp.-Whole Cells Wet Plot 1 F | 4.3 | e | −6% | −27% |
| | Mixotrophic *Chlorella* sp.-Whole Cells Wet Plot 1 S | 3.2 | cde | −27% | −18% |
| 4 | Mixotrophic *Chlorella* sp.-Whole Cells Wet Plot 2 F | 7.3 | a | 60% | 24% |
| | Mixotrophic *Chlorella* sp.-Whole Cells Wet Plot 2 S | 4.6 | a | 6% | 18% |
| 5 | Grower Standard Product-Acadian Liquid Seaweed Concentrate F | 6.1 | ab | 33% | |
| | Grower Standard Product-Acadian Liquid Seaweed Concentrate S | 3.1 | cde | −28% | |

As shown in Table 37, the foliar treatment comprising the wet mixotrophic *Chlorella*-based composition in treatment 4 (wet plot 2) showed a statistically significant increase over the UTC and a numerical increase of 60% regarding shoot weight. The Acadian product performed lower, showing only a 33% increase over the UTC in the foliar application, and showing a 28% decrease compared to the UTC in the soil application. The foliar treatment comprising the wet mixotrophic *Chlorella*-based composition in treatment 4 also showed a statistically significant difference over the DD mixotrophic *Chlorella*-based composition treatment and a numerical increase of 24%. Thus, the results indicate that drying the mixotrophic *Chlorella*-based composition with a drum drier in the preparation process reduced the effectiveness of the compositions to enhance the shoot weight of the tomato plants when applied in a foliar application. The foliar application in treatment 3 (wet plot 1) and the soil applications comprising the wet mixotrophic *Chlorella*-based composition did not show a statistically significant increase over the UTC or DD mixotrophic *Chlorella*-based composition treatment, however the soil application in treatment 4 showed an 18% increase over the DD mixotrophic *Chlorella*-based composition treatment. These results show that small amounts of the mixotrophic *Chlorella*-based composition at a low concentration and low frequency application are effective at improving shoot weight in plants when applied to the foliage.

Example 11

An experiment was conducted to determine if the method of application of a low concentration of a mixotrophic *Chlorella*-based composition to green bean seeds (*Phaseolus vulgaris*) planted in soil affected the rate at which the seedlings emerge from the soil and mature. Green beans are part of the Fabaceae family. Green bean seeds were planted in trays with a potting soil mix of sphagnum moss, perlite, and vermiculite (2:1:1). Three treatments comprising a mixotrophic *Chlorella*-based composition were compared to an untreated control (UTC). The treatments were pasteurized, normalized to 10% solids, and stabilized with phosphoric acid ($H_3PO_4$) and potassium sorbate ($C_6H_7KO_2$), with the remaining balance consisting of water. The stored mixotrophic *Chlorella*-based composition was frozen after being harvested from the microalgae culturing system and thawed before formulation in the liquid composition for treatments used in the experiment. The fresh mixotrophic *Chlorella*-based composition was not previously frozen and was incorporated into the liquid composition for treatments used in this experiment directly after being harvested from the microalgae culturing system. The composition used in the treatments of this experiment were not analyzed to quantify bacteria in the compositions, however aerobic plate counts for previous compositions prepared with the same components in the same manner contained 40,000-400,000 CFU/mL.

The mixotrophic *Chlorella*-based liquid composition treatments were applied to the seeds through two different treatment methods. The first treatment method comprised soaking the seeds in the low concentration of 8 mL/gallon of the mixotrophic *Chlorella*-based liquid composition for two hours with constant sparging of air to avoid oxygen deprivation, removing the seeds from the composition, drying the seeds overnight, and then planting the seeds in the potting soil mix. The second treatment method comprised soaking the seeds in water for two hours with constant sparing of air to avoid oxygen deprivation, removing the seeds from water, drying the seeds overnight, planting the seeds in the potting soil mix with the low concentration of 8 mL/gallon of the mixotrophic *Chlorella*-based liquid composition in the base of the planting tray to allow the seeds to be treated with the liquid composition through capillary action. The tested concentration of 8 mL/gallon diluted the composition which originally contained 10% solids by weight of mixotrophic *Chlorella* whole cells to the low percent solids content of only 0.021134%.

Each of the three treatments were applied to 72 seeds. Visual observations of the soil and plants were made daily to record how many seeds had achieved emergence and maturation, as explained below. The standard used for assessing emergence was the achievement of the hypocotyl stage, where a stem was visibly protruding from the potting soil mix. The standard used for assessing maturation was the achievement of the cotyledon stage, where two leaves had visibly formed on the emerged stem. The experiment was conducted indoors with all seeds and treatments subjected to the same controlled conditions including temperature, light, and supply of water. No other nutrients were supplied during the experiment. Light supplied was artificial and provided by fluorescent bulbs 24 hours a day. Results of the experiment are presented in Tables 38-43.

TABLE 38

| | Number of plants emerged by day | | | | | | | |
|---|---|---|---|---|---|---|---|---|
| | 1 | 2 | 3 | 4 | 5 | 6 | 7 | 8 |
| Untreated Control (UTC) | 0 | 0 | 0 | 2 | 23 | 30 | 31 | 33 |
| 10% Mixotrophic *Chlorella* Fresh Soak | 0 | 0 | 0 | 10 | 36 | 41 | 43 | 45 |
| 10% Mixotrophic *Chlorella* Stored Soak | 0 | 0 | 0 | 3 | 33 | 40 | 42 | 42 |
| 10% Mixotrophic *Chlorella* Fresh Capillary | 0 | 0 | 0 | 0 | 10 | 15 | 25 | 34 |

TABLE 39

| | % of total plants emerged by day | | | | | | | |
|---|---|---|---|---|---|---|---|---|
| | 1 | 2 | 3 | 4 | 5 | 6 | 7 | 8 |
| Untreated Control (UTC) | 0 | 0 | 0 | 3 | 32 | 42 | 43 | 46 |
| 10% Mixotrophic *Chlorella* Fresh Soak | 0 | 0 | 0 | 14 | 50 | 57 | 60 | 63 |
| 10% Mixotrophic *Chlorella* Stored Soak | 0 | 0 | 0 | 4 | 46 | 56 | 58 | 58 |
| 10% Mixotrophic *Chlorella* Fresh Capillary | 0 | 0 | 0 | 0 | 14 | 21 | 35 | 47 |

TABLE 40

| | % increase of plants emerged by day over the UTC | | | | | | | |
|---|---|---|---|---|---|---|---|---|
| | 1 | 2 | 3 | 4 | 5 | 6 | 7 | 8 |
| 10% Mixotrophic *Chlorella* Fresh Soak | — | — | — | 400% | 57% | 37% | 39% | 36% |
| 10% Mixotrophic *Chlorella* Stored Soak | — | — | — | 50% | 43% | 33% | 35% | 27% |
| 10% Mixotrophic *Chlorella* Fresh Capillary | — | — | — | −100% | −57% | −50% | −19% | 3% |

As shown in the Tables 38-40, the seed soak treatment for the fresh and stored mixotrophic *Chlorella*-based compositions showed consistently higher performance than the capillary action treatment and the UTC regarding emergence of the plants. The stored mixotrophic *Chlorella*-based composition seed soak treatment showed at least a 27% and as much as a 50% increase over the UTC on comparative days, and the fresh mixotrophic *Chlorella*-based composition seed soak treatment demonstrated at least a 36% and as much as a 400% increase over the UTC. The emergence for the fresh mixotrophic *Chlorella*-based composition consistently outperformed the stored mixotrophic *Chlorella*-based composition in the seed soak treatments, with the difference between the two treatments being the largest on day 4 and narrowing over the duration of the experiment. These results show that a low concentration of a mixotrophic *Chlorella*-based composition is effective in increasing the emergence of a seedling as compared to an untreated seed when applied in a seed soak application.

TABLE 41

| | Number of plants matured by day | | | | | | | |
|---|---|---|---|---|---|---|---|---|
| | 1 | 2 | 3 | 4 | 5 | 6 | 7 | 8 |
| Untreated Control (UTC) | 0 | 0 | 0 | 0 | 0 | 13 | 21 | 27 |
| 10% Mixotrophic Chlorella Fresh Soak | 0 | 0 | 0 | 0 | 0 | 25 | 32 | 37 |
| 10% Mixotrophic Chlorella Stored Soak | 0 | 0 | 0 | 0 | 0 | 13 | 30 | 35 |
| 10% Mixotrophic Chlorella Fresh Capillary | 0 | 0 | 0 | 0 | 0 | 1 | 6 | 15 |

TABLE 42

| | % of total plants matured by day | | | | | | | |
|---|---|---|---|---|---|---|---|---|
| | 1 | 2 | 3 | 4 | 5 | 6 | 7 | 8 |
| Untreated Control (UTC) | 0 | 0 | 0 | 0 | 0 | 18 | 29 | 38 |
| 10% Mixotrophic Chlorella Fresh Soak | 0 | 0 | 0 | 0 | 0 | 35 | 44 | 51 |
| 10% Mixotrophic Chlorella Stored Soak | 0 | 0 | 0 | 0 | 0 | 18 | 42 | 49 |
| 10% Mixotrophic Chlorella Fresh Capillary | 0 | 0 | 0 | 0 | 0 | 1 | 8 | 21 |

TABLE 43

| | % increase of plants matured by day over the UTC | | | | | | | |
|---|---|---|---|---|---|---|---|---|
| | 1 | 2 | 3 | 4 | 5 | 6 | 7 | 8 |
| 10% Mixotrophic Chlorella Fresh Soak | — | — | — | — | — | 92% | 52% | 37% |
| 10% Mixotrophic Chlorella Stored Soak | — | — | — | — | — | 0% | 43% | 30% |
| 10% Mixotrophic Chlorella Fresh Capillary | — | — | — | — | — | -92% | -71% | -44% |

As shown in the Tables 41-43, the seed soak treatment for the fresh and stored mixotrophic Chlorella-based compositions showed consistently higher performance than the capillary action treatment and the UTC regarding maturation of the plants. The stored mixotrophic Chlorella-based composition seed soak treatment showed at least a 30% and as much as a 43% increase over the untreated control on comparative days, and the fresh mixotrophic Chlorella-based composition seed soak treatment demonstrated at least a 37% and as much as a 92% increase over the UTC. The maturation for the fresh mixotrophic Chlorella composition consistently outperformed the stored mixotrophic Chlorella-based composition in the seed soak treatments, with the difference between the two treatments being the largest on 50 day and narrowing over the duration of the experiment. The capillary action treatment was consistently outperformed by the UTC regarding maturation of the plants. These results show that a low concentration of a mixotrophic Chlorella-based composition is effective in increasing the maturation of a seedling as compared to an untreated seed when applied in a seed soak application.

Example 12

An experiment was conducted to determine if the method of application of a low concentration a mixotrophic Chlorella-based composition to green bean seeds (Phaseolus vulgaris) planted in soil affected the rate at which the seedlings emerge from the soil and mature. Green bean seeds were planted in trays with a potting soil mix of sphagnum moss, perlite, and vermiculite (2:1:1). Two treatments comprising a mixotrophic Chlorella-based composition were compared to an untreated control (UTC). The treatments were pasteurized, normalized to 10% solids, and stabilized with phosphoric acid (H3PO4) and potassium sorbate (C6H7KO2), with the remaining balance consisting of water. The mixotrophic Chlorella-based composition was not previously frozen and was incorporated into the liquid composition for treatments used in this experiment directly after being harvested from the microalgae culturing system. The composition used in the treatments of this experiment was not analyzed to quantify bacteria in the composition, however aerobic plate counts for previous compositions prepared with the same components in the same manner contained 40,000-400,000 CFU/mL.

The mixotrophic Chlorella-based liquid composition treatments were applied to the seeds at two different low concentrations, 4.7 mL/gallon or 8 mL/gallon, using the same treatment method. The tested concentration of 4.7 mL/gallon diluted the composition which originally contained 10% solids by weight of mixotrophic Chlorella whole cells to the low percent solids content of only 0.012416%. The tested concentration of 8 mL/gallon diluted the composition which originally contained 10% solids by weight of mixotrophic Chlorella whole cells to the low percent solids content of only 0.021134%. The treatment method consisted of drenching the soil from the top with 0.75 gallon of the liquid composition (equivalent to an application rate of 100 gallons/acre) at the identified concentrations after planting the seeds.

Each of the two treatments were applied to two trays of 72 seeds. Visual observations of the soil and plants were made daily to record how many seeds had achieved emergence and maturation, as explained below. The standard used for assessing emergence was the achievement of the hypocotyl stage where a stem was visibly protruding from the potting soil mix. The standard used for assessing maturation was the achievement of the cotyledon stage where two leaves had visibly formed on the emerged stem. The experiment was conducted indoors with all seeds and treatments subjected to the same controlled conditions including temperature, light, and supply of water. No other nutrients were supplied during the experiment. Light supplied was artificial and provided by fluorescent bulbs 24 hours a day. Results of the experiment are presented in Tables 44-49.

TABLE 44

| | Number of plants emerged by day | | | | | | | | |
|---|---|---|---|---|---|---|---|---|---|
| | 1 | 2 | 3 | 4 | 5 | 6 | 7 | 8 | 9 |
| Untreated Control (UTC) | — | — | 9 | 22 | 32 | 36 | 42 | 46 | 47 |
| 10% Mixotrophic *Chlorella* 4.7 mL | — | — | 11 | 29 | 51 | 58 | 62 | 63 | 64 |
| 10% Mixotrophic *Chlorella* 8 mL | — | — | 13 | 43 | 77 | 91 | 104 | 107 | 110 |

TABLE 45

| | % of total plants emerged by day | | | | | | | | |
|---|---|---|---|---|---|---|---|---|---|
| | 1 | 2 | 3 | 4 | 5 | 6 | 7 | 8 | 9 |
| Untreated Control (UTC) | 0 | 0 | 6 | 15 | 22 | 25 | 29 | 32 | 33 |
| 10% Mixotrophic *Chlorella* 4.7 mL | 0 | 0 | 8 | 20 | 35 | 40 | 43 | 44 | 44 |
| 10% Mixotrophic *Chlorella* 8 mL | 0 | 0 | 9 | 30 | 53 | 63 | 72 | 74 | 76 |

TABLE 46

| | % increase of plants emerged by day over the UTC | | | | | | | | |
|---|---|---|---|---|---|---|---|---|---|
| | 1 | 2 | 3 | 4 | 5 | 6 | 7 | 8 | 9 |
| 10% Mixotrophic *Chlorella* 4.7 mL | — | — | 22% | 32% | 59% | 61% | 48% | 37% | 36% |
| 10% Mixotrophic *Chlorella* 8 mL | — | — | 44% | 95% | 141% | 153% | 148% | 133% | 134% |

As shown in the Tables 44-46, the 8 and 4.7 mL/gallon applications showed consistently higher performance than the UTC regarding emergence of the plants, with the 8 mL/gallon application consistently performing better than the 4.7 mL/gallon. The 4.7 mL/gallon application showed at least a 22% and as much as a 61% increase over the UTC on comparative days, and the 8 mL/gallon application demonstrated at least a 44% and as much as a 153% increase over the UTC. These results show that a low concentration of a mixotrophic *Chlorella*-based composition is effective in increasing the emergence of a seedling as compared to an untreated seed when applied in a soil drench application.

TABLE 47

| | Number of plants matured by day | | | | | | | | |
|---|---|---|---|---|---|---|---|---|---|
| | 1 | 2 | 3 | 4 | 5 | 6 | 7 | 8 | 9 |
| Untreated Control (UTC) | — | — | 0 | 0 | 2 | 14 | 26 | 31 | 34 |
| 10% Mixotrophic *Chlorella* 4.7 mL | — | — | 0 | 0 | 2 | 26 | 52 | 57 | 58 |
| 10% Mixotrophic *Chlorella* 8 mL | — | — | 0 | 0 | 0 | 29 | 60 | 76 | 94 |

TABLE 48

| | % of total plants matured by day | | | | | | | | |
|---|---|---|---|---|---|---|---|---|---|
| | 1 | 2 | 3 | 4 | 5 | 6 | 7 | 8 | 9 |
| Untreated Control (UTC) | 0 | 0 | 0 | 0 | 1 | 10 | 18 | 22 | 24 |
| 10% Mixotrophic *Chlorella* 4.7 mL | 0 | 0 | 0 | 0 | 1 | 18 | 36 | 40 | 40 |
| 10% Mixotrophic *Chlorella* 8 mL | 0 | 0 | 0 | 0 | 0 | 20 | 42 | 53 | 65 |

TABLE 49

| | % increase of plants matured by day over the UTC | | | | | | | | |
|---|---|---|---|---|---|---|---|---|---|
| | 1 | 2 | 3 | 4 | 5 | 6 | 7 | 8 | 9 |
| 10% Mixotrophic *Chlorella* 4.7 mL | — | — | — | — | 0% | 86% | 100% | 84% | 71% |
| 10% Mixotrophic *Chlorella* 8 mL | — | — | — | — | −100% | 107% | 131% | 145% | 176% |

As shown in the Tables 47-49, the 8 and 4.7 mL/gallon applications showed consistently higher performance than the UTC regarding maturation of the plants, with the 8 mL/gallon application consistently performing better than the 4.7 mL/gallon. Starting on day 6, the 4.7 mL/gallon application showed at least a 71% and as much as a 100% increase over the UTC on comparative days and the 8 mL/gallon application demonstrated at least a 107% and as much as a 176% increase over the UTC. The increase in maturation performance for the 8 mL/gallon application over the UTC also increased over time. These results show that a low concentration of a mixotrophic *Chlorella*-based composition is effective in increasing the maturation of a seedling as compared to an untreated seed when applied in a soil drench application.

With the characteristics that are shared among plants within the Fabaceae plant family, the results shown in Examples 11-12 are likely representative as to the effectiveness of mixotrophic *Chlorella*-based composition as described throughout the specification on all plants in the Fabaceae plant family, as well as on plants of other families.

Example 13

An experiment was conducted to determine if a low concentration and low frequency application of a mixotrophic *Chlorella*-based composition to bell pepper plants by soil application affected the yield of the plants. Bell pepper (*Capsicum annuum*) are part of the Solanaceae plant family and seeds were planted in a field in Ventura County, California Two treatments were compared to an untreated control (UTC) and are listed in Table 50. A commercially available macroalgae extract based product was obtained from Acadian Seaplants Limited (30 Brown Avenue, Dartmouth, Nova Scotia, Canada, B3B 1×8) for comparison.

TABLE 50

| Treatment No. | Treatment Description |
|---|---|
| 1 | UTC-untreated water check |
| 2 | Mixotrophic *Chlorella* sp. Cells |
| 3 | Grower Standard Product-Acadian Liquid Seaweed Concentrate |

The mixotrophic *Chlorella*-based composition was pasteurized, normalized to 10% solids, and stabilized with phosphoric acid (H3PO4) and potassium sorbate (C6H7KO2), with the remaining balance consisting of water. The mixotrophic *Chlorella* whole cells were not previously subjected to a purification process to isolate the cells from the microalgae culturing medium, nor were the cells previously subjected to a drying, extraction, or other process that can lyse or disrupt the cell walls. The mixotrophic *Chlorella* composition was previously frozen and thawed, and was incorporated into the liquid composition for treatments used in this experiment after cold storage following being harvested from the microalgae culturing system. The composition comprising mixotrophic *Chlorella* used in the treatments of this experiment were not analyzed to quantify bacteria in the compositions, however aerobic plate counts for previous compositions prepared with the same components in the same manner contained 40,000-400,000 CFU/mL.

The mixotrophic *Chlorella*-based composition was applied at a low concentration of 37.85 mL/gallon. The tested concentration of 37.85 mL/gallon diluted the composition which originally contained 10% solids by weight of mixotrophic *Chlorella* whole cells to the low percent solids content of only 0.099989%. The Acadian treatment was applied at a concentration of 18.9 mL/gallon. Five total treatments were applied at a low frequency (i.e., averaging about 20 days between applications), starting three weeks after plant establishment. The treatments occurred with 20 days between the first and second, 24 days between the second and third, 11 days between the third and fourth, and 26 days between the fourth and fifth. The low concentration and low frequency treatments were applied by injection into a low volume irrigation drip system supplying water at a rate of 100 gallons/acre using a Hypro pump operating at 25 psi.

The experiment was set up as a block designed study of eight replicates consisting of 30 seeds each. Visual observations were used to evaluate plant vigor on a scale of 0-5, with 0 corresponding to plant death and 5 corresponding to complete health. Production was evaluated by quality in the two categories of marketable and unmarketable. Unmarketable fruit was considered fruit which had heavy insect damage, blossom end rot, softness, and/or heavy sunburn. The field used in the experiment was growing bell peppers for processing, and thus the quality needed for fresh market produce was not the target achievement. Additionally, the bell peppers were left in the field a length of time to ensure the maximum amount of reddening before harvest for processing. The chlorophyll content was estimated by an SPAD value (Soil-Plant Analysis Development), a numeric value provided by a Minolta SPAD meter which analyzes the amount of light in a specific light spectrum passing through a leaf and converts that reading to a numerical value as an indicator of chlorophyll density in the leaf. Production was evaluated by sampling based on picking all fruit to be found on two plants and replicating this process eight times per treatment. All fruit was weighed, counted, and reported as grams total weight per two plants and grams total weight on average per fruit. All data rated as significant was done so utilizing the Least Significant Difference analysis at a 90% confidence level, such that values with a statistical significant identifier of the same letter are not significantly different. Results are shown in Tables 51-65 for the treatments designated with an S for soil application, along with accompanying statistical significance identifiers.

Example 14

An experiment was conducted to determine if a low concentration and low frequency application of mixotrophic Chlorella-based composition to bell pepper plants (*Capsicum annuum*) by foliar application affected the yield of the plants. The foliar trial occurred in the same location, with the same treatments, and with the same design as the experiment of Example 13.

The mixotrophic *Chlorella*-based composition was applied at a low concentration of 7 mL/gallon. The tested concentration of 7 mL/gallon diluted the composition which originally contained 10% solids by weight of mixotrophic *Chlorella* whole cells to the low percent solids content of only 0.018492%. The Acadian treatment was applied at a concentration of 18.9 mL/gallon. Five total treatments were applied at a low frequency (i.e., averaging about 21 days between applications), starting three weeks after plant establishment. The treatments occurred with 20 days between the first and second, 23 days between the second and third, 15 days between the third and fourth, and 27 days between the fourth and fifth. The low concentration and low frequency treatments were applied directly to the foliage at a rate of 25 gallons/acre with a backpack sprayer operating at 40 psi through a Hollow Co. nozzle size D-6.

All data rated as significant was done so utilizing the Least Significant Difference analysis at a 90% confidence level, such that values with a statistical significant identifier of the same letter are not significantly different. Results are shown in Tables 51-65 for the treatments designated with an F for foliar application, along with accompanying statistical significance identifiers. It was noted by the time the field was harvested many of the above-mentioned unmarketable quality issues did occur and thus the ratio of unmarketable fruit was higher in this field than one might expect.

TABLE 51

Plant Sizing-Whole plant (grams) (A = early, B = later)

| | | Avg. A | | Increase over UTC | Avg. B | | Increase over UTC |
|---|---|---|---|---|---|---|---|
| 1 | UTC-untreated water check F | 4.3 | a | | 31.2 | a | |
| | UTC-untreated water check S | 4.4 | a | | 24.8 | | |
| 2 | Mixotrophic *Chlorella* sp.-Whole Cells F | 4.6 | a | 6% | 30.9 | a | −1% |
| | Mixotrophic *Chlorella* sp.-Whole Cells S | 4.4 | a | −1% | 26.7 | a | 8% |
| 3 | Grower Standard Product-Acadian Liquid Seaweed Concentrate F | 4.5 | a | 4% | 35.6 | a | 14% |
| | Grower Standard Product-Acadian Liquid Seaweed Concentrate S | 5.1 | a | 17% | 32.7 | a | 32% |

Table 51 shows that there was not statistical significance to the results of the mixotrophic *Chlorella*-based composition treatments compared to the UTC regarding whole plant weight. The foliar application of mixotrophic *Chlorella*-based composition performed better than the soil application at the first measurement and resulted in a 6% increase over the UTC but did not sustain the advantage at the second measurement. The soil application performed better at the second measurement than the foliar application and resulted in an 8% increase over the UTC.

TABLE 52

Plant Sizing-Root (grams) (A = earlier, B = later)

| | | Avg. A | | Increase over UTC | Avg. B | | Increase over UTC |
|---|---|---|---|---|---|---|---|
| 1 | UTC-untreated water check F | 0.6 | a | | 3.4 | a | |
| | UTC-untreated water check S | 0.6 | a | | 3.0 | | |
| 2 | Mixotrophic *Chlorella* sp.-Whole Cells F | 0.6 | a | 7% | 3.3 | a | −4% |
| | Mixotrophic *Chlorella* sp.-Whole Cells S | 0.7 | a | 8% | 3.3 | a | 9% |
| 3 | Grower Standard Product-Acadian Liquid Seaweed Concentrate F | 0.6 | a | 0% | 4.0 | a | 17% |
| | Grower Standard Product-Acadian Liquid Seaweed Concentrate S | 0.7 | a | 8% | 3.6 | a | 21% |

Table 52 shows that there was not statistical significance to the results of the mixotrophic *Chlorella*-based composition treatments compared to the UTC regarding root weight. The foliar and soil applications of mixotrophic *Chlorella*-based composition performed better than the UTC at the first measurement, with 7% and 8% increases over the UTC. The foliar application did not sustain this advantage at the second measurement, but the soil application maintained the advantage showing a 9% increase over the UTC.

TABLE 53

Plant Sizing-Shoot (grams) (A = earlier, B = later)

| | | Avg. A | | Increase over UTC | Avg. B | | Increase over UTC |
|---|---|---|---|---|---|---|---|
| 1 | UTC-untreated water check F | 3.8 | a | | 27.7 | a | |
| | UTC-untreated water check S | 3.7 | a | | 24.0 | | |
| 2 | Mixotrophic *Chlorella* sp.-Whole Cells F | 4.0 | a | 6% | 27.6 | a | 0% |
| | Mixotrophic *Chlorella* sp.-Whole Cells S | 3.7 | a | −2% | 23.5 | a | −2% |
| 3 | Grower Standard Product-Acadian Liquid Seaweed Concentrate F | 3.9 | a | 5% | 31.6 | a | 14% |
| | Grower Standard Product-Acadian Liquid Seaweed Concentrate S | 4.4 | a | 18% | 29.1 | a | 21% |

Table 53 shows that there was not statistical significance to the results of the mixotrophic *Chlorella*-based composition treatments compared to the UTC regarding shoot weight. The foliar application of mixotrophic *Chlorella*-based composition performed better than the UTC and soil application at the first measurement, with a 6% increase over the UTC. The foliar application did not sustain this advantage at the second measurement.

TABLE 54

Average Plant Chlorophyll Content (SPAD)

| | | A | B | | Avg. | Increase Over UTC |
|---|---|---|---|---|---|---|
| 1 | UTC-untreated water check F | 64.7 | — | 39.7 a | 52.5 | |
| | UTC-untreated water check S | | — | 69.7 ab | 69.7 | |
| 2 | Mixotrophic *Chlorella* sp.-Whole Cells F | 71.5 | — | 36.4 a | 54.0 | 3% |
| | Mixotrophic *Chlorella* sp.-Whole Cells S | | — | 70.2 ab | 70.2 | 1% |
| 3 | Grower Standard Product-Acadian Liquid Seaweed Concentrate F | 70.6 | — | 35.4 a | 53.0 | 2% |
| | Grower Standard Product-Acadian Liquid Seaweed Concentrate S | | — | 64.5 a | 64.5 | −7% |

Table 54 shows that there was not statistical significance to the results of the mixotrophic *Chlorella*-based composition treatments compared to the UTC regarding chlorophyll content. The foliar and soil applications of mixotrophic *Chlorella*-based composition performed within 3% of the UTC.

TABLE 55

Average Plant Vigor (Visual Scale 0-5)

|   | | A | | B | | C | | Avg. | Increase over UTC |
|---|---|---|---|---|---|---|---|---|---|
| 1 | UTC-untreated water check F | 3.4 | a | 4.5 | a | 4.0 | a | 4.0 | |
|   | UTC-untreated water check S | 3.5 | a | 4.5 | a | | | 4.0 | |
| 2 | Mixotrophic *Chlorella* sp.-Whole Cells F | 3.2 | a | 4.1 | a | 4.0 | a | 3.8 | −5% |
|   | Mixotrophic *Chlorella* sp.-Whole Cells S | 4.0 | a | 4.0 | a | | | 4.0 | 0% |
| 3 | Grower Standard Product-Acadian Liquid Seaweed Concentrate F | 3.2 | a | 4.3 | a | 4.0 | a | 3.8 | −3% |
|   | Grower Standard Product-Acadian Liquid Seaweed Concentrate S | 3.5 | a | 4.0 | a | | | 3.8 | −6% |

Table 55 shows that there was not statistical significance to the results of the mixotrophic *Chlorella*-based composition treatments compared to the UTC regarding plant vigor, nor was there a numerical advantage.

TABLE 56

Total Unmarketable Plant Weight per Plot (grams)

| | Avg. | | Increase over UTC |
|---|---|---|---|
| 1 UTC-untreated water check F | 1895.0 | a | |
| UTC-untreated water check S | 963.8 | a | |
| 2 Mixotrophic *Chlorella* sp.-Whole Cells F | 1803.1 | a | −5% |
| Mixotrophic *Chlorella* sp.-Whole Cells S | 179.4 | b | −81% |
| 3 Grower Standard Product-Acadian Liquid Seaweed Concentrate F | 1580.6 | a | −17% |
| Grower Standard Product-Acadian Liquid Seaweed Concentrate S | 66.9 | b | −93% |

Table 56 shows that the soil application of the mixotrophic *Chlorella*-based composition had a statistically significant decrease in unmarketable plant weight compared to the UTC, and the foliar application results were not statistically significant compared to the UTC.

TABLE 57

Total Unmarketable Plant Yield per Plot (number)

| | Avg. | | Increase over UTC |
|---|---|---|---|
| 1 UTC-untreated water check F | 10.8 | a | |
| UTC-untreated water check S | 6.0 | a | |
| 2 Mixotrophic *Chlorella* sp.-Whole Cells F | 9.8 | a | −9% |
| Mixotrophic *Chlorella* sp.-Whole Cells S | 1.9 | b | −69% |
| 3 Grower Standard Product-Acadian Liquid Seaweed Concentrate F | 9.1 | a | −15% |
| Grower Standard Product-Acadian Liquid Seaweed Concentrate S | 1.1 | b | −81% |

Table 57 shows that the soil application of the mixotrophic *Chlorella*-based composition had a statistically significant decrease in unmarketable plant yield compared to the UTC, and the foliar application results were not statistically significant compared to the UTC.

TABLE 58

Total Unmarketable Fruit Weight per Plot (grams)

| | Avg. | | Increase over UTC |
|---|---|---|---|
| 1 UTC-untreated water check F | 178.5 | a | |
| UTC-untreated water check S | 56.2 | a | |
| 2 Mixotrophic *Chlorella* sp.-Whole Cells F | 182.8 | a | 2% |
| Mixotrophic *Chlorella* sp.-Whole Cells S | 57.6 | a | 2% |
| 3 Grower Standard Product-Acadian Liquid Seaweed Concentrate F | 173.2 | a | −3% |
| Grower Standard Product-Acadian Liquid Seaweed Concentrate S | 35.3 | a | −37% |

Table 58 shows that the soil and foliar applications of the mixotrophic *Chlorella*-based composition were not statistically significant compared to the UTC for unmarketable fruit weight, but both showed a numerical increase of 2% over the UTC. The soil application of mixotrophic *Chlorella*-based composition also outperformed the Acadian product, which showed a 37% decrease compared to the UTC.

TABLE 59

Total Marketable Plant Weight per Plot (grams)

| | Avg. | | Increase over UTC |
|---|---|---|---|
| 1 UTC-untreated water check F | 120.6 | a | |
| UTC-untreated water check S | 317.5 | c | |
| 2 Mixotrophic *Chlorella* sp.-Whole Cells F | 386.3 | a | 220% |
| Mixotrophic *Chlorella* sp.-Whole Cells S | 1224.4 | a | 286% |
| 3 Grower Standard Product-Acadian Liquid Seaweed Concentrate F | 502.5 | a | 317% |
| Grower Standard Product-Acadian Liquid Seaweed Concentrate S | 1233.1 | a | 288% |

Table 59 shows that the results of the soil application of the mixotrophic *Chlorella*-based composition were statistically significant compared to the UTC for marketable plant weight, and both soil and foliar applications showed large numerical increases of 286% and 220% over the UTC, which was comparable with the commercially successful Acadian product. These results show that small amounts of the mixotrophic *Chlorella*-based composition at a low concentration and low frequency application are effective for not only improving plant weight, put improving plant weight in the higher quality plants (i.e., marketable) when applied to the soil or foliage.

TABLE 60

Total Marketable Plant Yield per Plot (number)

|   |   | Avg. |   | Increase over UTC |
|---|---|------|---|-------------------|
| 1 | UTC-untreated water check F | 0.6 | a |  |
|   | UTC-untreated water check S | 2.3 | a |  |
| 2 | Mixotrophic *Chlorella* sp.-Whole Cells F | 2.0 | a | 220% |
|   | Mixotrophic *Chlorella* sp.-Whole Cells S | 6.8 | a | 200% |
| 3 | Grower Standard Product-Acadian Liquid Seaweed Concentrate F | 2.8 | a | 340% |
|   | Grower Standard Product-Acadian Liquid Seaweed Concentrate S | 7.1 | a | 217% |

Table 60 shows that the results of the soil and foliar applications of the mixotrophic *Chlorella*-based composition showed large numerical increases of 200% and 220% over the UTC, which was comparable with the commercially successful Acadian product. These results show that small amounts of the mixotrophic *Chlorella*-based composition at a low concentration and low frequency application are effective for not only improving plant yield, put improving plant yield in the higher quality plants (i.e., marketable) when applied to the soil or foliage.

TABLE 61

Total Marketable Fruit Weight per Plot (grams)

|   | Avg. |   | Increase over UTC |
|---|------|---|-------------------|
| 1 UTC-untreated water check F | 73.1 | a |  |
| UTC-untreated water check S | 123.7 | b |  |
| 2 Mixotrophic *Chlorella* sp.-Whole Cells F | 43.8 | a | −40% |
| Mixotrophic *Chlorella* sp.-Whole Cells S | 182.9 | a | 48% |
| 3 Grower Standard Product-Acadian Liquid Seaweed Concentrate F | 115.8 | a | 58% |
| Grower Standard Product-Acadian Liquid Seaweed Concentrate S | 66.9 | a | −46% |

Table 61 shows that the results of the soil application of the mixotrophic *Chlorella*-based composition were statistically significant compared to the UTC for marketable fruit weight. The soil application of mixotrophic *Chlorella*-based composition also showed a numerical increase of 48% over the UTC. The soil application of *Chlorella*-based composition also outperformed the Acadian product, which showed a 46% decrease compared to the UTC. These results show that small amounts of the mixotrophic *Chlorella*-based composition at a low concentration and low frequency application are effective for not only improving fruit weight but improving fruit weight in the higher quality plants (i.e., marketable) when applied to the soil.

TABLE 62

Total Production Plant Weight per Plot (grams)

|   | Avg. |   | Increase over UTC |
|---|------|---|-------------------|
| 1 UTC-untreated water check F | 2015.6 | a |  |
| UTC-untreated water check S | 656.3 | c |  |
| 2 Mixotrophic *Chlorella* sp.-Whole Cells F | 2189.4 | a | 9% |
| Mixotrophic *Chlorella* sp.-Whole Cells S | 1403.8 | a | 114% |
| 3 Grower Standard Product-Acadian Liquid Seaweed Concentrate F | 2083.1 | a | 3% |
| Grower Standard Product-Acadian Liquid Seaweed Concentrate S | 1300.0 | a | 98% |

Table 62 shows that the results of the soil application of the mixotrophic *Chlorella*-based composition were statistically significant compared to the UTC for production plant weight. The soil application of mixotrophic *Chlorella*-based composition also showed a numerical increase of 114% over the UTC, with the foliar application showing a 9% increase over the UTC, which were both comparable to the Acadian product. These results show that small amounts of the mixotrophic *Chlorella*-based composition at a low concentration and low frequency application are effective for not only total production plant weight when applied to the soil.

TABLE 63

Total Production Plant Yield per Plot (number)

|   | Avg. |   | Increase over UTC |
|---|------|---|-------------------|
| 1 UTC-untreated water check F | 11.4 | a |  |
| UTC-untreated water check S | 8.3 | a |  |
| 2 Mixotrophic *Chlorella* sp.-Whole Cells F | 11.8 | a | 3% |
| Mixotrophic *Chlorella* sp.-Whole Cells S | 8.6 | a | 5% |
| 3 Grower Standard Product-Acadian Liquid Seaweed Concentrate F | 11.9 | a | 4% |
| Grower Standard Product-Acadian Liquid Seaweed Concentrate S | 8.3 | a | 0% |

Table 63 shows that the results of the soil and foliar applications of the mixotrophic *Chlorella*-based composition were not statistically significant compared to the UTC for production plant yield but did show numerical increases of 5% and 3% over the UTC.

TABLE 64

Average Production Fruit Weight per Plot (grams)

|   | Avg. |   | Increase over UTC |
|---|------|---|-------------------|
| 1 UTC-untreated water check F | 179.0 | a |  |
| UTC-untreated water check S | 80.5 | b |  |
| 2 Mixotrophic *Chlorella* sp.-Whole Cells F | 189.6 | a | 6% |
| Mixotrophic *Chlorella* sp.-Whole Cells S | 167.0 | a | 107% |
| 3 Grower Standard Product-Acadian Liquid Seaweed Concentrate F | 174.1 | a | −3% |
| Grower Standard Product-Acadian Liquid Seaweed Concentrate S | 159.8 | a | 98% |

Table 64 shows that the results of the soil application of the mixotrophic *Chlorella*-based composition were statistically significant compared to the UTC for production fruit weight. The soil application of mixotrophic *Chlorella*-based composition also showed a numerical increase of 117% over the UTC, with the foliar application showing a 6% increase over the UTC, both of which were comparable to the Acadian product. These results show that small amounts of the mixotrophic *Chlorella*-based composition at a low concentration and low frequency application are effective for not only total production fruit weight when applied to the soil or foliage.

TABLE 65

Utilization (%, ratio of marketable fruit to total fruit produced by weight)

| | | Avg. | | Increase over UTC |
|---|---|---|---|---|
| 1 | UTC-untreated water check F | 6.5 | a | |
| | UTC-untreated water check S | 45.0 | b | |
| 2 | Mixotrophic *Chlorella* sp.-Whole Cells F | 11.8 | a | 81% |
| | Mixotrophic *Chlorella* sp.-Whole Cells S | 88.3 | a | 96% |
| 3 | Grower Standard Product-Acadian Liquid Seaweed Concentrate F | 18.3 | a | 181% |
| | Grower Standard Product-Acadian Liquid Seaweed Concentrate S | 94.6 | a | 110% |

Table 65 shows that the results of the soil application of the mixotrophic *Chlorella*-based composition were statistically significant compared to the UTC for utilization percentage (ratio of marketable fruit to total fruit produced by weight). The soil application of mixotrophic *Chlorella*-based composition also showed a numerical increase of 96% over the UTC, with the foliar application showing an 81% increase over the UTC. These results show that small amounts of the mixotrophic *Chlorella*-based composition at a low concentration and low frequency application are effective for improving the total quality of the field when applied to the soil or foliage.

Example 15

An experiment was conducted to determine if a low concentration and low frequency application of a mixotrophic *Chlorella*-based composition to gavilon tomato plants (*Solanum lycopersicum*) by soil application affected the yield of the plants. Tomatoes are also members of the Solanaceae plant family. The soil application trial occurred in the same location, with the same treatments, and with the same design as the experiment of Example 13. The tomato plants were grown as a bush on the ground for this experiment.

The mixotrophic *Chlorella*-based composition was applied at a low concentration of 37.85 mL/gallon. The tested concentration of 37.85 mL/gallon diluted the composition which originally contained 10% solids by weight of mixotrophic *Chlorella* whole cells to the low percent solids content of only 0.099989%. The Acadian treatment was applied at a concentration of 18.9 mL/gallon. Five total treatments were applied at a low frequency (i.e., averaging about 23 days between applications), starting three weeks after plant establishment. The treatments occurred with 19 days between the first and second, 29 days between the second and third, 23 days between the third and fourth, and 21 days between the fourth and fifth. The low concentration and low frequency treatments were applied by injection into a low volume irrigation drip system at a rate of 100 gallons/acre using a Hypro pump operating at 25 psi.

All data rated as significant was done so utilizing the Least Significant Difference analysis at a 90% confidence level, such that values with a statistical significant identifier of the same letter are not significantly different. Results are shown in tables 66-78 for the treatments designated with an S for soil application, along with accompanying statistical significance identifiers.

Example 16

An experiment was conducted to determine if a low concentration and low frequency application of mixotrophic *Chlorella*-based composition to gavilon tomato plants (*Solanum lycopersicum*) by foliar application affected the yield of the plants. The foliar trial occurred in the same location, with the same treatments, and with the same design as the experiment of Example 14. The tomato plants were grown on stakes for this experiment.

The mixotrophic *Chlorella*-based composition was applied at a low concentration of 7 mL/gallon. The tested concentration of 7 mL/gallon diluted the composition which originally contained 10% solids by weight of mixotrophic *Chlorella* whole cells to the low percent solids content of only 0.018492%. The Acadian treatment was applied at a concentration of 18.9 mL/gallon. Five total treatments were applied at a low frequency (i.e., averaging about 21 days between applications), starting three weeks after plant establishment. The treatments occurred with 19 days between the first and second, 21 days between the second and third, 23 days between the third and fourth, and 21 days between the fourth and fifth. The low concentration and low frequency treatments were applied directly to the foliage at a rate of 25 gallons/acre with a backpack sprayer operating at 40 psi through a Hollow Co. nozzle size D-6.

All data rated as significant was done so utilizing the Least Significant Difference analysis at a 90% confidence level, such that values with a statistical significant identifier of the same letter are not significantly different. Results are shown in tables 66-78 for the treatments designated with an F for foliar application, along with accompanying statistical significance identifiers.

TABLE 66

Average Plant Chlorophyll Content (SPAD)

| | | A | | B | | Avg. | Increase over UTC |
|---|---|---|---|---|---|---|---|
| 1 | UTC-untreated water check F | 52.7 | a | 48.0 | a | 50.4 | |
| | UTC-untreated water check S | 44.6 | a | | | 44.6 | |
| 2 | Mixotrophic *Chlorella* sp.-Whole Cells F | 54.6 | a | 45.4 | a | 50.0 | −1% |
| | Mixotrophic *Chlorella* sp.-Whole Cells S | 44.5 | a | | | 44.5 | 0% |
| 3 | Grower Standard Product-Acadian Liquid Seaweed Concentrate F | 53.9 | a | 46.2 | a | 50.1 | −1% |
| | Grower Standard Product-Acadian Liquid Seaweed Concentrate S | 41.8 | a | | | 41.8 | −6% |

Table 66 shows that there was not statistical significance to the results of the mixotrophic *Chlorella*-based composition treatments compared to the UTC regarding chlorophyll content, nor a numerical increase.

TABLE 67

Average Plant Vigor (Visual Scale 0-5)

|   | | A | | B | | Avg. | Increase over UTC |
|---|---|---|---|---|---|---|---|
| 1 | UTC-untreated water check F | 4.9 | a | 3.9 | a | 4.4 | |
|   | UTC-untreated water check S | 4.2 | a | | | 4.2 | |
| 2 | Mixotrophic *Chlorella* sp.-Whole Cells F | 5.0 | a | 3.6 | a | 4.3 | −2% |
|   | Mixotrophic *Chlorella* sp.-Whole Cells S | 4.5 | a | | | 4.5 | 7% |
| 3 | Grower Standard Product-Acadian Liquid Seaweed Concentrate F | 4.9 | a | 4.1 | a | 4.5 | 2% |
|   | Grower Standard Product-Acadian Liquid Seaweed Concentrate S | 4.1 | a | | | 4.1 | −2% |

Table 67 shows that there was not statistical significance to the results of the mixotrophic *Chlorella*-based composition treatments compared to the UTC regarding plant vigor, however the soil application showed a 7% increase over the UTC.

TABLE 68

Total Unmarketable Plant Weight per Plot (grams)

|   | | Avg. | | Increase over UTC |
|---|---|---|---|---|
| 1 | UTC-untreated water check F | 205.8 | a | |
|   | UTC-untreated water check S | 2156.0 | a | |
| 2 | Mixotrophic *Chlorella* sp.-Whole Cells F | 139.2 | a | −32% |
|   | Mixotrophic *Chlorella* sp.-Whole Cells S | 2279.2 | a | 6% |
| 3 | Grower Standard Product-Acadian Liquid Seaweed Concentrate F | 162.5 | a | −21% |
|   | Grower Standard Product-Acadian Liquid Seaweed Concentrate S | 997.5 | b | −54% |

Table 68 shows that the application of the mixotrophic *Chlorella*-based composition did not have a statistically significant decrease in unmarketable plant weight compared to the UTC, however the foliar application showed a 32% decrease over the UTC. The soil application of mixotrophic *Chlorella*-based composition showed a 6% increase over the UTC, while the commercially successful Acadian product soil application showed a 54% decrease.

TABLE 69

Total Unmarketable Plant Yield per Plot (number)

|   | | Avg. | | Increase over UTC |
|---|---|---|---|---|
| 1 | UTC-untreated water check F | 5.8 | a | |
|   | UTC-untreated water check S | 49.3 | a | |
| 2 | Mixotrophic *Chlorella* sp.-Whole Cells F | 3.0 | a | −49% |
|   | Mixotrophic *Chlorella* sp.-Whole Cells S | 47.7 | a | −3% |
| 3 | Grower Standard Product-Acadian Liquid Seaweed Concentrate F | 3.0 | a | −49% |
|   | Grower Standard Product-Acadian Liquid Seaweed Concentrate S | 28.5 | bc | −42% |

Table 69 shows that the application of the mixotrophic *Chlorella*-based composition did not have a statistically significant decrease in unmarketable plant yield compared to the UTC, however the foliar application showed a 49% decrease and the soil application showed a 3% decrease with respect to the UTC, which was smaller than the 42% decrease of the Acadian product soil application.

TABLE 70

Total Unmarketable Fruit Weight per Plot (grams)

|   | | Avg. | | Increase over UTC |
|---|---|---|---|---|
| 1 | UTC-untreated water check F | 29.6 | a | |
|   | UTC-untreated water check S | 45.8 | a | |
| 2 | Mixotrophic *Chlorella* sp.-Whole Cells F | 27.5 | a | −7% |
|   | Mixotrophic *Chlorella* sp.-Whole Cells S | 47.4 | a | 3% |
| 3 | Grower Standard Product-Acadian Liquid Seaweed Concentrate F | 35.5 | a | 20% |
|   | Grower Standard Product-Acadian Liquid Seaweed Concentrate S | 34.8 | a | −24% |

Table 70 shows that the soil and foliar applications of the mixotrophic *Chlorella*-based composition were not statistically significant compared to the UTC for unmarketable fruit weight, but the soil application showed a 3% increase, while the Acadian product showed a 24% decrease, and the foliar application showed a 7% decrease with respect to the UTC.

TABLE 71

Total Marketable Plant Weight per Plot (grams)

|   | | Avg. | | Increase over UTC |
|---|---|---|---|---|
| 1 | UTC-untreated water check F | 8702.5 | a | |
|   | UTC-untreated water check S | 7616.7 | a | |
| 2 | Mixotrophic *Chlorella* sp.-Whole Cells F | 8317.5 | a | −4% |
|   | Mixotrophic *Chlorella* sp.-Whole Cells S | 8160.8 | a | 7% |
| 3 | Grower Standard Product-Acadian Liquid Seaweed Concentrate F | 7731.7 | a | −11% |
|   | Grower Standard Product-Acadian Liquid Seaweed Concentrate S | 7828.3 | a | 3% |

Table 71 shows that the results of the application of the mixotrophic *Chlorella*-based composition were not statistically significant compared to the UTC for marketable plant weight, however the soil application showed a 7% increase over the UTC.

TABLE 72

Total Marketable Plant Yield per Plot (number)

|   | | Avg. | | Increase over UTC |
|---|---|---|---|---|
| 1 | UTC-untreated water check F | 120.8 | a | |
|   | UTC-untreated water check S | 103.5 | a | |
| 2 | Mixotrophic *Chlorella* sp.-Whole Cells F | 103.0 | a | −15% |
|   | Mixotrophic *Chlorella* sp.-Whole Cells S | 115.3 | a | 11% |
| 3 | Grower Standard Product-Acadian Liquid Seaweed Concentrate F | 107.7 | a | −11% |
|   | Grower Standard Product-Acadian Liquid Seaweed Concentrate S | 118.0 | a | 14% |

Table 72 shows that the results of the soil and foliar applications of the mixotrophic *Chlorella*-based composition were not statistically significant compared to the UTC for marketable plant yield, however the soil application showed an 11% increase over the UTC.

TABLE 73

Total Marketable Fruit Weight per Plot (grams)

| | Avg. | | Increase over UTC |
|---|---|---|---|
| 1 UTC-untreated water check F | 72.2 | b | |
| UTC-untreated water check S | 74.5 | a | |
| 2 Mixotrophic Chlorella sp.-Whole Cells F | 80.5 | a | 11% |
| Mixotrophic Chlorella sp.-Whole Cells S | 70.1 | a | −6% |
| 3 Grower Standard Product-Acadian Liquid Seaweed Concentrate F | 72.0 | b | 0% |
| Grower Standard Product-Acadian Liquid Seaweed Concentrate S | 65.7 | a | −12% |

Table 73 shows that the results of the foliar application of the mixotrophic Chlorella-based composition were statistically significant compared to the UTC and Acadian product for marketable fruit weight and resulted in an 11% increase over the UTC. These results show that small amounts of the mixotrophic Chlorella-based composition at a low concentration and low frequency application are effective for not only improving fruit weight, put improving fruit weight in the higher quality plants (i.e., marketable) when applied to the foliage.

TABLE 74

Total Production Plant Weight per Plot (grams)

| | Avg. | | Increase over UTC |
|---|---|---|---|
| 1 UTC-untreated water check F | 8908.3 | a | |
| UTC-untreated water check S | 9272.7 | a | |
| 2 Mixotrophic Chlorella sp.-Whole Cells F | 8456.7 | a | −5% |
| Mixotrophic Chlorella sp.-Whole Cells S | 10440.0 | a | 13% |
| 3 Grower Standard Product-Acadian Liquid Seaweed Concentrate F | 7894.2 | a | −11% |
| Grower Standard Product-Acadian Liquid Seaweed Concentrate S | 8825.8 | a | −5% |

Table 74 shows that the results of the soil application of the mixotrophic Chlorella-based composition were not statistically significant compared to the UTC for production plant weight, however the soil application resulted in a numerical increase of 13% over the UTC while the Acadian product showed a 5% decrease.

TABLE 75

Total Production Plant Yield per Plot (number)

| | Avg. | | Increase over UTC |
|---|---|---|---|
| 1 UTC-untreated water check F | 126.7 | a | |
| UTC-untreated water check S | 152.8 | ab | |
| 2 Mixotrophic Chlorella sp.-Whole Cells F | 110.2 | a | −13% |
| Mixotrophic Chlorella sp.-Whole Cells S | 163.0 | a | 7% |
| 3 Grower Standard Product-Acadian Liquid Seaweed Concentrate F | 110.7 | a | −13% |
| Grower Standard Product-Acadian Liquid Seaweed Concentrate S | 146.5 | abc | −4% |

Table 75 shows that the results of the soil and foliar applications of the mixotrophic Chlorella-based composition were not statistically significant compared to the UTC for production plant yield, but the soil application showed an increase of 7% over the UTC, with the Acadian product showing a 4% decrease.

TABLE 76

Average Production Fruit Weight per Plot (grams)

| | Avg. | | Increase over UTC |
|---|---|---|---|
| 1 UTC-untreated water check F | 70.7 | a | |
| UTC-untreated water check S | 64.8 | a | |
| 2 Mixotrophic Chlorella sp.-Whole Cells F | 76.7 | a | 9% |
| Mixotrophic Chlorella sp.-Whole Cells S | 63.1 | a | −3% |
| 3 Grower Standard Product-Acadian Liquid Seaweed Concentrate F | 71.6 | a | 1% |
| Grower Standard Product-Acadian Liquid Seaweed Concentrate S | 59.4 | a | −8% |

Table 76 shows that the results of the foliar application of the mixotrophic Chlorella-based composition were not statistically significant compared to the UTC for production fruit weight, however the foliar application showed a numerical increase of 9% over the UTC.

TABLE 77

Utilization (%, the ratio of marketable fruit to total fruit produced by weight)

| | Avg. | | Increase over UTC |
|---|---|---|---|
| 1 UTC-untreated water check F | 97.5 | a | |
| UTC-untreated water check S | 76.8 | c | |
| 2 Mixotrophic Chlorella sp.-Whole Cells F | 98.3 | a | 1% |
| Mixotrophic Chlorella sp.-Whole Cells S | 77.2 | c | 0% |
| 3 Grower Standard Product-Acadian Liquid Seaweed Concentrate F | 98.0 | a | 1% |
| Grower Standard Product-Acadian Liquid Seaweed Concentrate S | 88.7 | a | 15% |

Table 77 shows that the results of the application of the mixotrophic Chlorella-based composition were not statistically significant compared to the UTC for utilization percentage (ratio of marketable fruit to total fruit produced by weight).

With the characteristics that are shared among plants within the Solanaceae plant family, the results shown in the Examples 6-10 and 13-16, are likely representative as to the effectiveness of a mixotrophic Chlorella-based composition as described by throughout the specification on all plants in the Solanaceae plant family, as well as plants in other families.

Example 17

Figures 3, 4:
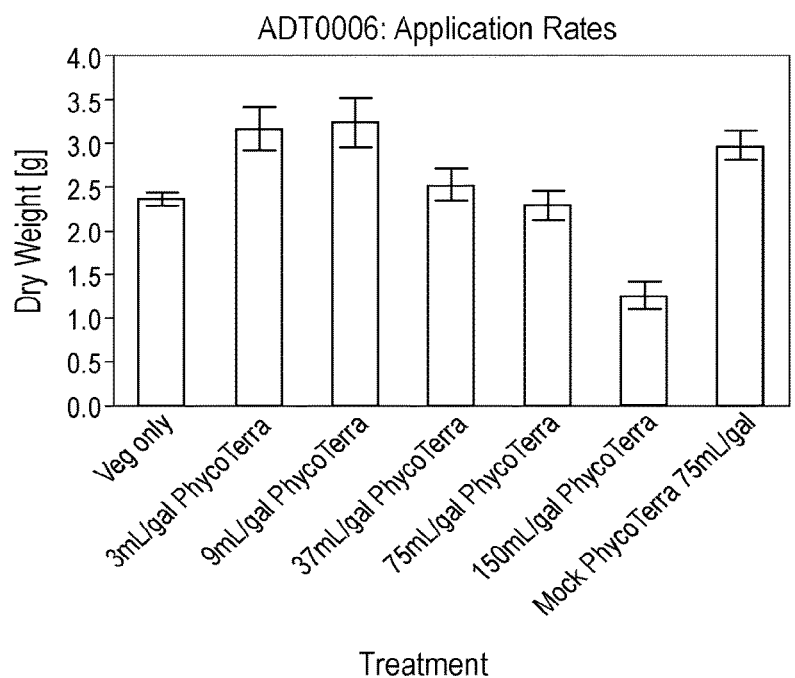
FIG. 3 depicts the results of various pasteurization conditions of the composition.
FIG. 4 depicts the results of various application rates of the composition.

An experiment was conducted to determine the effects of different application rates of a low concentration mixotrophic Chlorella-based composition (designated as "PT" or as "PhycoTerra" in various Figure legends throughout this disclosure) on plants. Under hydroponic conditions, the composition was applied between 3 mL/gal-150 mL/gal. A nutrient only mock composition was also tested. The mock composition contained only non-biological components. All treatment conditions included fertilizer. The control was a fertilizer only treatment (Veg only). The experiment demonstrated that the composition has biological effects on plants at low concentrations. The results of the experiment are shown in FIG. 4.

Example 18

Figure 5A:
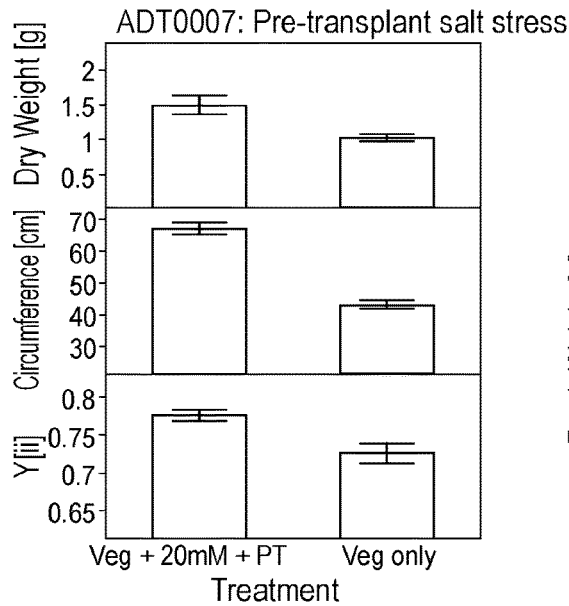
FIGS. 5A-5F depict graphs of the results of the composition on salt-stressed plants.
Figure 5B:
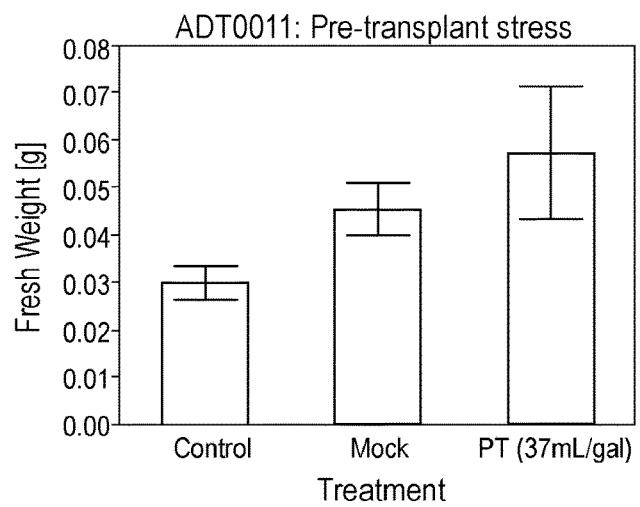
Figure 5C:
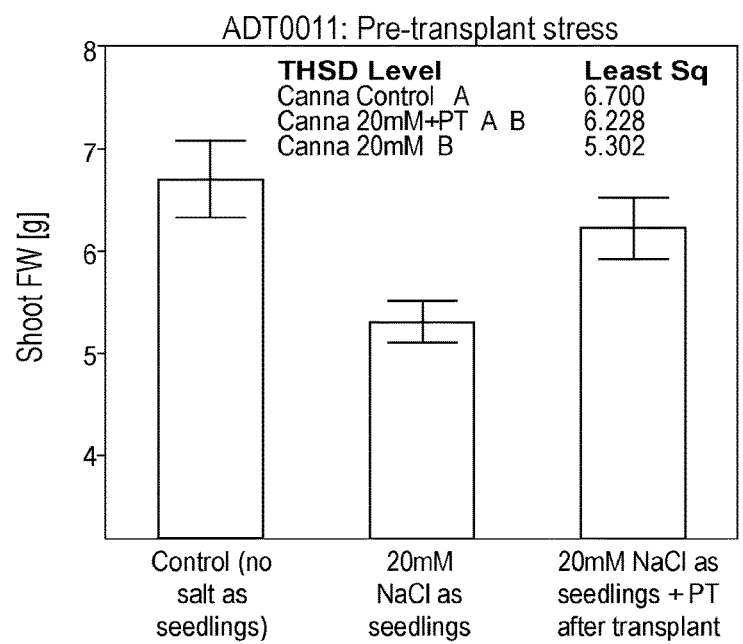
Figure 5D:
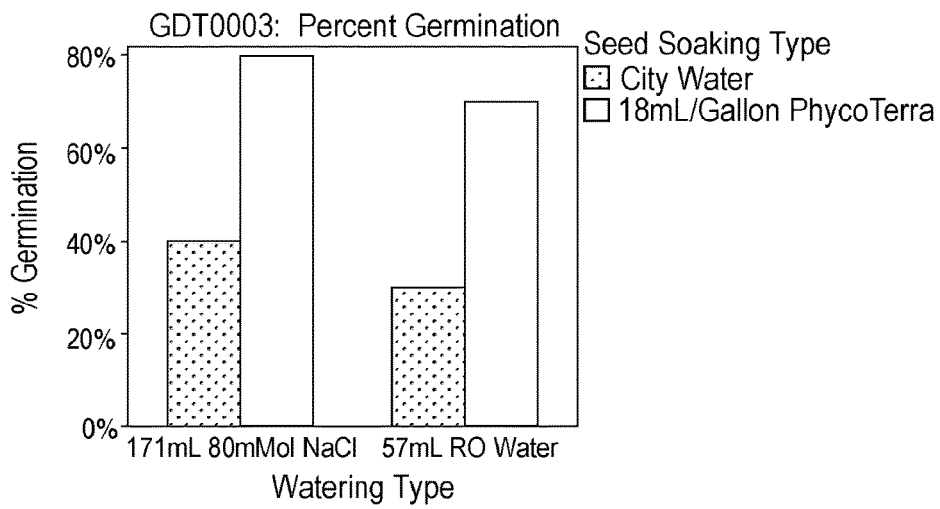
Figure 5E:
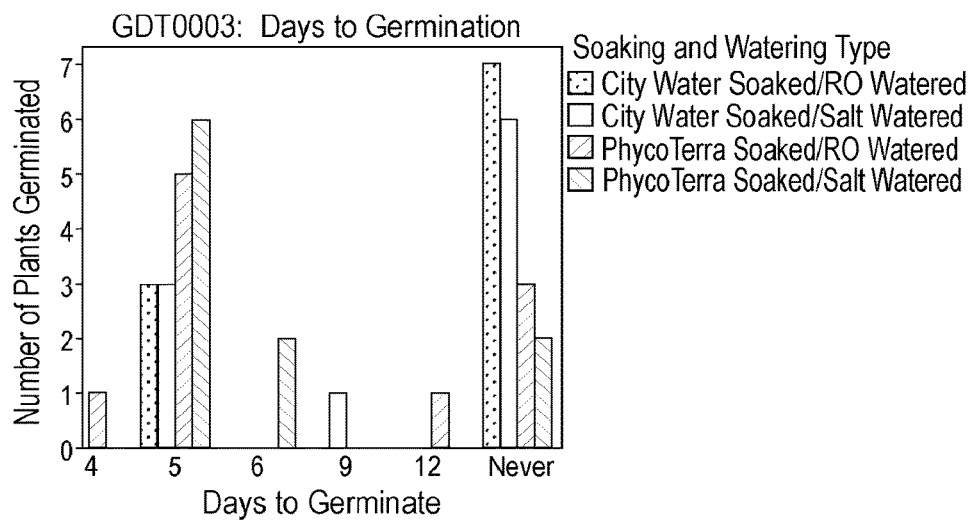
Figure 5F:
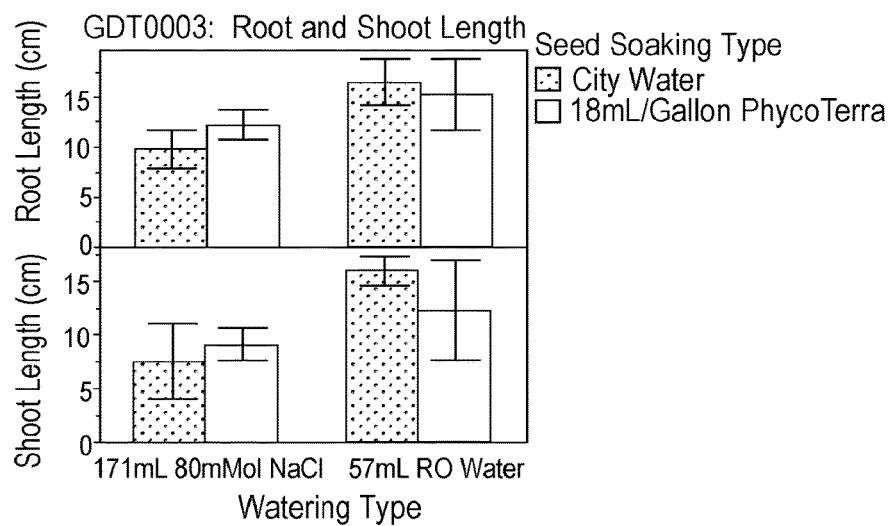

Experiments were conducted to determine if application of a low concentration mixotrophic Chlorella-based composition to plants that were salt-stressed at time of seeding affected the yield of the plants. Results of such experiments are shown in FIG. 5A-5F. In one experiment, pole beans were soaked in city water or 18 mL/gallon of the microalgae-based composition for four hours. The seeds were planted in coco (an inert coconut fiber medium) and grown in a hydroponics platform. Seeds were planted (without washing) in a randomized fashion and treated with 80 mMol salt the first day. To test the importance of run-off (RO), half of each seed soaking type was either watered with 57 mL of RO water (full saturation), or 171 mL of 80 mMol salt solution (Heavy run-off). Some cells contained just the coco and were harvested to look at salinity profile in the coco with and without run off. Effects of the treatments were assessed by measuring dry weight, circumference, and photosynthetic yield (Y[ii]) (FIG. 5A). Total fresh weight (FIG. 5B) and shoot weight (FIG. 5C) were also assessed. The results also show that seeds soaked in the mixotrophic *Chlorella*-based composition before planting had a 40% increase in germination rate (FIG. 5D). In addition, seeds soaked in the mixotrophic *Chlorella*-based composition germinated earlier than seeds soaked in City Water, and seeds watered with RO water to full saturation had a decrease in germination compared to seeds watered with 80 mMol salt solution with heavy run-off (FIG. 5E).

Example 19

An experiment was conducted to determine if an application of a low concentration mixotrophic *Chlorella*-based composition (PT) to plants that were drought stressed at time of seeding affected the yield of the plants. The conditions were (1) controls: outside heat but saturated, (2) no water+outside heat, and (3) no water+outside heat+I hr sun. Results of the experiment show that plants treated with PT showed no detrimental effects when exposed to drought and sun whereas plants with no PT treatment reacted to drought and sun.

Example 20

Figure 6A:
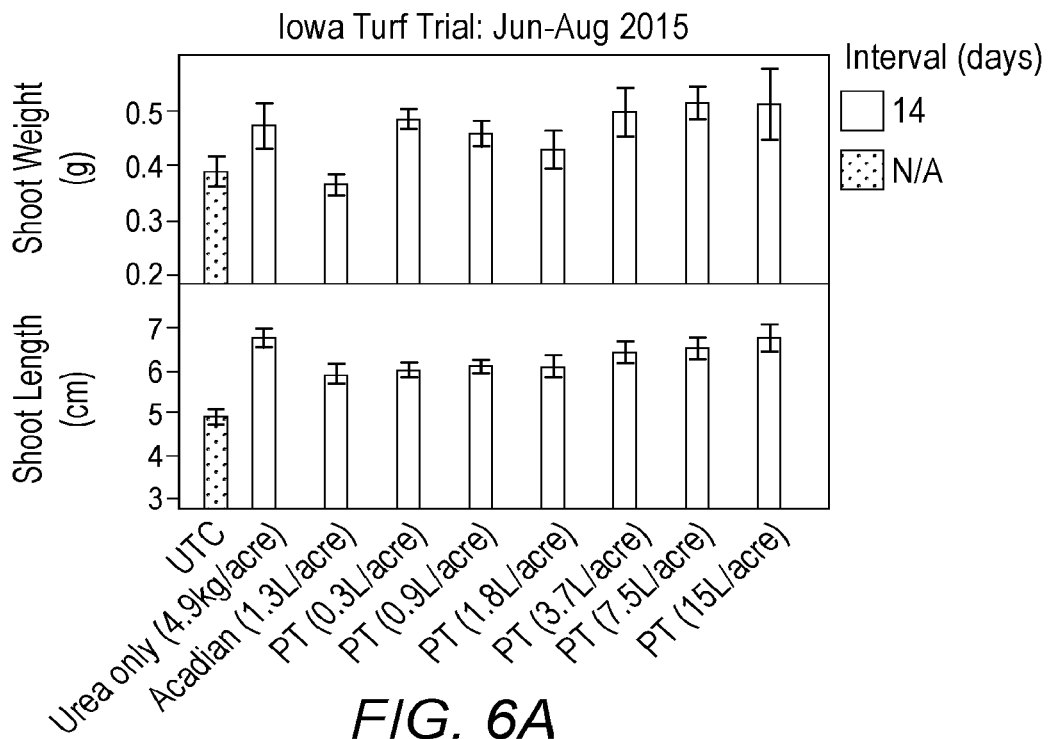
FIGS. 6A-6B depict results of experiments using the composition on turf.
Figure 6B:
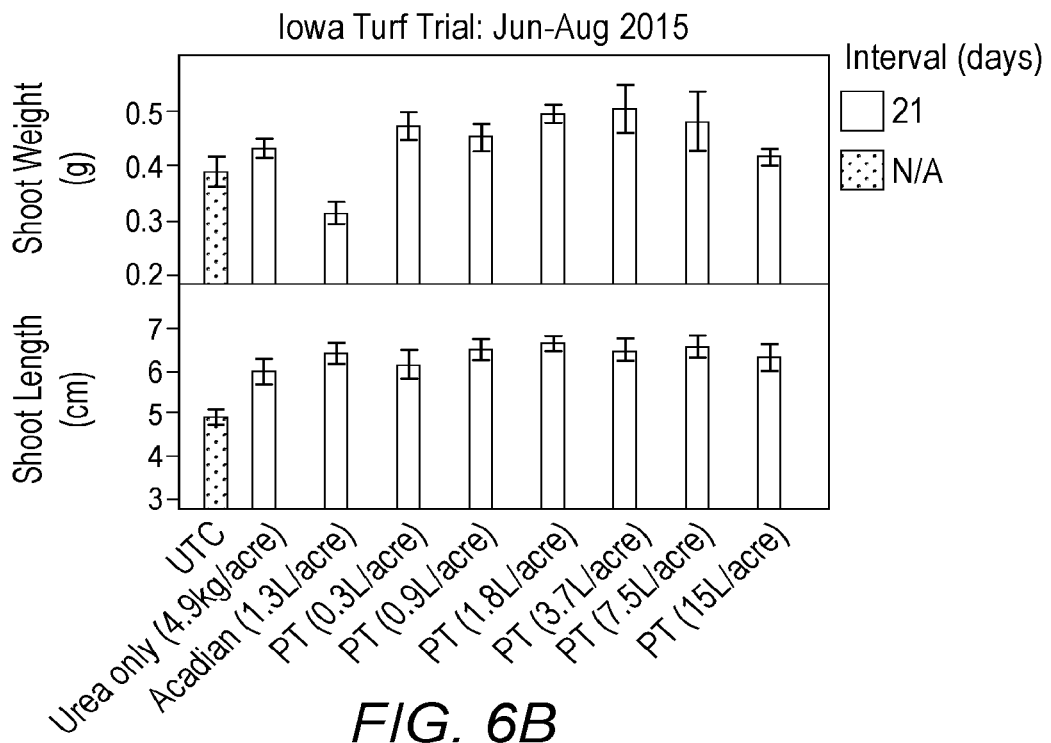

Experiments were conducted to determine if an application of a low concentration mixotrophic *Chlorella*-based composition (designated "PhycoTerra" or "PT" in figure legends) to turf affected the yield of the plants. In the experiments, the composition was applied to turfgrass at 6 different concentrations with urea. The concentrations ranged from 0.3-15 L/acre and the turf was treated at either 14- or 21-day intervals. These treatments were compared to turf samples that were given (1) no treatment (UTC), (2) Acadian (a seaweed extract composition) and (2) urea only. The results of the experiment are shown in FIG. 6A-6B. The shoot weight was shown to respond significantly to the treatment: At an application rate of 15 L/acre with an interval of 14 days, the shoot weight was found to be <30% higher than the untreated control (UTC) and all application rates gave significantly higher shoot weight than was achieved with application of Acadian at a 21-day interval of application.

Example 21

Figure 7A:
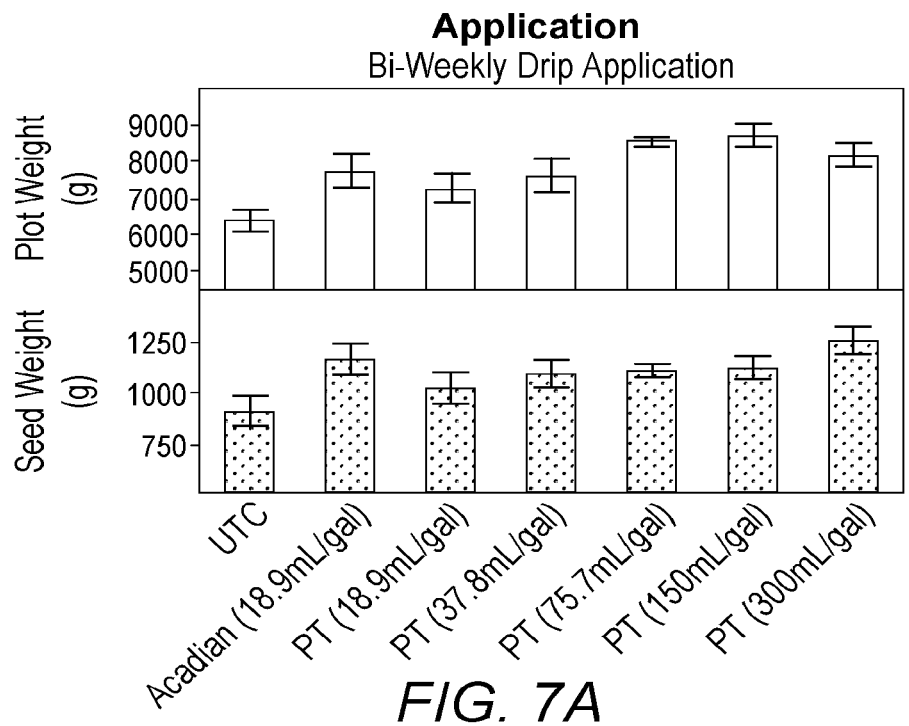
FIGS. 7A-7B depict results of experiments using the composition on peanuts.
Figure 7B:
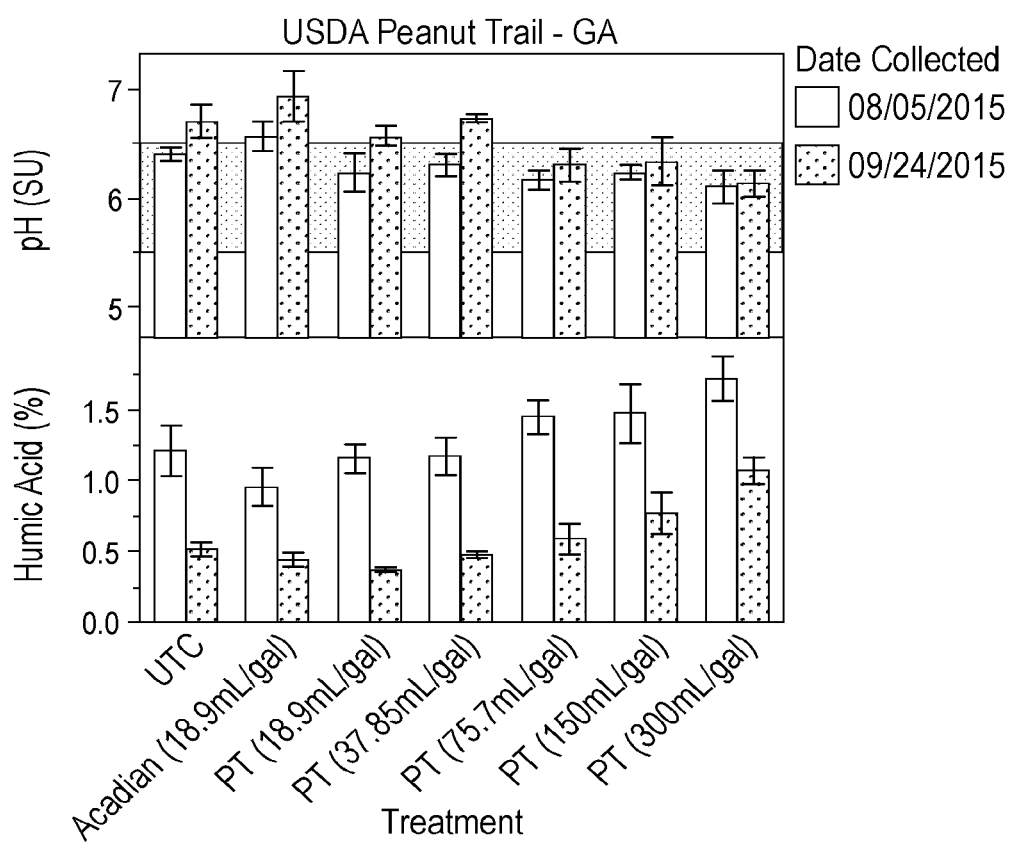

Experiments were conducted to determine if application of a low concentration mixotrophic *Chlorella*-based composition (PT) to peanuts affected the yield of the plants. In the experiments, the composition was applied at 5 different concentrations. These treatments were compared to plants that were given no treatment (UTC) and to plants that were treated with Acadian (a seaweed extract composition). In the experiments, the soil around in the plants was tested for pH and humic acid. As known in the art, a pH soil range of 5.5-6.5 is ideal for peanuts. Humic acid is an indicator of decomposition in the soil. The experiments show that the plot weight was significantly increased with PT given at 75.7 mL/gal-300 mL/gal and that the seed weight likewise was significantly increased with PT given at 300 mL/gal. The results of the experiment are shown in the Table 78 below and FIG. 7A-7B.

TABLE 78

| Level | | Least Sq Mean |
|---|---|---|
| PT (150 mL/gal) | A | 8743.0288 |
| PT (75.7 mL/gal) | A | 8555.8791 |
| PT (300 mL/gal) | A | 8181.6657 |
| Acadian (18.9 mL/gal) | A B | 7739.4135 |
| PT (37.8 mL/gal) | A B | 7626.0155 |
| PT (18.9 mL/gal) | A B | 7268.8118 |
| UTC | B | 6367.2977 |
| PT (300 mL/gal) | A | 1259.7500 |
| Acadian (18.9 mL/gal) | A B | 1167.2500 |
| PT (150 mL/gal) | A B | 1127.0000 |
| PT (75.7 mL/gal) | A B | 1112.2500 |
| PT (37.8 mL/gal) | A B | 1096.5000 |
| PT (18.9 mL/gal) | A B | 1028.5000 |
| UTC | B | 916.2500 |

Example 22

Experiments were conducted to determine if an application of a low concentration mixotrophic *Chlorella*-based composition to Basil plants affected the yield of the plants. In the experiments, the composition was applied after/in addition to an application of a commercial hydroponics fertilizer. This treatment was compared with fertilizer alone as a control. In these experiments, plants exposed to the treatment, and other plants exposed to the control, were compared based upon measurements of stem diameter and plant fresh weight. While the stem diameter showed no significant difference between the treatment and the control, the measure of fresh weight did demonstrate that the composition has a positive effect on plant growth, as compared with the fertilizer alone.

Example 23—Fabaceae (Leguminosae)

Experiments are conducted to test effects of application of a microalgae-based composition to crop plants of the family Fabaceae (Leguminosae). Application is done as in other examples herein, such that, in various treatments, (a) seeds are wetted or soaked in the composition; (b) the composition is applied to soil pre-germination; (c) the composition is applied to soil post-germination; (d) the composition is applied periodically to soil during the growing season; and/or (e) the composition is applied to leaves of the plants once or periodically during the growing season. Results are measures for appropriate plant characteristics including: seed germination rate, seed germination time, seedling emergence, seedling emergence time, seedling size, plant fresh weight, plant dry weight, utilization, fruit production, leaf production, leaf formation, thatch height, plant health, plant resistance to salt stress, plant resistance to heat stress, plant resistance to heavy-metal stress, plant resistance to drought, maturation time, yield, root length, root mass, color, insect damage, blossom end rot, softness, fruit quality, and sunburn. Results show at least a 10% quantitative improvement as to at least one characteristic under at least one mode of application (a-e) of the composition. In some embodiments, results show at least a 25% quantitative improvement in at least one characteristic and/or a statistically significant improvement in at least two characteristics.

Example 24—Poaceae

Experiments are conducted to test effects of application of a microalgae-based composition to crop plants of the family Poaceae. Application is done as in other examples herein, such that, in various treatments, (a) seeds are wetted or soaked in the composition; (b) the composition is applied to soil pre-germination; (c) the composition is applied to soil post-germination; (d) the composition is applied periodically to soil during the growing season; and/or (e) the composition is applied to leaves of the plants once or periodically during the growing season. Results are measures for appropriate plant characteristics including: seed germination rate, seed germination time, seedling emergence, seedling emergence time, seedling size, plant fresh weight, plant dry weight, utilization, fruit production, leaf production, leaf formation, thatch height, plant health, plant resistance to salt stress, plant resistance to heat stress, plant resistance to heavy-metal stress, plant resistance to drought, maturation time, yield, root length, root mass, color, insect damage, blossom end rot, softness, fruit quality, and sunburn. Results show at least a 10% quantitative improvement as to at least one characteristic under at least one mode of application (a-e) of the composition. In some embodiments, results show at least a 25% quantitative improvement in at least one characteristic and/or a statistically significant improvement in at least two characteristics.

Example 25—Roasaceae

Experiments are conducted to test effects of application of a microalgae-based composition to crop plants of the family Roasaceae. Application is done as in other examples herein, such that, in various treatments, (a) seeds are wetted or soaked in the composition; (b) the composition is applied to soil pre-germination; (c) the composition is applied to soil post-germination; (d) the composition is applied periodically to soil during the growing season; and/or (e) the composition is applied to leaves of the plants once or periodically during the growing season. Results are measures for appropriate plant characteristics including: seed germination rate, seed germination time, seedling emergence, seedling emergence time, seedling size, plant fresh weight, plant dry weight, utilization, fruit production, leaf production, leaf formation, thatch height, plant health, plant resistance to salt stress, plant resistance to heat stress, plant resistance to heavy-metal stress, plant resistance to drought, maturation time, yield, root length, root mass, color, insect damage, blossom end rot, softness, fruit quality, and sunburn. Results show at least a 10% quantitative improvement as to at least one characteristic under at least one mode of application (a-e) of the composition. In some embodiments, results show at least a 25% quantitative improvement in at least one characteristic and/or a statistically significant improvement in at least two characteristics.

Example 26—Vitaceae

Experiments are conducted to test effects of application of a microalgae-based composition to crop plants of the family Vitaceae. Application is done as in other examples herein, such that, in various treatments, (a) seeds are wetted or soaked in the composition; (b) the composition is applied to soil pre-germination; (c) the composition is applied to soil post-germination; (d) the composition is applied periodically to soil during the growing season; and/or (e) the composition is applied to leaves of the plants once or periodically during the growing season. Results are measures for appropriate plant characteristics including: seed germination rate, seed germination time, seedling emergence, seedling emergence time, seedling size, plant fresh weight, plant dry weight, utilization, fruit production, leaf production, leaf formation, thatch height, plant health, plant resistance to salt stress, plant resistance to heat stress, plant resistance to heavy-metal stress, plant resistance to drought, maturation time, yield, root length, root mass, color, insect damage, blossom end rot, softness, fruit quality, and sunburn. Results show at least a 10% quantitative improvement as to at least one characteristic under at least one mode of application (a-e) of the composition. In some embodiments, results show at least a 25% quantitative improvement in at least one characteristic and/or a statistically significant improvement in at least two characteristics.

Example 27—Brassicaeae (Cruciferae)

Experiments are conducted to test effects of application of a microalgae-based composition to crop plants of the family Brassicaeae (Cruciferae). Application is done as in other examples herein, such that, in various treatments, (a) seeds are wetted or soaked in the composition; (b) the composition is applied to soil pre-germination; (c) the composition is applied to soil post-germination; (d) the composition is applied periodically to soil during the growing season; and/or (e) the composition is applied to leaves of the plants once or periodically during the growing season. Results are measures for appropriate plant characteristics including: seed germination rate, seed germination time, seedling emergence, seedling emergence time, seedling size, plant fresh weight, plant dry weight, utilization, fruit production, leaf production, leaf formation, thatch height, plant health, plant resistance to salt stress, plant resistance to heat stress, plant resistance to heavy-metal stress, plant resistance to drought, maturation time, yield, root length, root mass, color, insect damage, blossom end rot, softness, fruit quality, and sunburn. Results show at least a 10% quantitative improvement as to at least one characteristic under at least one mode of application (a-e) of the composition. In some embodiments, results show at least a 25% quantitative improvement in at least one characteristic and/or a statistically significant improvement in at least two characteristics.

Example 28—Caricaceae

Experiments are conducted to test effects of application of a microalgae-based composition to crop plants of the family Caricaceae. Application is done as in other examples herein, such that, in various treatments, (a) seeds are wetted or soaked in the composition; (b) the composition is applied to soil pre-germination; (c) the composition is applied to soil post-germination; (d) the composition is applied periodically to soil during the growing season; and/or (e) the composition is applied to leaves of the plants once or periodically during the growing season. Results are measures for appropriate plant characteristics including: seed germination rate, seed germination time, seedling emergence, seedling emergence time, seedling size, plant fresh weight, plant dry weight, utilization, fruit production, leaf production, leaf formation, thatch height, plant health, plant resistance to salt stress, plant resistance to heat stress, plant resistance to heavy-metal stress, plant resistance to drought, maturation time, yield, root length, root mass, color, insect damage, blossom end rot, softness, fruit quality, and sunburn. Results show at least a 10% quantitative improvement as to at least one characteristic under at least one mode of application (a-e) of the composition. In some embodiments, results show at least a 25% quantitative improvement in at least one characteristic and/or a statistically significant improvement in at least two characteristics.

Example 29—Malvaceae

Experiments are conducted to test effects of application of a microalgae-based composition to crop plants of the family Malvaceae. Application is done as in other examples herein, such that, in various treatments, (a) seeds are wetted or soaked in the composition; (b) the composition is applied to soil pre-germination; (c) the composition is applied to soil post-germination; (d) the composition is applied periodically to soil during the growing season; and/or (e) the composition is applied to leaves of the plants once or periodically during the growing season. Results are measures for appropriate plant characteristics including: seed germination rate, seed germination time, seedling emergence, seedling emergence time, seedling size, plant fresh weight, plant dry weight, utilization, fruit production, leaf production, leaf formation, thatch height, plant health, plant resistance to salt stress, plant resistance to heat stress, plant resistance to heavy-metal stress, plant resistance to drought, maturation time, yield, root length, root mass, color, insect damage, blossom end rot, softness, fruit quality, and sunburn. Results show at least a 10% quantitative improvement as to at least one characteristic under at least one mode of application (a-e) of the composition. In some embodiments, results show at least a 25% quantitative improvement in at least one characteristic and/or a statistically significant improvement in at least two characteristics.

Example 30—Sapindaceae

Experiments are conducted to test effects of application of a microalgae-based composition to crop plants of the family Sapindaceae. Application is done as in other examples herein, such that, in various treatments, (a) seeds are wetted or soaked in the composition; (b) the composition is applied to soil pre-germination; (c) the composition is applied to soil post-germination; (d) the composition is applied periodically to soil during the growing season; and/or (e) the composition is applied to leaves of the plants once or periodically during the growing season. Results are measures for appropriate plant characteristics including: seed germination rate, seed germination time, seedling emergence, seedling emergence time, seedling size, plant fresh weight, plant dry weight, utilization, fruit production, leaf production, leaf formation, thatch height, plant health, plant resistance to salt stress, plant resistance to heat stress, plant resistance to heavy-metal stress, plant resistance to drought, maturation time, yield, root length, root mass, color, insect damage, blossom end rot, softness, fruit quality, and sunburn. Results show at least a 10% quantitative improvement as to at least one characteristic under at least one mode of application (a-e) of the composition. In some embodiments, results show at least a 25% quantitative improvement in at least one characteristic and/or a statistically significant improvement in at least two characteristics.

Example 31—Anacardiaceae

Experiments are conducted to test effects of application of a microalgae-based composition to crop plants of the family Anacardiaceae. Application is done as in other examples herein, such that, in various treatments, (a) seeds are wetted or soaked in the composition; (b) the composition is applied to soil pre-germination; (c) the composition is applied to soil post-germination; (d) the composition is applied periodically to soil during the growing season; and/or (e) the composition is applied to leaves of the plants once or periodically during the growing season. Results are measures for appropriate plant characteristics including: seed germination rate, seed germination time, seedling emergence, seedling emergence time, seedling size, plant fresh weight, plant dry weight, utilization, fruit production, leaf production, leaf formation, thatch height, plant health, plant resistance to salt stress, plant resistance to heat stress, plant resistance to heavy-metal stress, plant resistance to drought, maturation time, yield, root length, root mass, color, insect damage, blossom end rot, softness, fruit quality, and sunburn. Results show at least a 10% quantitative improvement as to at least one characteristic under at least one mode of application (a-e) of the composition. In some embodiments, results show at least a 25% quantitative improvement m at least one characteristic and/or a statistically significant improvement in at least two characteristics.

Example 32

Experiments were conducted to test variations in bacterial population among different batches of a low concentration mixotrophic *Chlorella*-based composition (PT Brown, PT Field, PT Fresh, PT Hydro, PT New and PT Texas). In all batches, dominant taxa included *Paenibacillus, Bacillus, Lactobacillus*, and *Brevibacillus*. *Paenibacillus* and *Bacillus* are known to secrete a myriad of beneficial compounds in the rhizosphere of plants (phytohormones, nitrogenous compounds, antibiotics). They are also known to mitigate pathogens. *Lactobacillus* is a fermentative lactic acid producing bacterium used in the agricultural practice of silage. *Brevibacillus* is less known as a common plant growth promoting genus, however some literature exists demonstrating its ability to leach heavy metals from the rhizosphere. While some quantitative variability of each bacterial population existed from batch to batch, these four sporulating bacterial taxa were predominant. It is believed that the pasteurization treatment of the composition differentially suppressed other non-sporulating taxa, which were found to be present but in significantly lower amounts.

Example 33

Experiments were conducted to test the stability of variations in batches of a microalgae *Chlorella*-based composition at different storage temperatures. Samples were tested monthly at various temperatures (2-5° C., 35° C., or 40° C.) for six months. Bacterial counts were determined as well as levels of total nitrogen, phosphorous and potassium. The results of the experiments demonstrated that under different conditions, bacterial counts varied but nutrient levels remained essentially stable.

Example 34

Figure 8:
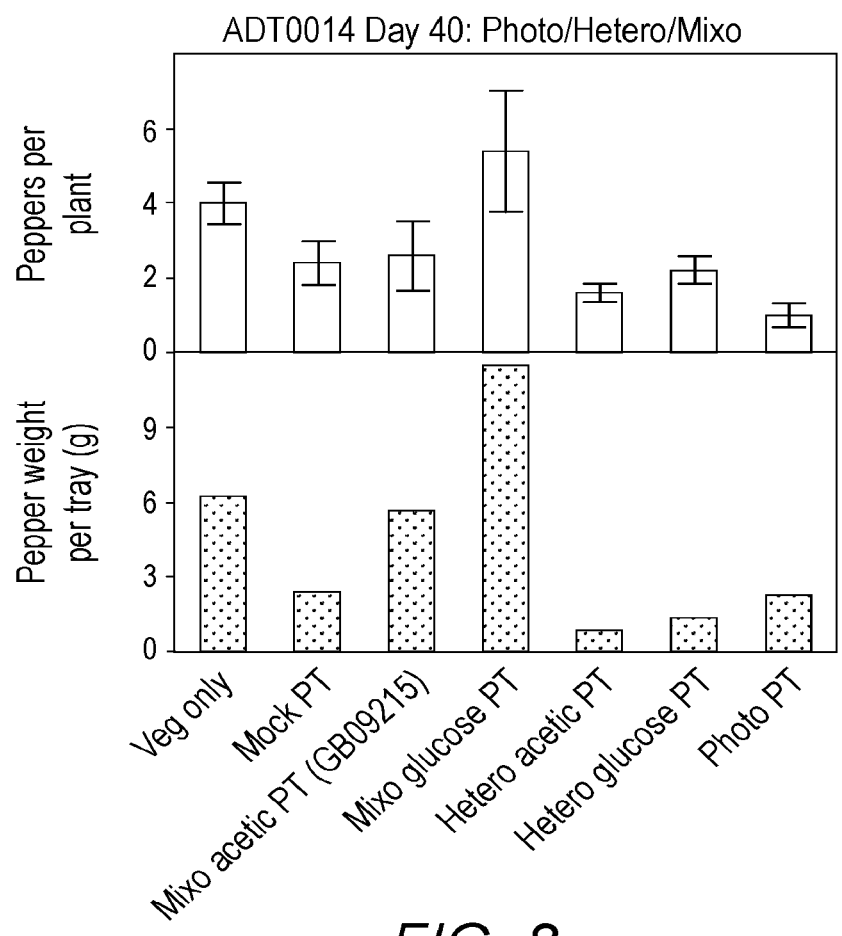
FIG. 8 depicts results of experiments involving different preparations of the composition.

Experiments were conducted to test different methods of preparation of a microalgae *Chlorella*-based composition (PT). *Chlorella* is capable of heterotrophy (consuming an external carbon source), phototrophy (photosynthesis to convert CO2 into a useable carbon source), and also mixotrophy (simultaneously receiving nutrition/carbon via photosynthesis and also by consuming available external carbon sources). Compositions of purely heterotrophic *Chlorella*, raised on two different carbon sources (either acetic acid or glucose), were compared with phototrophic *Chlorella* and also with mixotrophic *Chlorella*, also grown in two batches each raised on either acetic acid or glucose as its carbon source. The results of the experiments are shown in FIG. 8. Mixotrophic cultures grew most rapidly but also showed better results when applied to plants as compared with other cultures.

Example 35

In one non-limiting example of mixotrophic culturing of *Chlorella* for the described method of preparation of a composition for application to plants, the *Chlorella* is cultured in a BG-11 culture media or a media derived from BG-11 culture media (e.g., in which additional component(s) are added to the media and/or one or more elements of the media is increased by 5%, 10%, 15%, 20%, 25%, 33%, 50%, or more over unmodified BG-11 media) for a culture length of 7-14 days in an open culturing vessel. The temperature can range from 20-30° C., or more, and the pH ranges from 6.5-8.5. The dissolved oxygen concentration can range from 0.1-4 mg/L. The culture receives acetic acid or acetate as a source of organic carbon, supplying carbon as energy source to the *Chlorella* cells and regulating the pH, and is supplied to the culture in a feed with a concentration in the range of 10-90% by a pH auxostat system. The culture receives natural sunlight (comprising photosynthetically active radiation) as a source of energy. Mixing is provided by air sparging through an aerotube, and fluid propulsion by thrusters submerged in the liquid culture. Alternative organic carbon sources can include, for example, any of: ammonium linoleate, arabinose, arginine, aspartic acid, butyric acid, cellulose, citric acid, ethanol, fructose, fatty acids, galactose, glucose, glycerol, glycine, lactic acid, lactose, maleic acid, maltose, mannose, methanol, molasses, peptone, plant based hydrolyzate, proline, propionic acid, ribose, sacchrose, partial or complete hydrolysates of starch, sucrose, tartaric, TCA-cycle organic acids, thin stillage, urea, industrial waste solutions, yeast extract, any combination of the foregoing, or other organic carbon sources.

Example 36

In an alternative embodiment to the embodiment described in Example 40, aerators can be used as alternatives to spargers and submerged thrusters to provide both infusion of gases (e.g., oxygen) into the aqueous microalgae culture and turbulent mlxmg of the microalgae culture. One non-limiting example of an aerator for use as an alternative to the combination of spargers and submerged thrusters is the Aire-02® Series 275 Aspirator Aerator (Aeration Industries International, Chaska, MN USA). Such aerators include an electric motor drive above the culture media surface mounted on a float, a hollow shaft extending at an angle from above the culture media surface into the culture, and a propeller disposed at end of the shaft which is submerged within the culture media. The motor is coupled to and drives the shaft and propeller. The propeller thrusts the aqueous culture media past a diffuser at the end of the shaft to induce a pressure differential in the hollow shaft, drawing air through intake holes in the shaft above the culture media surface down through the rotating hollow shaft and diffuser into the microalgae culture. While the aerators contribute to the turbulent mixing and infusion of oxygen, the previously described devices and methods of supplying nutrients, supplying organic carbon, and controlling pH can be used in conjunction with such aerators.

Example 37

In one non-limiting example of preparing the liquid composition with the mixotrophic *Chlorella*-based composition for application to plants, the mixotrophic *Chlorella*-based composition harvested from the culturing system is first held in a harvest tank before centrifuging the culture. Once the mixotrophic *Chlorella* culture is centrifuged, the centrifuge discharges the fraction rich in mixotrophic *Chlorella* whole cell solids, but also containing the accompanying constituents from the culture medium, into a container at a temperature of about 30° C. The mixotrophic *Chlorella*-based composition can continue (i.e., fresh) in the process of preparing the liquid composition or be stored in a freezer and thawed at a later time (i.e., stored) for processing into the liquid composition. When the mixotrophic *Chlorella*-based composition is stored in a freezer, the storage temperature is about −10° C. and about 1-2 days are required for the composition to freeze. Once removed from the freezer, the stored mixotrophic *Chlorella*-based composition is placed outside to thaw for about 7 days. The fresh or stored mixotrophic *Chlorella*-based composition is then placed in a tank and heated to a temperature of about 60° C. for about 2 hours to begin the pasteurization process. The mixotrophic *Chlorella*-based composition is then diluted to a whole cells solids concentration of about 10-11% by weight and cooled to about 40° C. to complete the pasteurization process. The pH of the mixotrophic *Chlorella*-based composition is then adjusted to a pH of about 4 by mixing in an effective amount of phosphoric acid for stabilization purposes. About 0.3% potassium sorbate is then mixed with the mixotrophic *Chlorella*-based composition for stabilization purposes. The resulting liquid composition is then transferred to containers of a desired size stored at 3-5° C. until shipped.

Example 38

Using QPCR (quantitative polymerase chain reaction) to analyze the bacteria population in a mixotrophic *Chlorella* culture before pasteurization and after pasteurization, it was observed that the profile of bacteria in the culture changes after pasteurization. Particularly, the post-pasteurization profile of bacteria includes a higher proportion of spore forming bacteria and includes, but is not limited to, *Paenibacillus* sp., *Bacillus* sp., *Lactobacillus* sp., and *Brevibacillus* sp as the dominant types of bacteria. Comparing the aerobic plate counts of a mixotrophic *Chlorella* culture before pasteurization and after pasteurization, it was also observed that the total number of bacteria in the culture is lower after pasteurization. Combinations of temperature and time for the pasteurization process for the times of 15, 30, 60, 120, 180, and 360 minutes, and 50, 6-0, 70, 80, and 90° C. were tested with a culture of mixotrophic *Chlorella*, and the resulting aerobic plate counts ranged from 7.58×106 CFU to as low as 1.74×103 CFU. Storage temperature was also shown to vary the profile of bacteria of a pasteurized culture of mixotrophic *Chlorella*, with samples stored at temperatures of 2-4° C., 25° C., and 40° C. varying in the aerobic plate count numbers and type of dominant bacteria species over time.

While the mixotrophic *Chlorella* cells are intact and viable (i.e., physically fit to live, capable of further growth or cell division) after being harvested from the culture, the *Chlorella* cells resulting from the pasteurization process were confirmed to have intact cell walls but were not viable. Mixotrophic *Chlorella* cells resulting from the pasteurization process were observed under a microscope to determine the condition of the cell walls after the being subjected to the heating and cooling of the process, and it was visually confirmed that the *Chlorella* cell walls were intact and not broken open. For further investigation of the condition of the cell, a culture of live mixotrophic *Chlorella* cells and the mixotrophic *Chlorella* cells resulting from the pasteurization process were subjected to propidium iodide, an exclusion fluorescent dye that labels DNA if the cell membrane is compromised, and visually compared under a microscope. The propidium iodide comparison showed that the *Chlorella* cells resulting from the pasteurization process contained a high amount of dyed DNA, resulting in the conclusion that the mixotrophic *Chlorella* cell walls were intact, but the cell membranes were compromised. Thus, the permeability of the pasteurized *Chlorella* cells differs from the permeability of a *Chlorella* cell with both an intact cell wall and cell membrane.

Additionally, a culture of live mixotrophic *Chlorella* cells and the mixotrophic *Chlorella* cells resulting from the pasteurization process were subjected to DAPI (4',6-diamidino-2-phyenylindole)-DNA binding fluorescent dye and visually compared under a microscope. The DAPI-DNA binding dye comparison showed that the *Chlorella* cells resulting from the pasteurization process contained a greatly diminished amount of viable DNA in the cells, resulting in the conclusion indicating that the mixotrophic *Chlorella* cells are not viable after pasteurization. The two DNA dying comparisons demonstrate that the pasteurization process has transformed the structure and function of the *Chlorella* cells from the natural state by changing: the cells from viable to non-viable, the condition of the cell membrane, and the permeability of the cells.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context.

Unless otherwise stated, all exact values provided herein are representative of corresponding approximate values (e.g., all exact exemplary values provided with respect to a particular factor or measurement can be considered to also provide a corresponding approximate measurement, modified by "about," where appropriate). All provided ranges of values are intended to include the end points of the ranges, as well as values between the end points.

The description herein of any aspect or embodiment of the invention using terms such as "comprising", "having," "including," or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims and/or aspects appended hereto as permitted by applicable law.

What is claimed is:

1. A liquid agricultural composition for application to a plant, seed, seedling, or soil, the composition comprising:
   pasteurized *Chlorella* cells,
   wherein the composition is effective in enhancing at least one characteristic of a plant compared to a substantially identical untreated plant.

2. The composition of claim 1, wherein the composition comprises 5-30% solids by weight of the *Chlorella* cells.

3. The composition of claim 1, wherein the composition comprises 5-15% solids by weight of the *Chlorella* cells.

4. The composition of claim 1, wherein the composition comprises less than 5% solids by weight of the *Chlorella* cells.

5. The composition of claim 1, wherein the composition is formulated for application to soil.

6. The composition of claim 1, wherein the composition is formulated for application to seeds and/or foliage.

7. The composition of claim 1, wherein the composition is effective in enhancing the at least one characteristic of the plant compared to a composition comprising non-pasteurized *Chlorella* cells and lacking the pasteurized *Chlorella* cells.

8. The composition of claim 1, wherein the at least one characteristic comprises one or more of: seed germination, seedling emergence, seedling size, plant fresh weight, plant dry weight, utilization, leaf production, leaf formation, thatch height, plant maturation, plant yield, plant growth, plant quality, plant health, plant resistance to salt stress, plant resistance to heat stress, plant resistance to heavy-metal stress, plant resistance to drought, maturation time, yield, root length, root mass, color, fruit production, fruit yield, fruit growth, and fruit quality.

9. The composition of claim 1, wherein the *Chlorella* cells are whole cells.

10. The composition of claim 1, further comprising one or more stabilizers.

11. The composition of claim 10, wherein the one or more stabilizers comprises one or more of: potassium sorbate, phosphoric acid, ascorbic acid, and sodium benzoate.

12. The composition of claim 10, wherein the one or more stabilizers comprises an acid.

13. The composition of claim 12, wherein the acid is phosphoric acid.

14. The composition of claim 10, wherein the one or more stabilizers comprises a yeast and mold inhibitor.

15. The composition of claim 14, wherein the yeast and mold inhibitor is potassium sorbate.

16. The composition of claim 1, wherein the pH of the composition is between 3 and 5.

17. The composition of claim 1, wherein the *Chlorella* cells have been pasteurized at a temperature ranging from 50° C. to 90° C.

18. The composition of claim 1, wherein the *Chlorella* cells are cultured in non-axenic, mixotrophic conditions.

19. The composition of claim 1, wherein the pasteurized *Chlorella* cells have intact cell walls and compromised cell membranes, wherein permeability of the pasteurized *Chlorella* cells differs from the permeability of non-pasteurized *Chlorella* cells having both intact cell walls and intact cell membranes.

20. The composition of claim 1, wherein the *Chlorella* cells have not been subjected to a drying process.

\* \* \* \* \*